United States Patent
Garvey et al.

(10) Patent No.: US 6,472,425 B1
(45) Date of Patent: Oct. 29, 2002

(54) METHODS FOR TREATING FEMALE SEXUAL DYSFUNCTIONS

(75) Inventors: David S. Garvey, Dover, MA (US); Inigo Saenz de Tejada, Madrid (ES)

(73) Assignee: NitroMed, Inc., Bedford, MA (US)

( * ) Notice: Subject to any disclaimer, the term of this patent is extended or adjusted under 35 U.S.C. 154(b) by 0 days.

(21) Appl. No.: 09/354,424

(22) Filed: Jul. 16, 1999

Related U.S. Application Data

(62) Division of application No. 09/297,381, filed as application No. PCT/US97/19870 on Oct. 31, 1997, now abandoned.

(51) Int. Cl.$^7$ .................. A61K 31/21; A61K 31/04; A61K 43/54; A01N 33/18; A01N 33/24

(52) U.S. Cl. .................. 514/509; 514/252; 514/258; 514/267; 514/292; 514/303; 514/742

(58) Field of Search ............... 514/252, 258, 514/509, 742; 544/256

(56) References Cited

U.S. PATENT DOCUMENTS

| | | | |
|---|---|---|---|
| 4,127,118 A | 11/1978 | Latorre | |
| 4,308,278 A | 12/1981 | Schneider et al. | |
| 4,421,754 A | * 12/1983 | Hidaka et al. | ........... 424/250 |
| 4,801,587 A | 1/1989 | Voss et al. | |
| 4,885,173 A | 12/1989 | Stanley et al. | |
| 4,963,541 A | 10/1990 | Brooks et al. | |
| 5,059,603 A | 10/1991 | Rubin | |
| 5,145,852 A | 9/1992 | Virag | |
| 5,171,217 A | 12/1992 | March et al. | |
| 5,190,967 A | 3/1993 | Riley | |
| 5,196,426 A | 3/1993 | Saccomano et al. | |
| 5,223,504 A | 6/1993 | Noverola et al. | |
| 5,254,575 A | 10/1993 | Pick et al. | |
| 5,256,652 A | 10/1993 | El-Rashidy | |
| 5,340,586 A | 8/1994 | Pike et al. | |
| 5,340,827 A | 8/1994 | Beeley et al. | |
| 5,371,107 A | 12/1994 | Hotzel et al. | |
| 5,380,757 A | 1/1995 | Horrobin | |
| 5,380,758 A | * 1/1995 | Stamler et al. | ........... 514/562 |
| 5,399,581 A | 3/1995 | Laragh | |
| 5,426,107 A | 6/1995 | Bell et al. | |
| 5,438,060 A | 8/1995 | Miyazaki et al. | |
| 5,439,938 A | 8/1995 | Snyder et al. | |
| 5,447,912 A | 9/1995 | Gerstenberg et al. | |
| 5,474,535 A | 12/1995 | Place et al. | |
| 5,491,147 A | 2/1996 | Boyd et al. | |
| 5,492,911 A | 2/1996 | Stief | |
| 5,543,430 A | * 8/1996 | Kaesemeyer | ........... 514/565 |
| 5,545,647 A | 8/1996 | Tanaka et al. | |
| 5,565,466 A | * 10/1996 | Gioco et al. | ........... 514/280 |
| 5,567,706 A | 10/1996 | Gavras | |
| 5,574,068 A | 11/1996 | Stamler et al. | |
| 5,583,101 A | 12/1996 | Stamler et al. | |
| 5,618,814 A | 4/1997 | Heckel et al. | |
| 5,645,839 A | 7/1997 | Chobanian et al. | |
| 5,646,181 A | 7/1997 | Fung et al. | |
| 5,648,393 A | 7/1997 | Stamler et al. | |
| 5,698,589 A | 12/1997 | Allen | |
| 5,708,031 A | 1/1998 | Scott | |
| 5,718,917 A | 2/1998 | See | |
| 5,731,339 A | 3/1998 | Lowrey | |
| 5,767,160 A | 6/1998 | Kaesemeyer | |
| 5,770,606 A | 6/1998 | El-Rashidy et al. | |
| 5,773,457 A | 6/1998 | Nahoum | |
| 5,789,442 A | 8/1998 | Garfield et al. | |
| 5,824,669 A | 10/1998 | Garvey et al. | |
| 5,874,437 A | 2/1999 | Garvey et al. | |
| 5,877,216 A | 3/1999 | Place et al. | |
| 5,908,853 A | 6/1999 | Nahoum | |
| 5,910,316 A | 6/1999 | Keefer et al. | |
| 5,932,538 A | 8/1999 | Garvey et al. | |
| 5,945,117 A | 8/1999 | El-Rashidy et al. | |
| 5,952,361 A | 9/1999 | Dias Nahoum | |
| 5,958,926 A | 9/1999 | Garvey et al. | |
| 5,973,011 A | 10/1999 | Noack et al. | |
| 5,993,856 A | 11/1999 | Ragavan et al. | |
| 5,994,363 A | 11/1999 | El-Rashidy et al. | |
| 6,007,824 A | 12/1999 | Duckett et al. | |
| 6,017,521 A | 1/2000 | Robinson et al. | |
| 6,031,002 A | 2/2000 | Wysor et al. | |
| 6,036,977 A | 3/2000 | Drizen et al. | |
| 6,037,346 A | 3/2000 | Doherty, Jr. et al. | |
| 6,132,757 A | 10/2000 | Cutler | |
| 6,165,975 A | 12/2000 | Adams et al. | |
| 6,193,992 B1 | 2/2001 | El-Rashidy et al. | |
| 6,214,374 B1 | 4/2001 | Schmirler et al. | |
| 6,251,436 B1 | 6/2001 | Drizen et al. | |
| 6,258,373 B1 | 7/2001 | Cutler | |
| 6,277,884 B1 | 8/2001 | Saenz de Tejada | |
| 6,306,841 B1 | 10/2001 | Place et al. | |

FOREIGN PATENT DOCUMENTS

| | | | |
|---|---|---|---|
| DE | 43 21 109 | * | 1/1995 |
| EP | 0252721 | | 1/1988 |
| EP | 0346297 | | 12/1989 |

(List continued on next page.)

OTHER PUBLICATIONS

"Spontaneous nitric oxide release accounts for the potent pharmacological actions of FK409", Kita et al. European J. of Pharmacology. vol. 257 (1994) pp. 123–130.*

(List continued on next page.)

*Primary Examiner*—Mukund J. Shah
*Assistant Examiner*—Zachary C. Tucker
(74) *Attorney, Agent, or Firm*—Hale and Dorr LLP

(57) ABSTRACT

The present invention provides methods for treating female sexual dysfunctions by administering to a female individual a therapeutically effective amount of at least one compound that donates, transfers or releases nitrogen monoxide, that induces the production of endogenous endothelium-derived relaxing factor, that stimulates endogenous synthesis of nitrogen monoxide, or that is a substrate for nitric oxide synthase. The methods may further comprise administering a therapeutically effective amount of a phosphodiesterase inhibitor and/or a nitrosated and/or nitrosylated phosphodiesterase inhibitor.

15 Claims, 40 Drawing Sheets

FOREIGN PATENT DOCUMENTS

Figure 1:
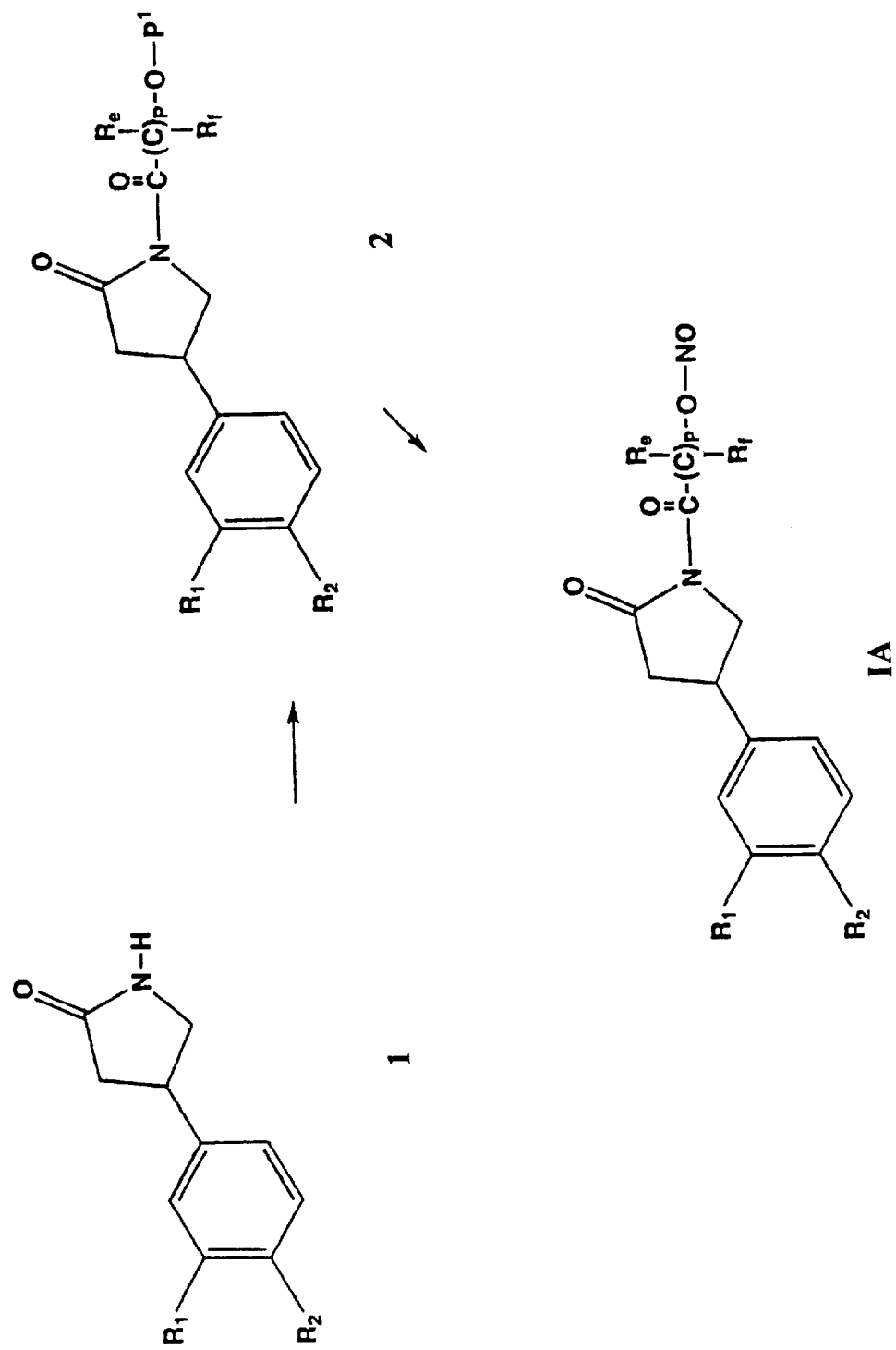

| | | |
|---|---|---|
| EP | 0 352 960 | 1/1990 |
| EP | 0357581 | 3/1990 |
| EP | 0432199 | 6/1991 |
| EP | 0442204 | 8/1991 |
| EP | 463756 | 1/1992 |
| EP | 0 463 756 | 1/1992 |
| EP | 0506194 | 9/1992 |
| EP | 0 611 248 | 8/1994 |
| FR | 2547501 | 12/1984 |
| JP | 8-26962 | 1/1996 |
| WO | 9306104 | 4/1993 |
| WO | 9312068 | 6/1993 |
| WO | WO 94/04120 | 3/1994 |
| WO | 9501338 | 1/1995 |
| WO | 9505172 | 2/1995 |
| WO | 9509636 | 4/1995 |
| WO | WO 95/26725 | 10/1995 |
| WO | 9526768 | 10/1995 |
| WO | WO 96 25184 | 8/1996 |
| WO | 9727749 | 8/1997 |
| WO | 9734871 | 9/1997 |
| WO | 9739760 | 10/1997 |
| WO | 9819672 | 5/1998 |
| WO | 9901132 | 1/1999 |
| WO | 9921558 | 5/1999 |
| WO | 9921562 | 5/1999 |
| WO | 9922731 | 5/1999 |

OTHER PUBLICATIONS

"Nitric Oxide–based Possibilities for Pharmacotherapy", Porsti et al. Annals of Medicine. vol. 27 (1995) pp. 407–420.*

"Vasculogenic female sexual dysfunction: The hemodynamic basis for vaginal engorgement insufficiency and clitoral erectile insufficiency", Park et al. International J. of Impotence of Res. vol. 9 (Mar. 1997) pp. 27–37.*

New NO–Donors with Antithrombotic and Vasodilationg Activities, VI: Thiazole–2–nitrosimines. Rehse et al. Arch. Pharm. vol. 327 (1994) pp 581–589.*

Wilson and Gisvold's Textbook of Organic Medicinal and Pharmaceutical Chemistry. pp. 535–539 and 582. Jaime N. Delgado and William A. Remers, editors. J.B. Lippincott Co, publishers. (1991).*

Chemical Abstracts, 120(1):612, Abstract 5451d (1994).

EPO Communication for PCT/US97/19870 (Aug. 4, 1999).

Supplementary Partial European Search Report for EP 97 94 6871 (May 25, 2000).

Boolell et al, British Journal of Urology, 78(2):257–261 (1996).

Martel et al, Drugs of the Future, 22(2):138–143 (1997).

Chemical Abstracts, vol. 125, No. 15, Abstract No. 191382 (Oct. 7, 1996).

Chemical Abstracts, vol. 123, No. 1, Abstract No. 574 (Jul. 3, 1995).

Chemical Abstracts, vol. 120, No. 25, Abstract No. 315630 (Jun. 20, 1994).

Chemical Abstracts, vol. 121, No. 7, Abstract No. 73410 (Aug. 15, 1994).

Chemical Abstracts, vol. 116, No. 1, Abstract No. 4477 (Jan. 6, 1992).

Sonda et al, Journal of Sex & Marital Therapy, 16(1):15–21 (1990).

Berman et al, Urology, 54(3):385–391 (1999).

Halvorsen et al, JABFP, 5(1):51–61 (1992).

Levin, Exp. Clin. Endocrinol., 98(2):61–69 (1991).

Goodnow, Chicago Tribune, Section 13, p. 8 (Dec. 14, 1997).

Boolell et al, *International Journal of Impotence Research*, 8:47–52 (1996).

Krane et al, *New England Journal of Medicine*, 321(24):1648–1659 (1989).

Trigo–Rocha et al, *Neurourol. Urodyn.*, 13(1):71–80 (1994).

Sparwasser et al, *J. Urol.*, 152:6, Pt. 1, pp. 2159–2163 (1994).

Zorgniotti et al, *Int. J. Impotence Res.*, 6:33–36 (1994).

Mathers et al, *European Urology*, 35(suppl 2):67 (abstract 266) (1999).

Terrett et al, *Bioorg. Med. Chem. Lett.*, 6(15):1819–1824 (1996).

Park et al, *Biochem. Biophys. Res. Commun.*, 249(3):612–617 (1998).

* cited by examiner

US 6,472,425 B1

METHODS FOR TREATING FEMALE SEXUAL DYSFUNCTIONS

This is a divisional of U.S. application Ser. No. 09/297,381, filed Apr. 30, 1999, now abandoned, which is a § 371 of PCT Application No. PCT/US97/19870, filed Oct. 31, 1997, which claims priority to U.S. application Ser. No. 08/740,764, filed Nov. 1, 1996, issued as U.S. Pat. No. 5,874,437.

BACKGROUND OF THE INVENTION

This invention generally relates to pharmaceuticals and more specifically to a method and compositions for inducing penile erections in human males suffering from impotence, a method and compositions for treating female sexual dysfunction, and a method and compositions for treating human anal disease resulting from excessive anal sphincter tone.

Male erectile dysfunction is a widespread disorder that is thought to affect about ten to fifteen percent of the adult men. In a similar fashion, it is now beginning to be recognized that female sexual dysfunction is also a significant problem among adult women. With the male cases, a number of causes of these insufficiencies, in addition to anatomical deficiencies of the penis that preclude an erection sufficient for vaginal penetration, have been identified. Causes of erectile dysfunction can be categorized as psychogenic, neurogenic, endocrinologic, drug-induced, or vasculogenic and in any male suffering from erectile dysfunction there may be more than one cause. Female sexual dysfunction may also be categorized as psychogenic, neurogenic, endocrinologic, drug-induced, or vasculogenic and a female with one or more of these etiologies may also experience a lack of satisfaction in sexual relations.

Psychogenic impotence is often the result of anxiety or depression, with no apparent somatic or organic impairment. Neurogenic impotence may arise from, for example, surgery or a pelvic injury, involving the nervous system affecting the penis or vagina. Sexual dysfunction which is in endocrinologic in origin is most often associated with the disorders hypo- or hypergonadotropic hypogonadism and hyperprolactinein the male and decreases in estrogens in the female.

Vasculogenic sexual dysfunction is thought to be the most frequent cause of sexual dysfunction accounting for approximately fifty percent of all cases of organic sexual dysfunction. In these cases, the erectile dysfunction may be attributed to alterations in the flow of blood to and from the penis while in the female cases vaginal engorgement insufficiency and clitoral erectile insufficiency may be attributed to alterations in blood flow to the vagina and clitoris respectively. Atherosclerotic or traumatic arterial occlusive disease to the arteries which supply blood to the penis can lead to a decrease in the rigidity of the erect penis as well as increase the time to achieving maximal erection. In an analogous fashion, disease which impairs blood flow to the hypogastric-vaginal/clitoral arterial bed may lead to vaginal engorgement insufficiency and clitoral erectile insufficiency. In still other cases, there is an inability to retain blood in the penis or clitoris such that sufficient pressure for an erection can be neither obtained nor maintained.

There is also a high incidence of erectile insufficiency among male diabetics, particularly those with insulin-dependent diabetes mellitus. Erectile dysfunction in male diabetics is often classified as "diabetogenic," although the underlying dysfunction is usually neurogenic and/or vasculogenic. About half of diabetic males suffer from erectile insufficiency, and about half of the cases of neurogenic impotence are in diabetics. A significant population of female diabetics also exhibit symptoms of sexual dysfunction, especially those with complications directly attributed to the disease.

Sexual dysfunction in both males and females is sometimes a side effect of certain drugs, such as beta-antagonists that are administered to reduce blood pressure in persons suffering from hypertension, or drugs administered to treat depression or anxiety. Excessive alcohol consumption has also been linked to sexual dysfunction. These forms of sexual dysfunction may be regarded as iatrogenic sexual dysfunction.

A number of methods to treat sexual dysfunction are available. These treatments include pharmacological treatments, surgery and, in cases of psychogenic dysfunction, psychological counseling is sometimes effective. Psychogenic sexual dysfunction often can be cured by counseling. Insufficiency due to excessive alcohol consumption is sometimes cured by reducing or eliminating such consumption.

In the rare cases in males, where the insufficiency is untreatable because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been employed, especially in cases where pharmacological intervention is ineffective. Such cases are usually associated with severe forms of vasculogenic impotence. Treatment of impotence with penile implants, however, entails serious disadvantages. Such treatment requires surgery and necessitates total destruction of the erectile tissues of the penis, forever precluding normal erection.

In the male population, pharmacological methods of treatment are also available. Such methods, however, have not proven to be highly satisfactory or without potentially severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a phosphodiesterase inhibitor and a smooth muscle relaxant, or phenoxybenzamine, a non-specific α-adrenergic antagonist and hypotensive, into a corpus cavernosum has been found to cause an erection sufficient for vaginal penetration however, these treatments are not without the serious and often painful side effect of priapisim. Also, in cases where severe atherosclerosis is not a cause of the dysfunction, intracavernosal injection of phentolamine, an α-adrenergic antagonist, has been shown to produce an erection sufficient for vaginal penetration, however, the resulting erection is one of significantly shorter duration than that induced by intracavernosal injection of papaverine or phenoxybenzamine. Thus, often times the erection is of such short duration that satisfactory sexual relations are difficult or impossible. As an alternative or, in some cases an adjunct to phosphodiesterase inhibition or α-adrenergic blockade for the treatment of erectile dysfunction, prostaglandin E1 (PGE1) has been administered via intracavernosal injection. A major side effect frequently associated intracorprally delivered PGE1 is penile pain and burning. Thus, there is a need for methods to induce and maintain a penile erection for a sufficient duration that satisfactory sexual relations are possible without also producing the undesirable side effects of those agents currently used. With regard to female sexual dysfunction, no pharmacological strategies have been yet devised for effective treatment A number of anorectal diseases involve excessive anal sphincter tone. For example, anal fissures as well as acutely thrombosed external hemorrhoids are normally accompanied by severe anal pain. Classical treatment of these conditions has usually involved surgery, however, in the treatment of more severe cases, surgical intervention is not without adverse side effects usually involving permanent sphincter defects and subsequent continence disturbances. Recently, nitric oxide has been implicated as the chemical messenger mediating relaxation of the internal anal sphincter. The local application of the exogenous nitric oxide (NO) donors nitroglycerin or isosorbide dinitrate has been reported to improve the symptoms and, in the case of anal fissure, facilitate the healing process. These treatments have not been without the production of undesired systemic side effects the most prevalent of which is headache. Thus, there is a need for methods to treat human anal disease involving excessive anal sphincter tone without also producing the undesirable side effects of those agents currently used.

Nitric oxide has been shown to mediate a number of actions including the bactericidal and tumoricidal actions of macrophages and blood vessel relaxation of endothelial cells. NO, and NO donors have also been implicated as mediators of nonvascular smooth muscle relaxation. This effect includes the dilation of the corpus cavernosum smooth muscle, an event involved in the penile and clitoral erection processes and the relaxation of the anal sphincter, an event necessary for normal defecation as well as an improvement in the symptoms of pain associated with many anal diseases. However, the effects of modified of phosphodiesterase inhibitors which are directly or indirectly linked with a nitric oxide adduct have not been investigated.

SUMMARY OF THE INVENTION

In the process of arriving at the present invention it was recognized that the risk of toxicities and adverse effects that are associated with high doses of phosphodiesterase inhibitors can be avoided by the use of such phosphodiesterase inhibitors when nitrosated or nitrosylated. Such toxicities and adverse effects include hypotension, syncope, as well as priapism. The smooth muscle relaxant properties of phosphodiesterase inhibitors and of compounds that donate, release or transfer nitrogen monoxide work together to permit the same efficacy with lower doses of the phosphodiesterase inhibitors.

Accordingly, in one aspect the invention provides novel nitrosated and nitrosylated phosphodiesrase inhibitors ($NO_n$-PDE inhibitor) wherein n is 1 or 2. The phosphodiesterase inhibitor can be nitrosylated or nitrosated through sites such as oxygen (hydroxyl condensation), sulfur (sulfhydryl condensation), carbon and nitrogen. The invention also provides compositions comprising such compounds in a pharmaceutically acceptable carrier.

In another aspect the invention provides a composition comprising a therapeutically effective amount of an phosphodiesterase inhibitor (PDE inhibitor), which can optionally be substituted with at least one NO or $NO_2$ moiety, and one to ten fold molar excess of a compound that donates, transfers or releases nitrogen monoxide as a charged species, i.e., nitrosonium ($NO^+$) or nitroxyl ($NO^-$), or as the neutral species, nitric oxide (NO.). The invention also provides compositions comprising such compounds in a pharmaceutically acceptable carrier.

In another aspect, the invention provides a method for treating male impotence in humans which comprises administering to an individual in need thereof a therapeutically effective amount of a nitrosated or nitrosylated PDE inhibitor.

In another aspect, the invention provides a method for treating male impotence in humans which comprises administering to an individual in need thereof a composition comprising a therapeutically effective amount of an PDE inhibitor which can optionally be substituted with at least one NO or $NO_2$ moiety, and a compound that donates. transfers or releases nitric oxide as a charged species, i.e., nitrosonium ($NO^+$) or nitroxyl ($NO^-$), or as the neutral species, nitric oxide (NO.). The PDE inhibitor or PDE inhibitor directly or indirectly linked to at least one NO or $NO_2$ group, and nitric oxide donor can be administered separately or as components of the same composition.

In another aspect, the invention provides a method for treating female sexual dysfunction in humans which comprises administering to an individual in need thereof a therapeutically effective amount of a nitrosated or nitrosylated PDE inhibitor.

In another aspect, the invention provides a method for treating treating female sexual dysfunction in humans which comprises administering to an individual in need thereof a composition comprising a therapeutically effective amount of an PDE inhibitor which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO.). The PDE inhibitor or PDE inhibitor directly or indirectly linked to at least one NO or $NO_2$ group, and nitric oxide donor can be administered separately or as components of the same composition.

In another aspect, the invention provides a method for treating anal disease resulting from excessive anal sphincter tone in humans which comprises administering to an individual in need thereof a therapeutically effective amount of a nitrosated or nitrosylated PDE inhibitor.

In another aspect, the invention provides a method for treating treating anal disease resulting from excessive anal sphincter tone in humans which comprises administering to an individual in need thereof a composition comprising a therapeutically effective amount of an PDE inhibitor which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO.). The PDE inhibitor or PDE inhibitor directly or indirectly linked to at least one NO or $NO_2$ group, and nitric oxide donor can be administered separately or as components of the same composition.

The nitrosated or nitrosylated PDE inhibitor and the compound that donates, transfers or releases nitric oxide and/or stimulates endogenous production of NO or EDRF in vivo can be administered separately or as components of the same composition in one or more pharmaceutically acceptable carriers.

The following drawings are illustrative of embodiments of the invention and do not limit the scope of the invention as defined by the claims.

Figure 2:
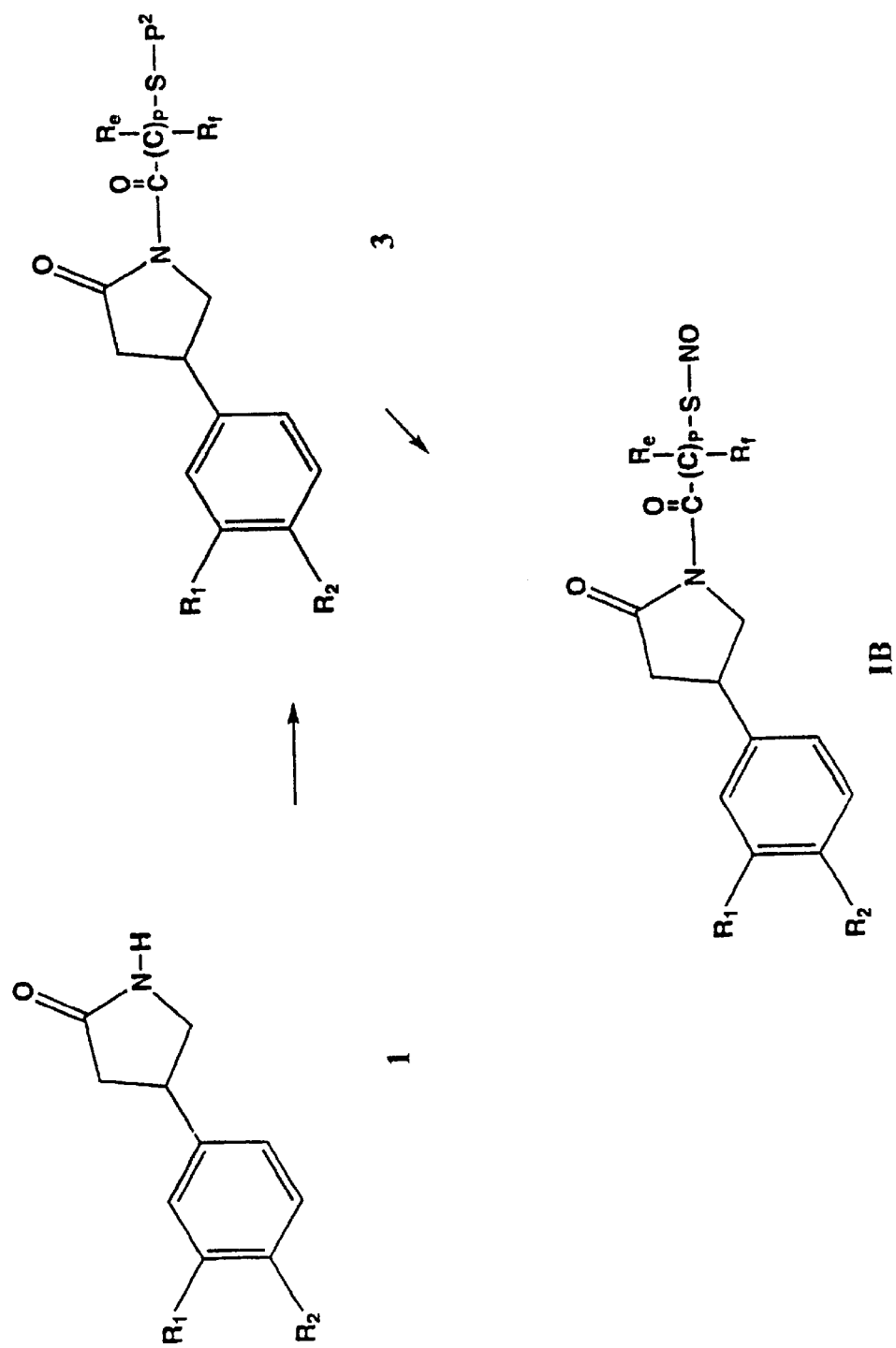
Figure 3:
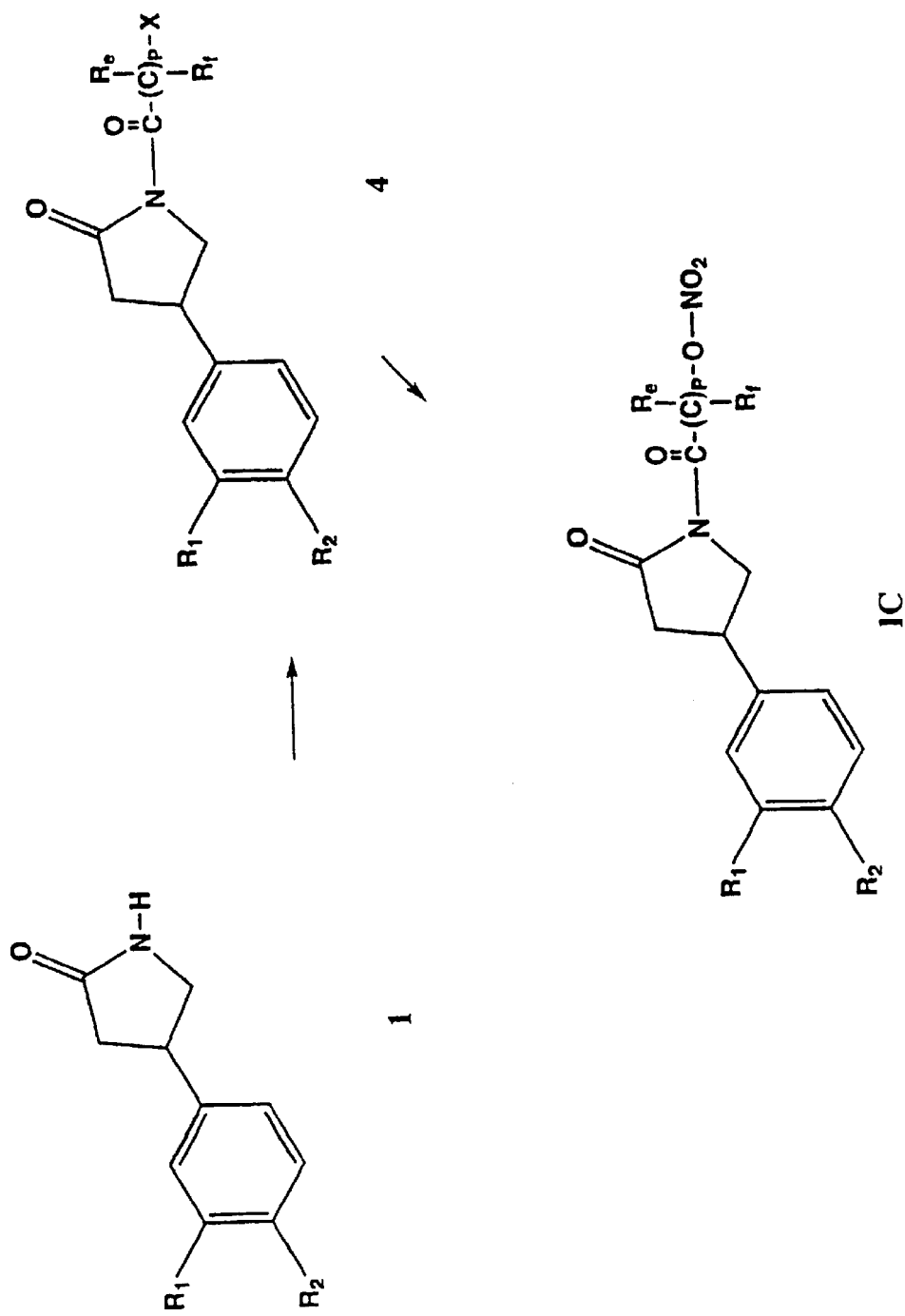
Figure 4:
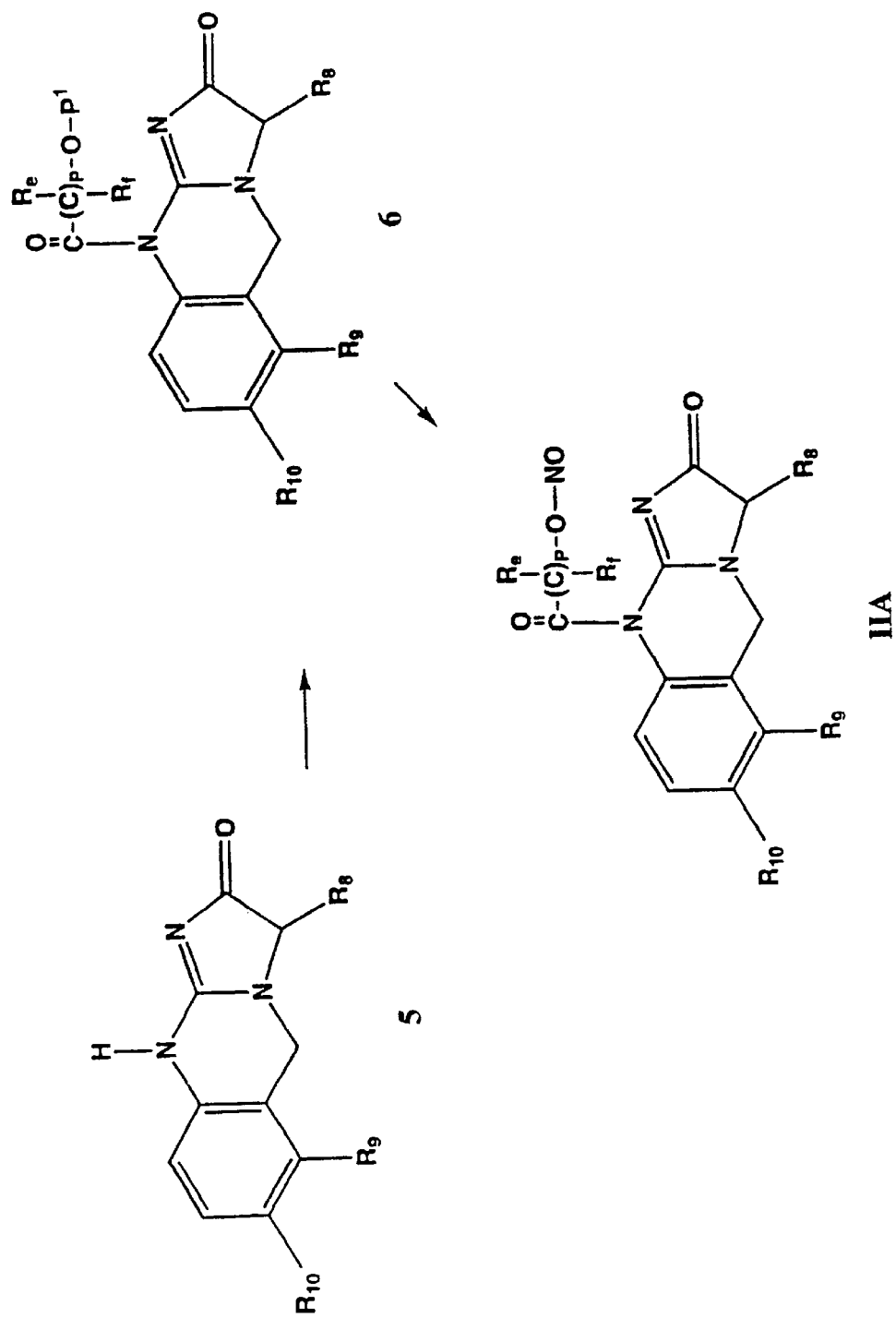
Figure 5:
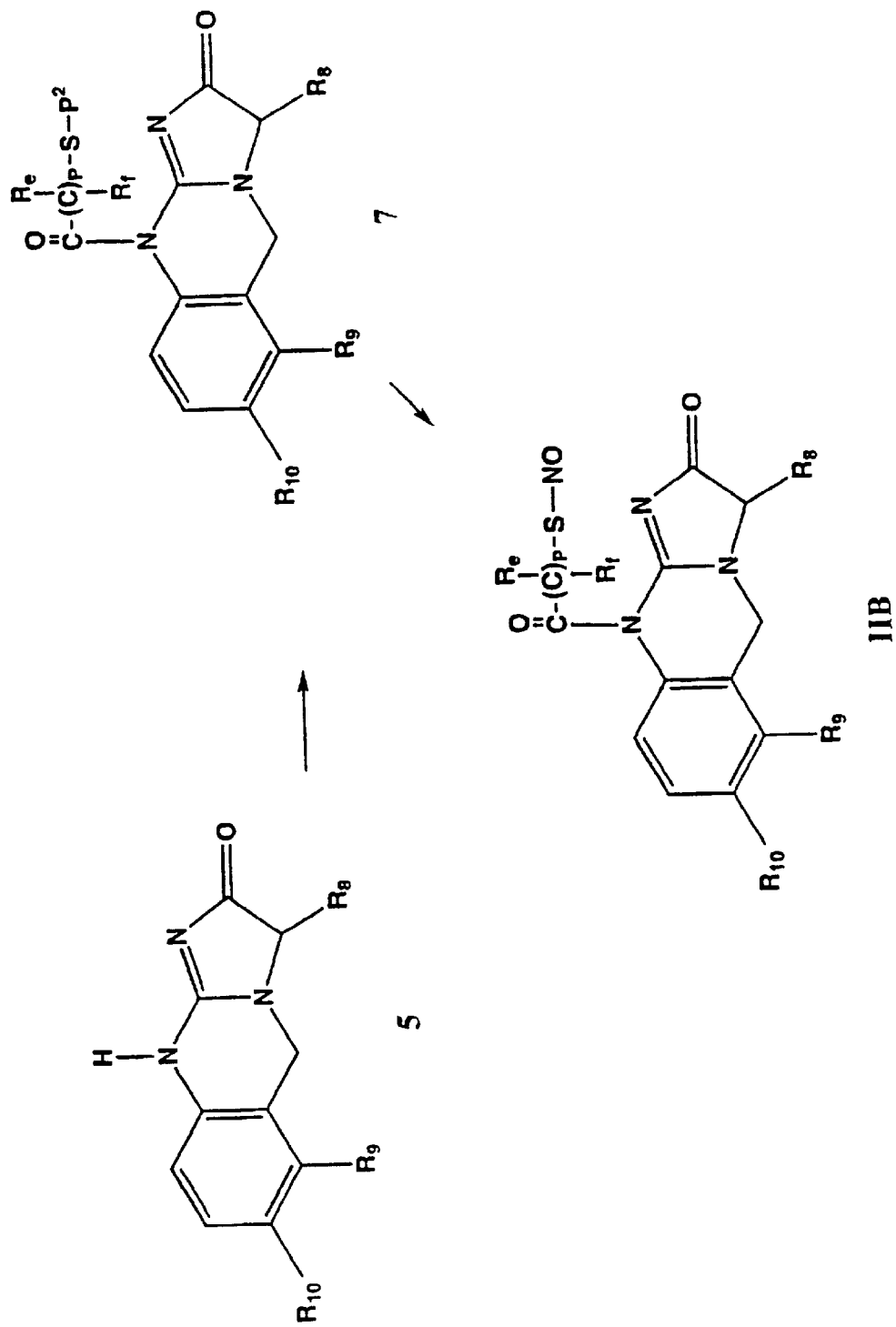
Figure 6:
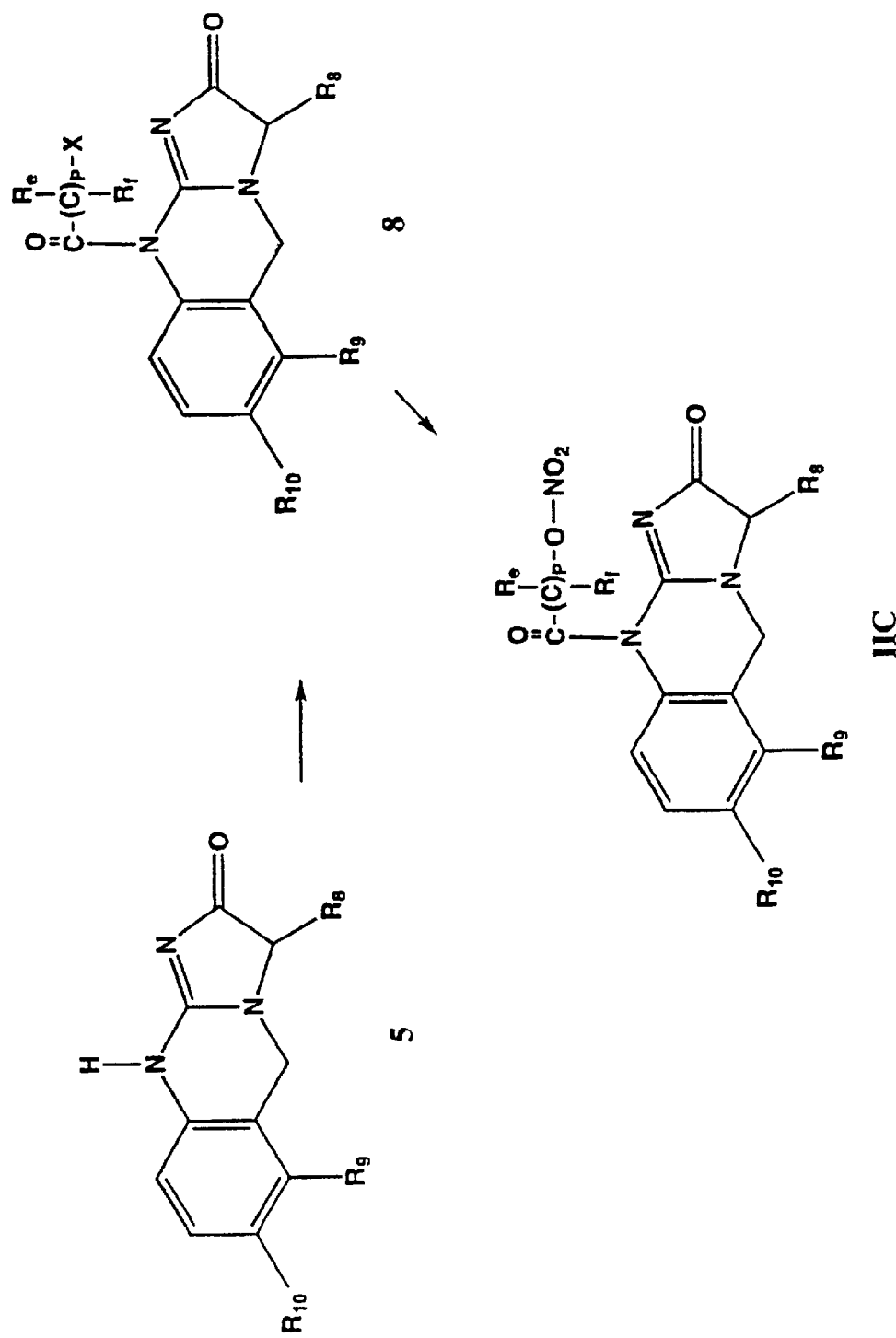
Figure 7:
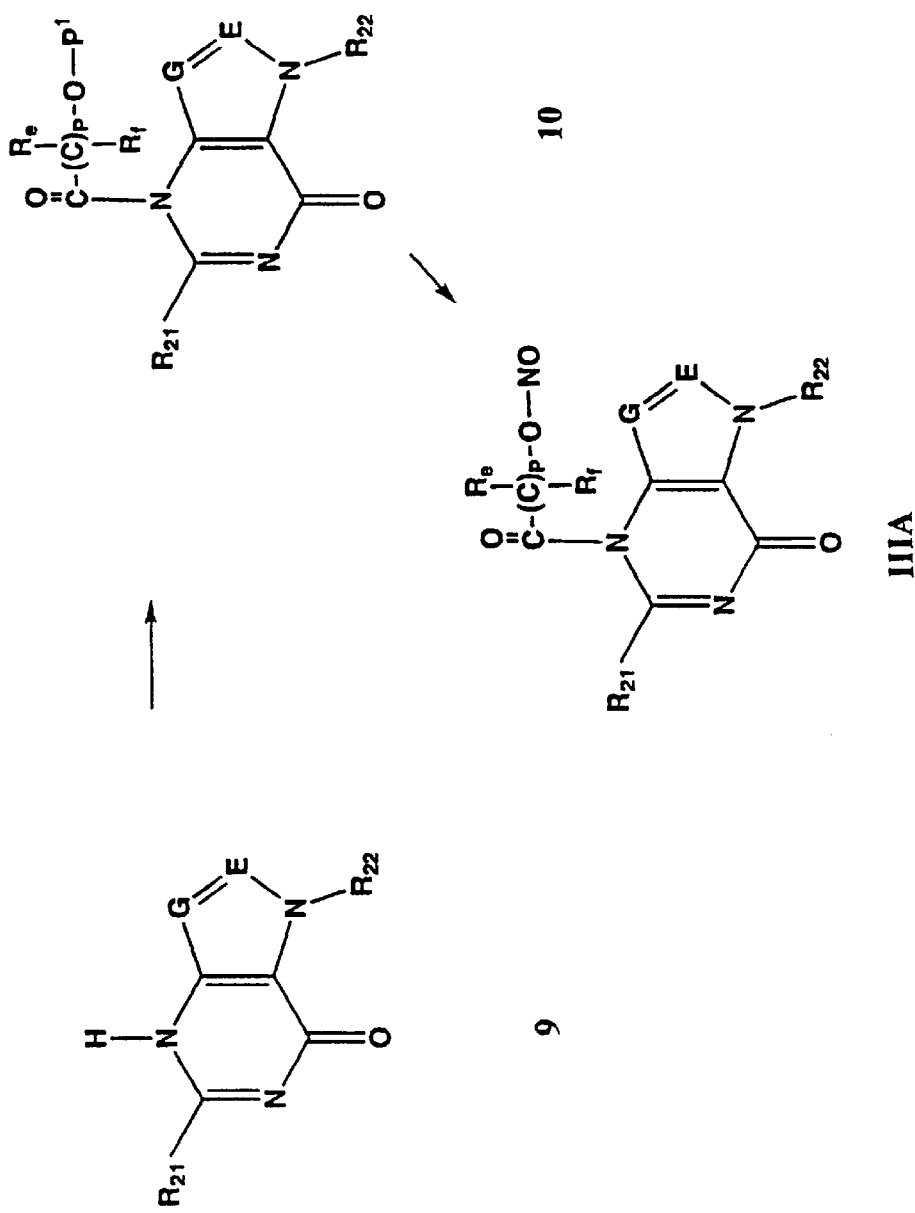
Figure 8:
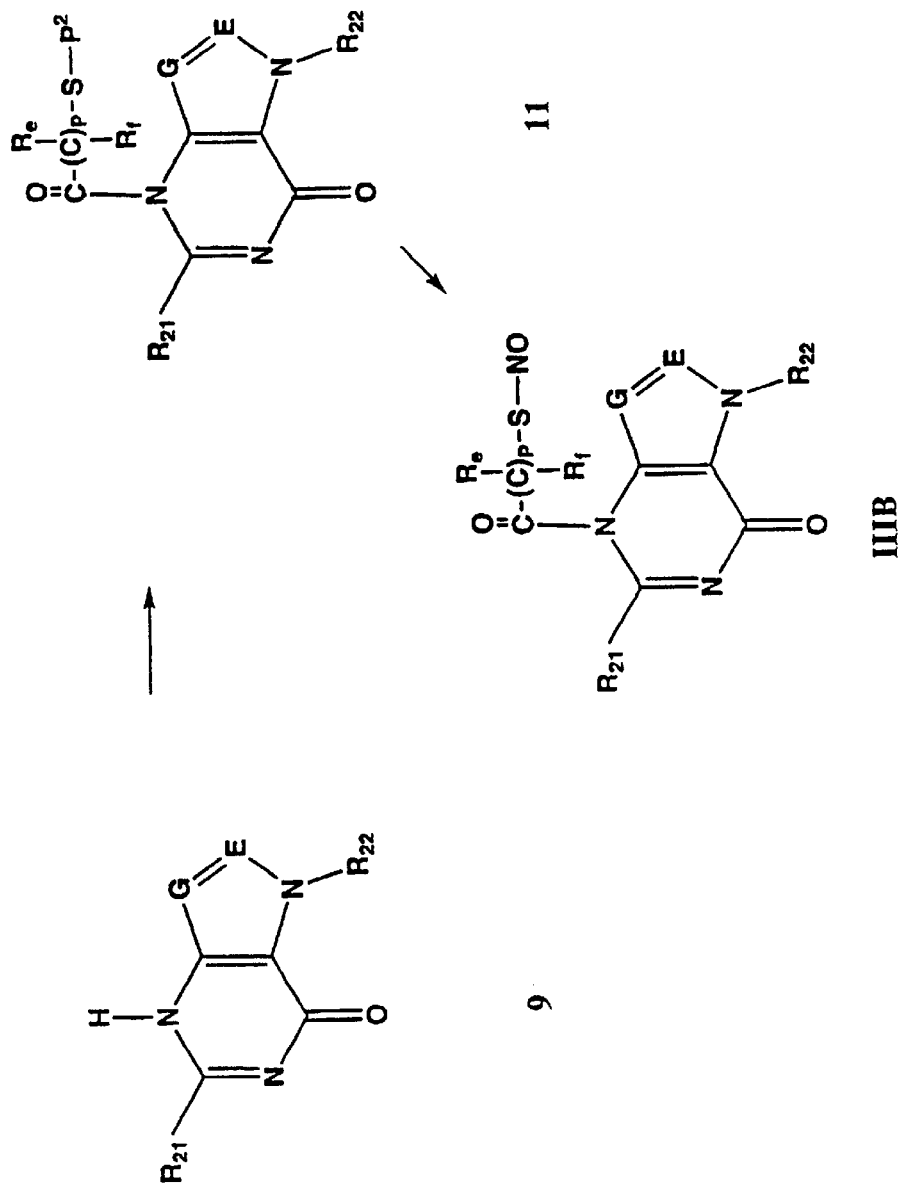
Figure 9:
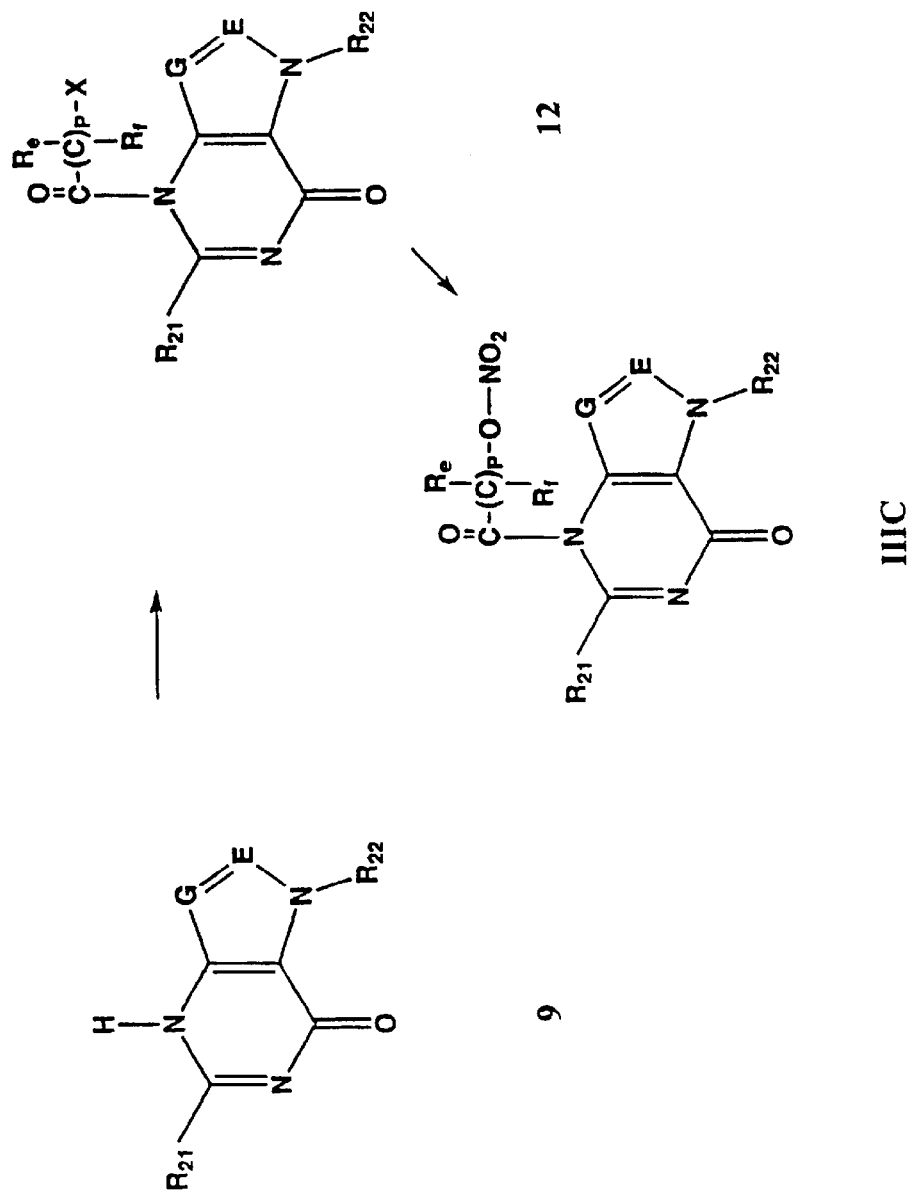
Figure 10:
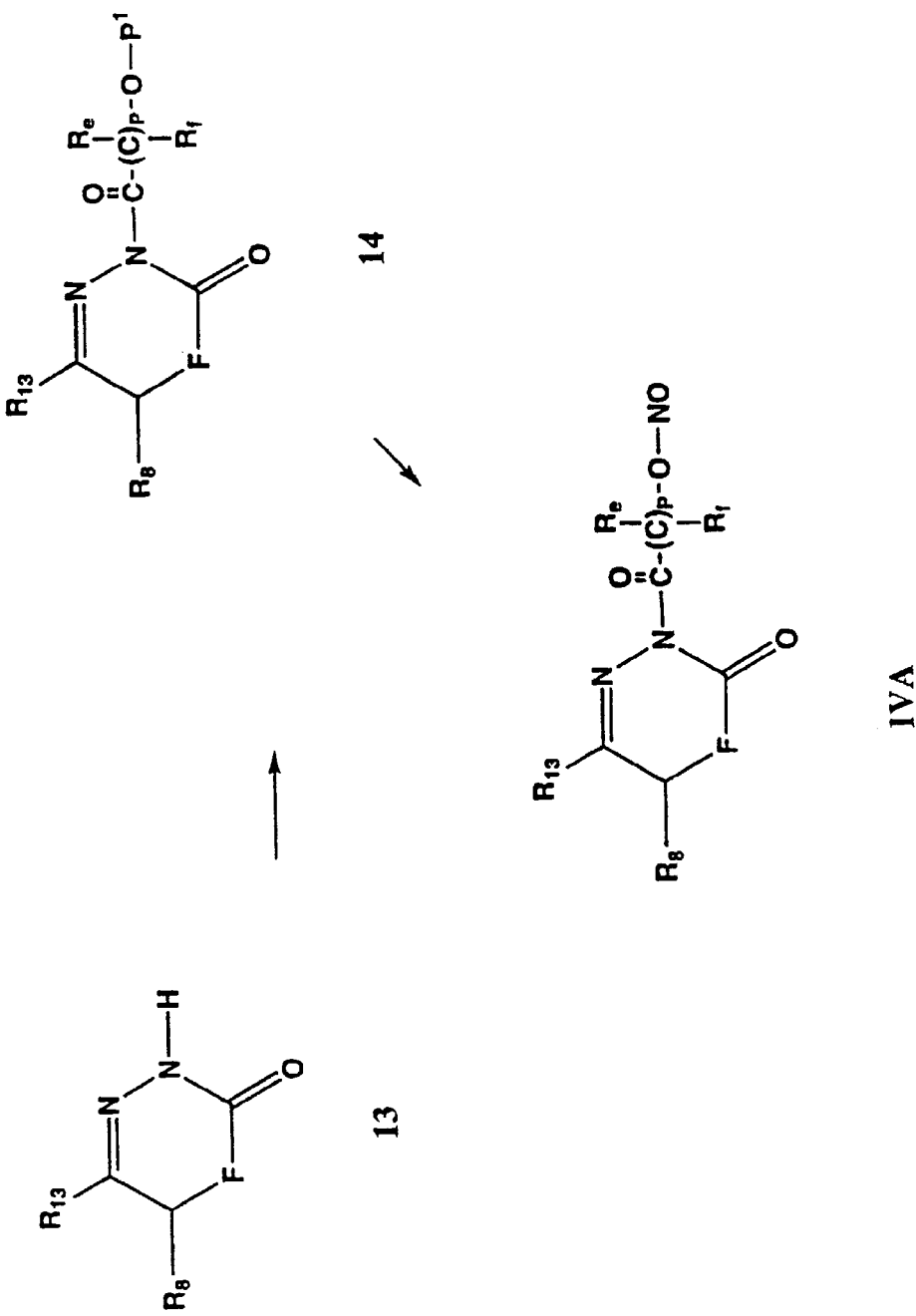
Figure 11:
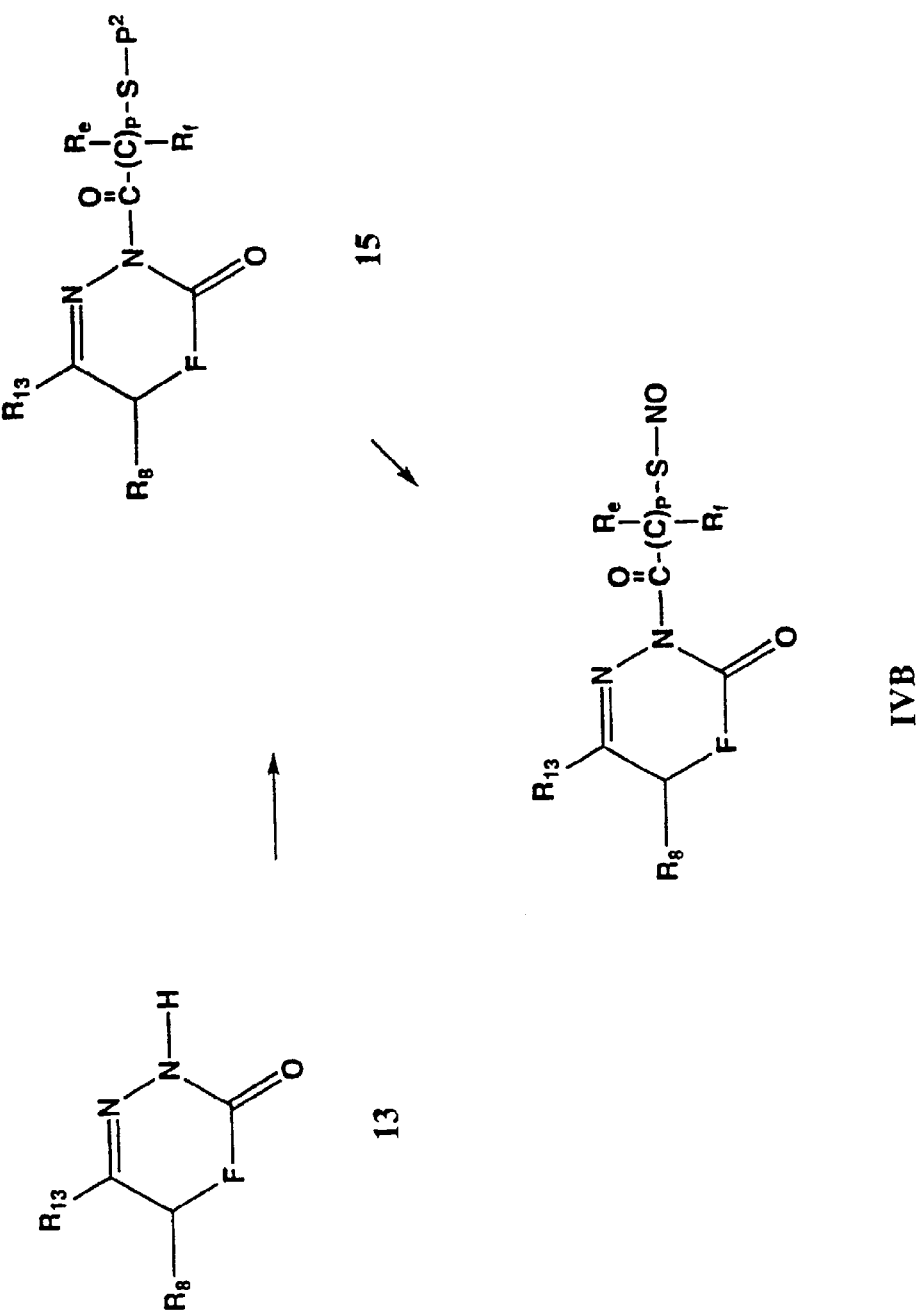
Figure 12:
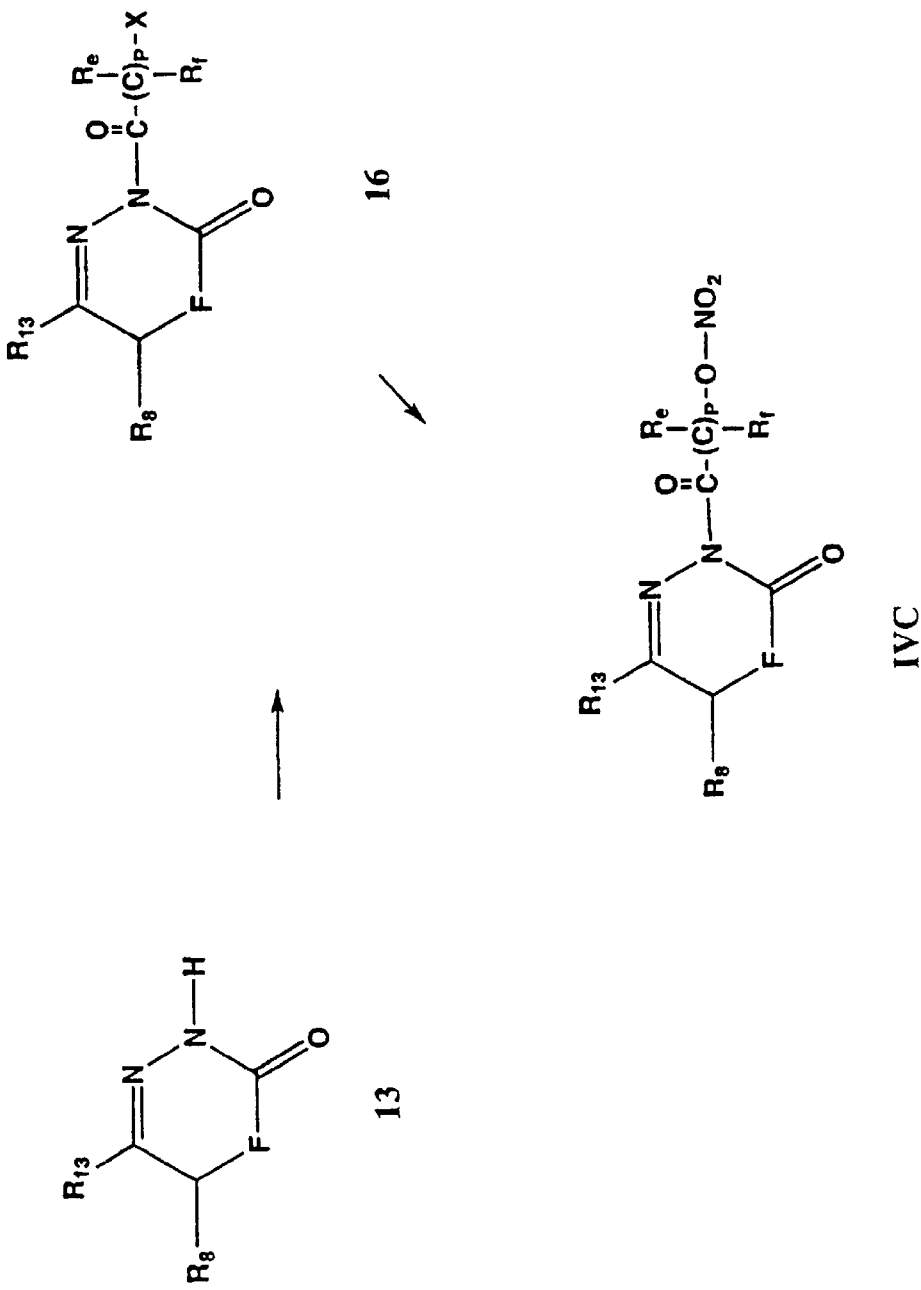
Figure 13:
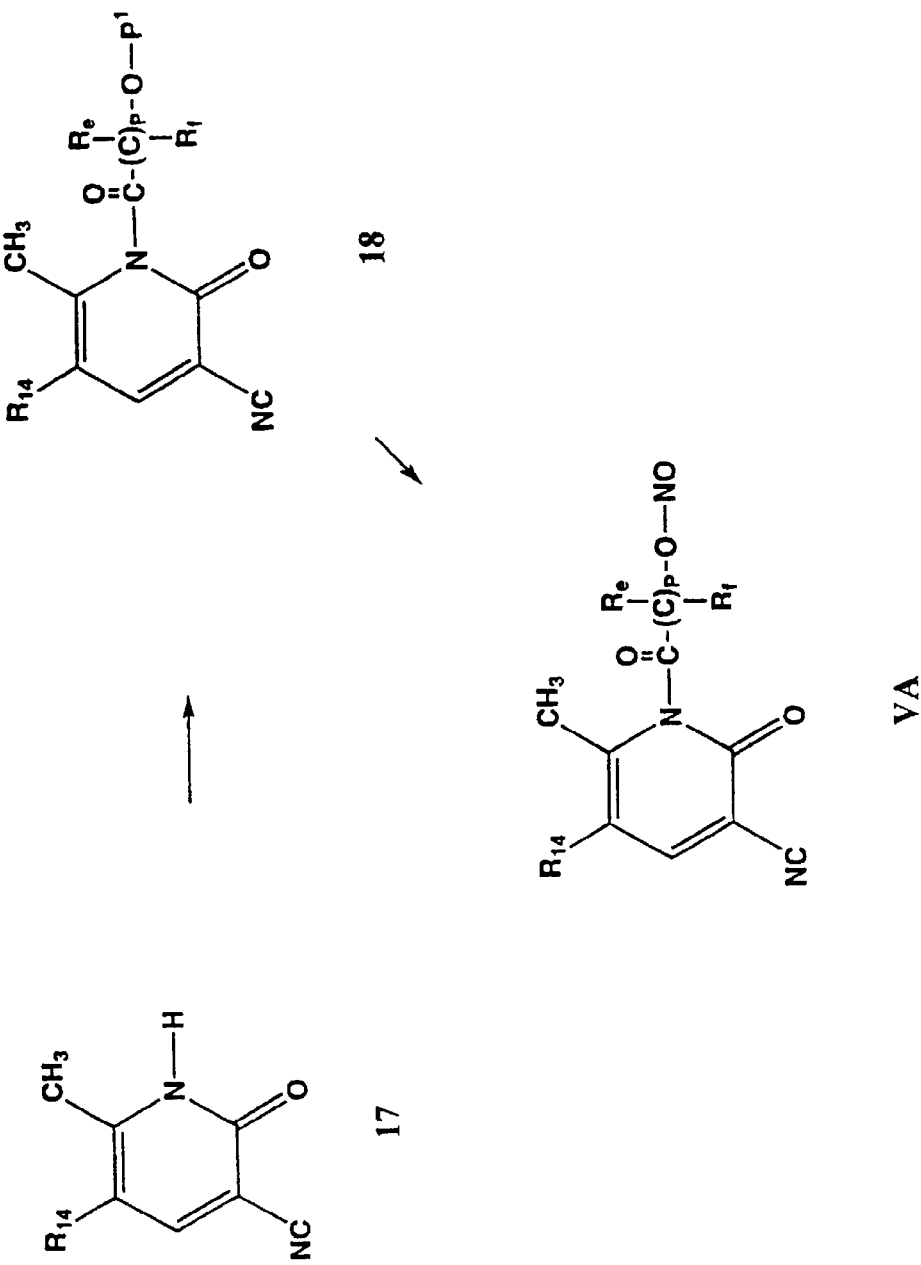
Figure 14:
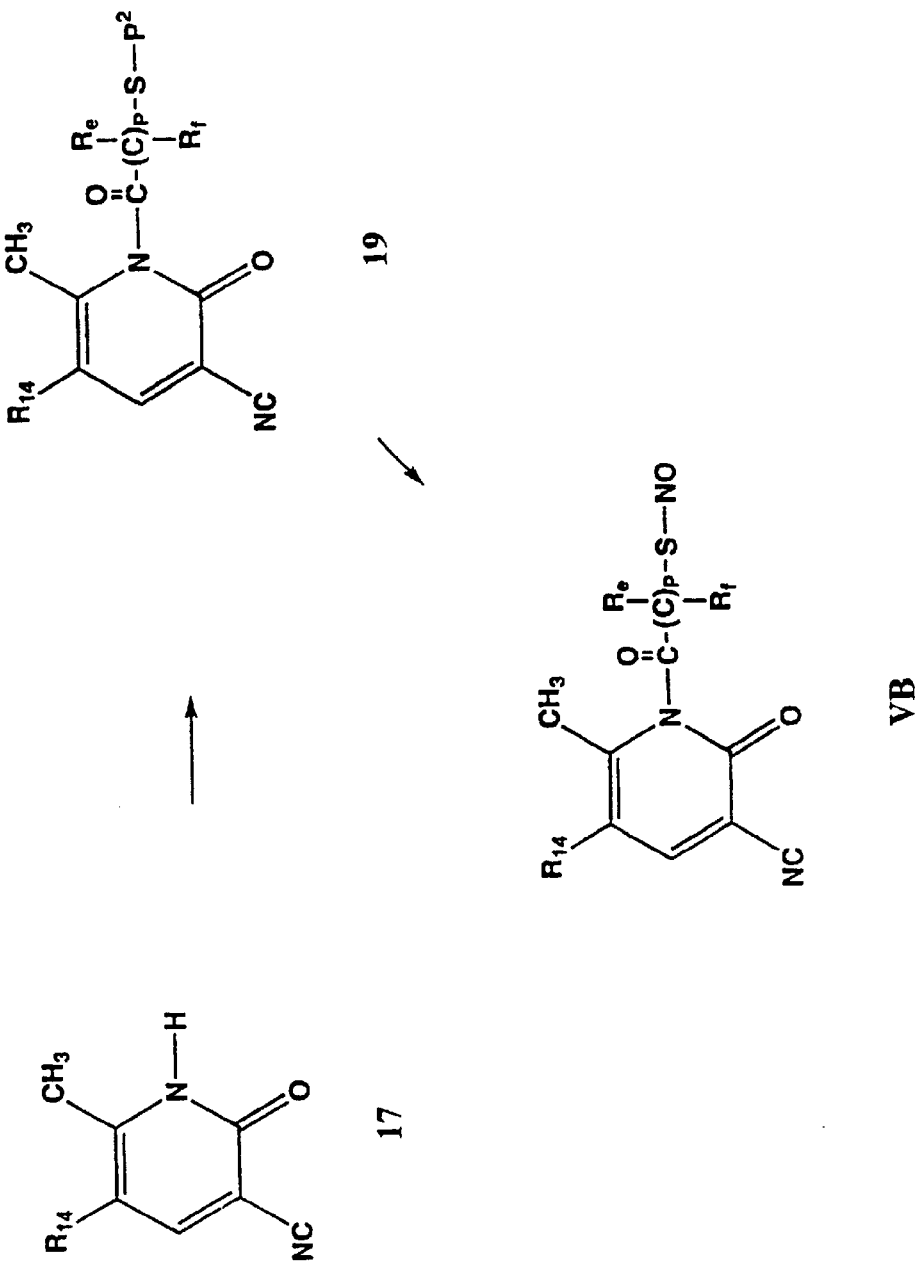
Figure 15:
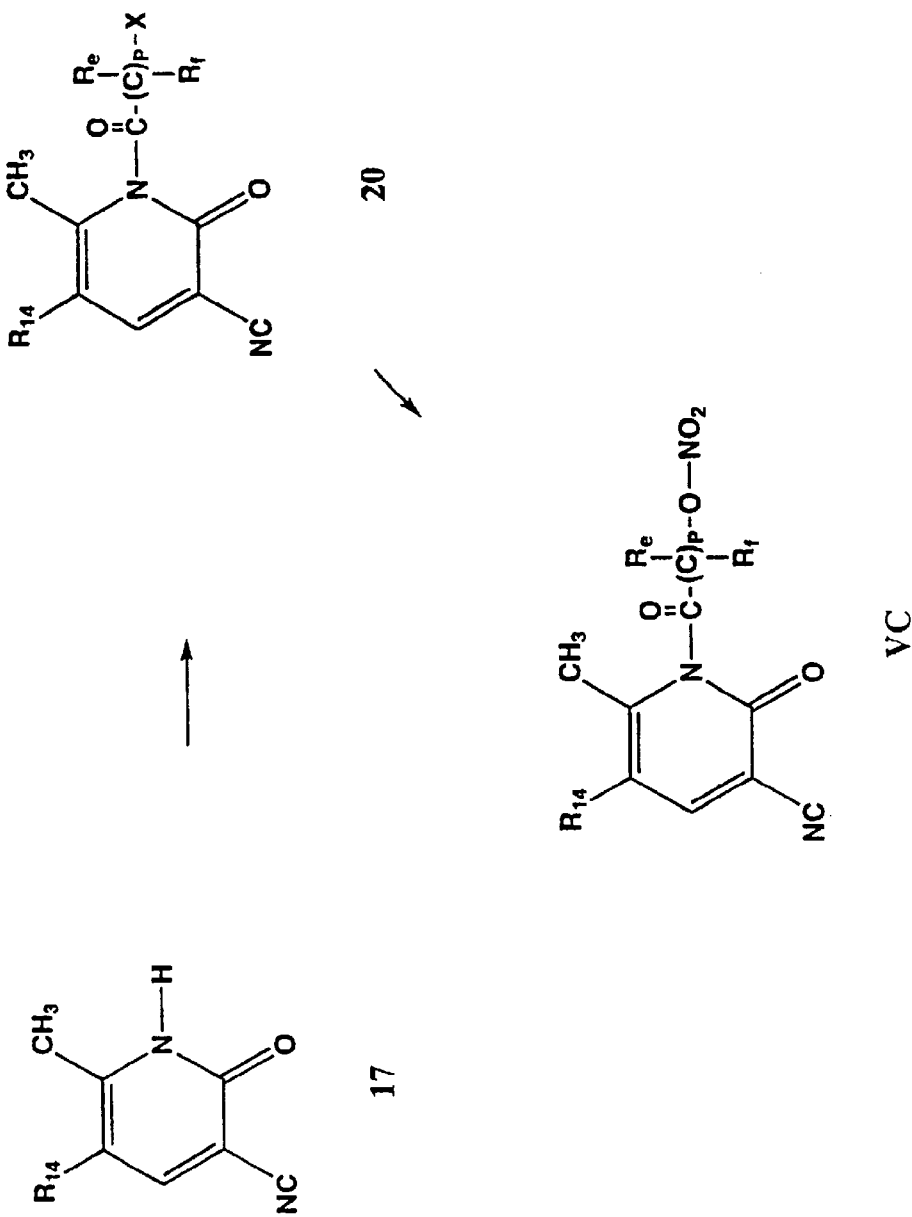
Figure 16:
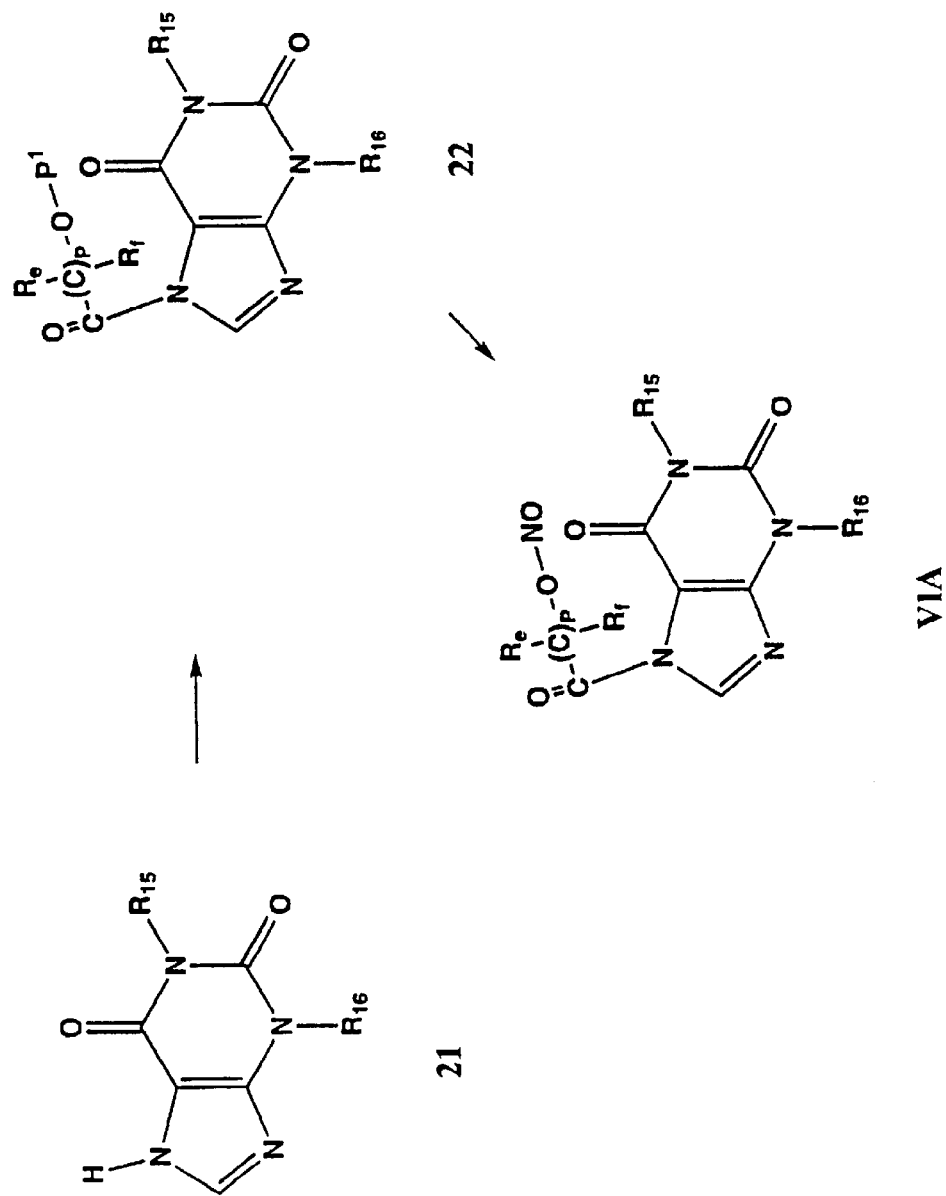
Figure 17:
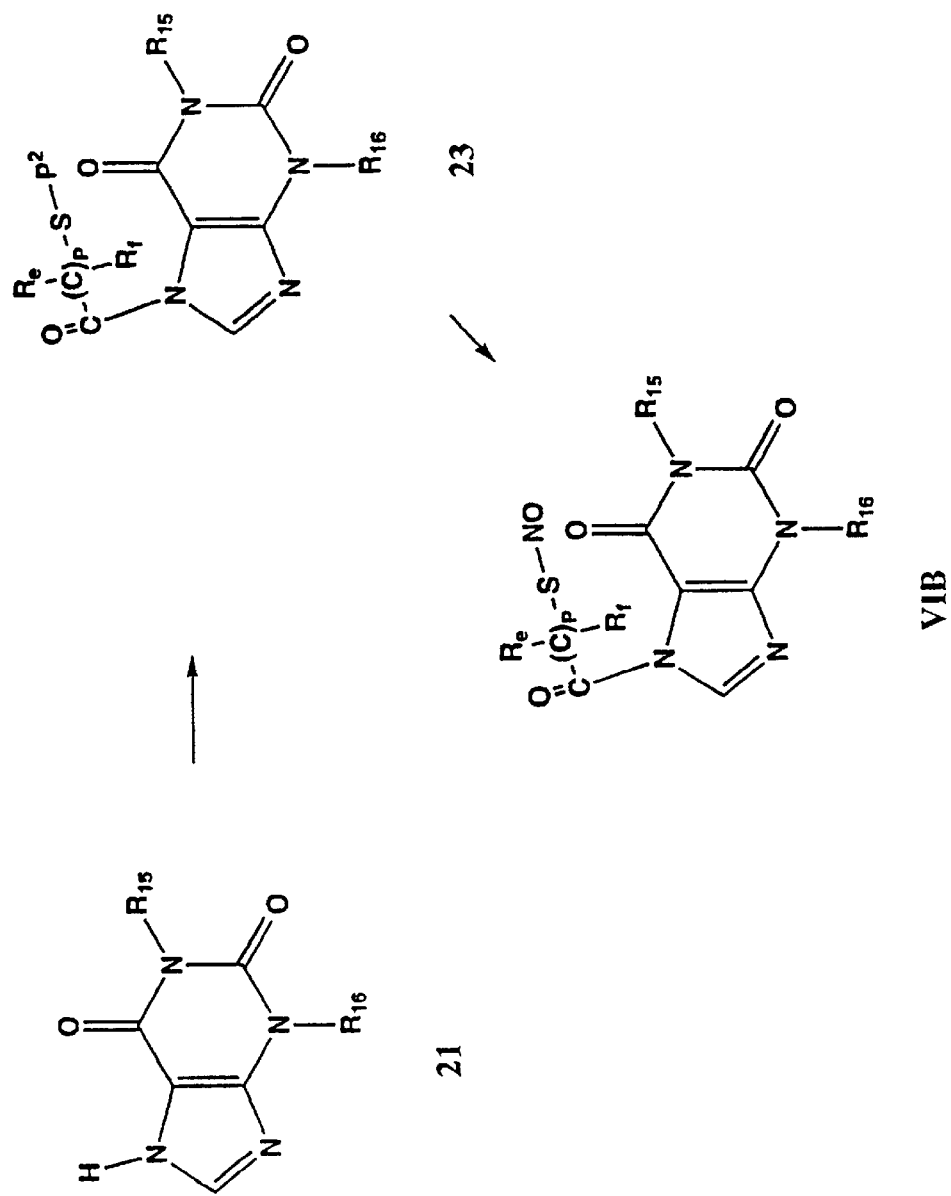
Figure 18:
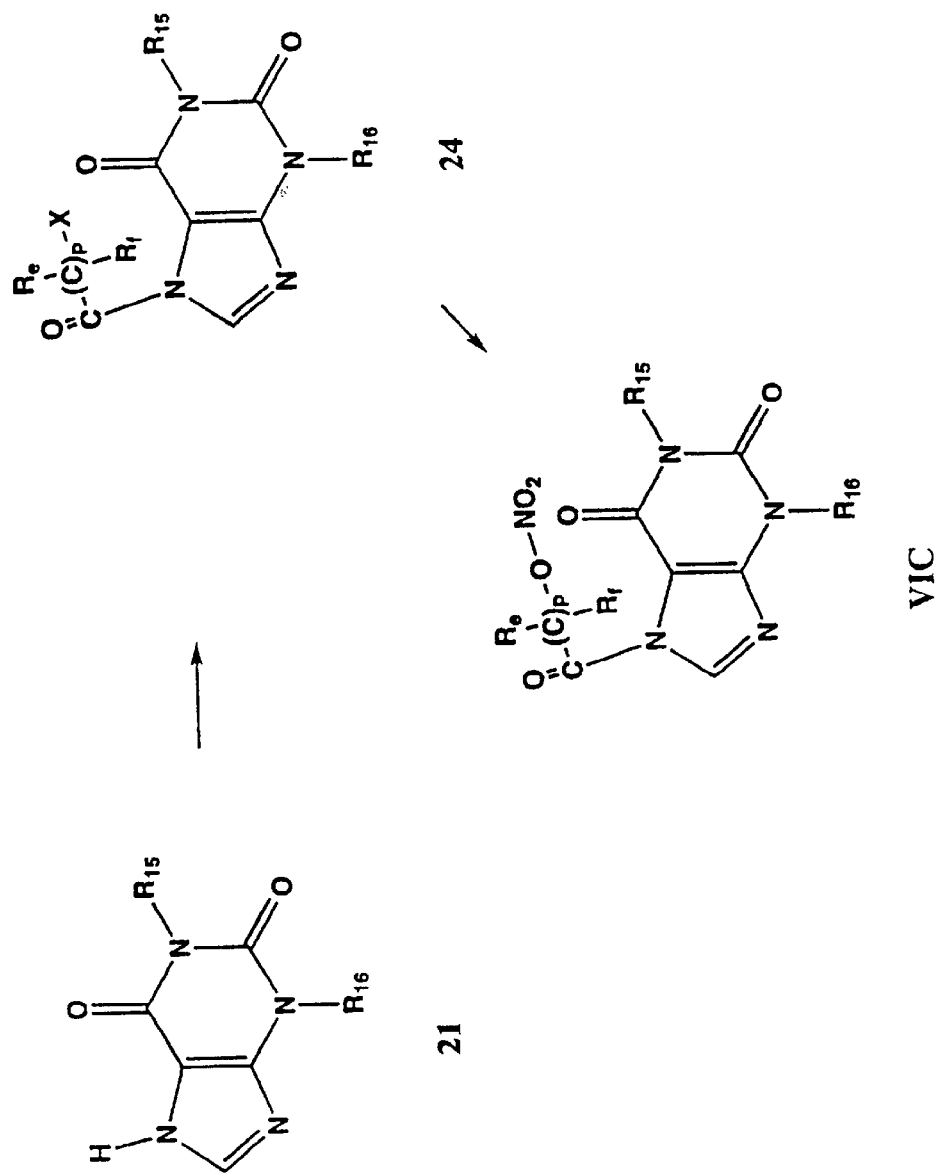
Figure 19:
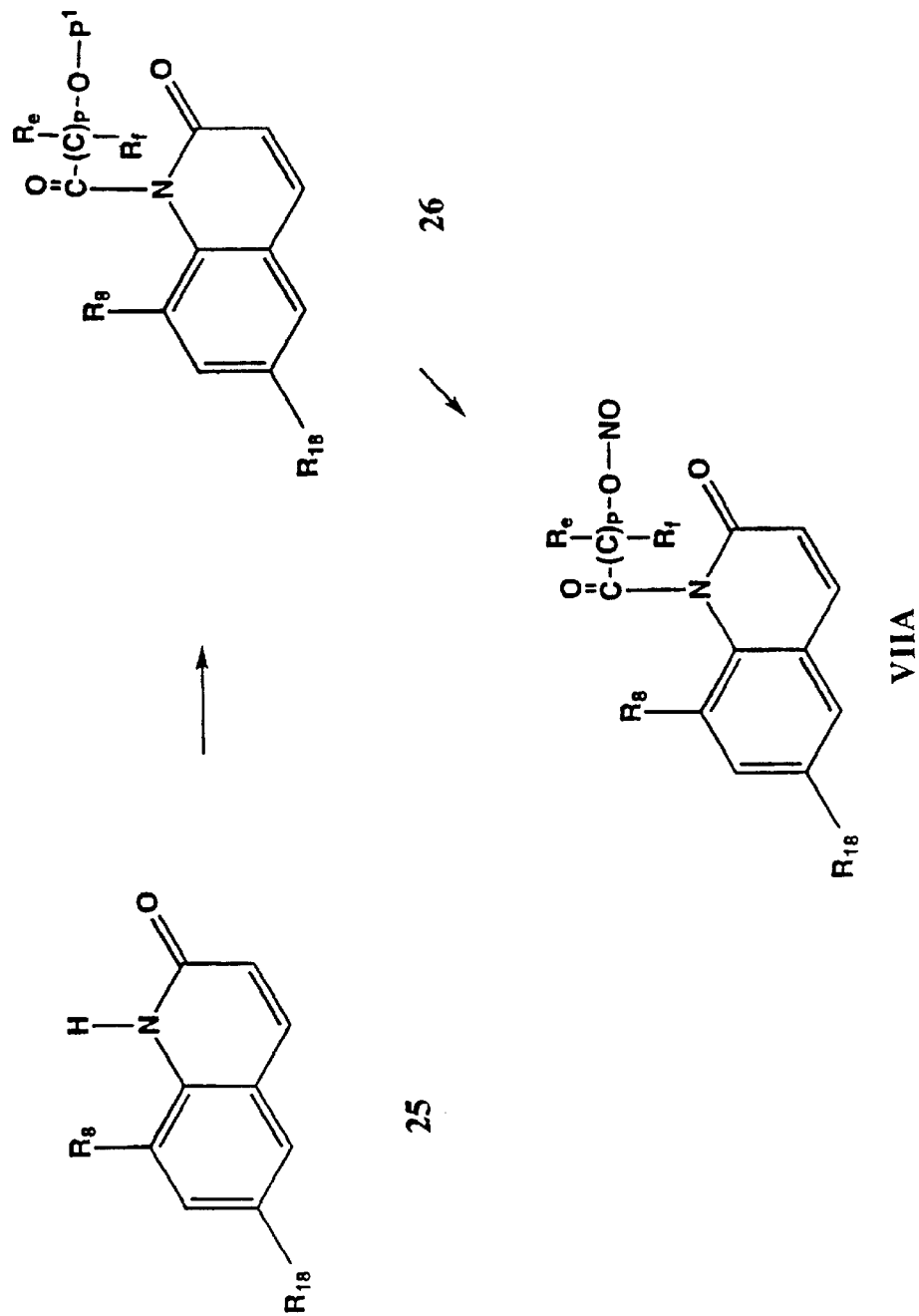
Figure 20:
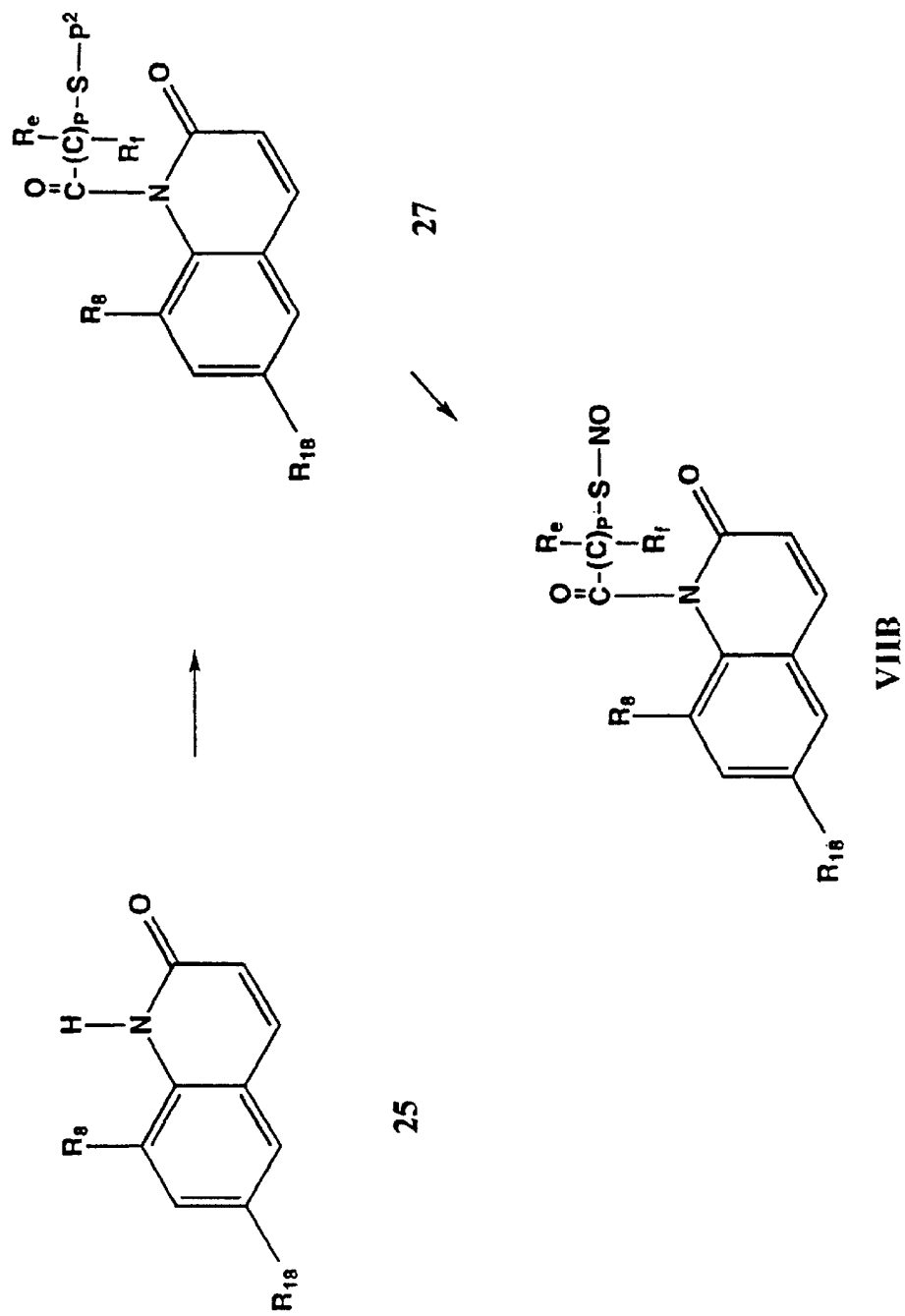
Figure 21:
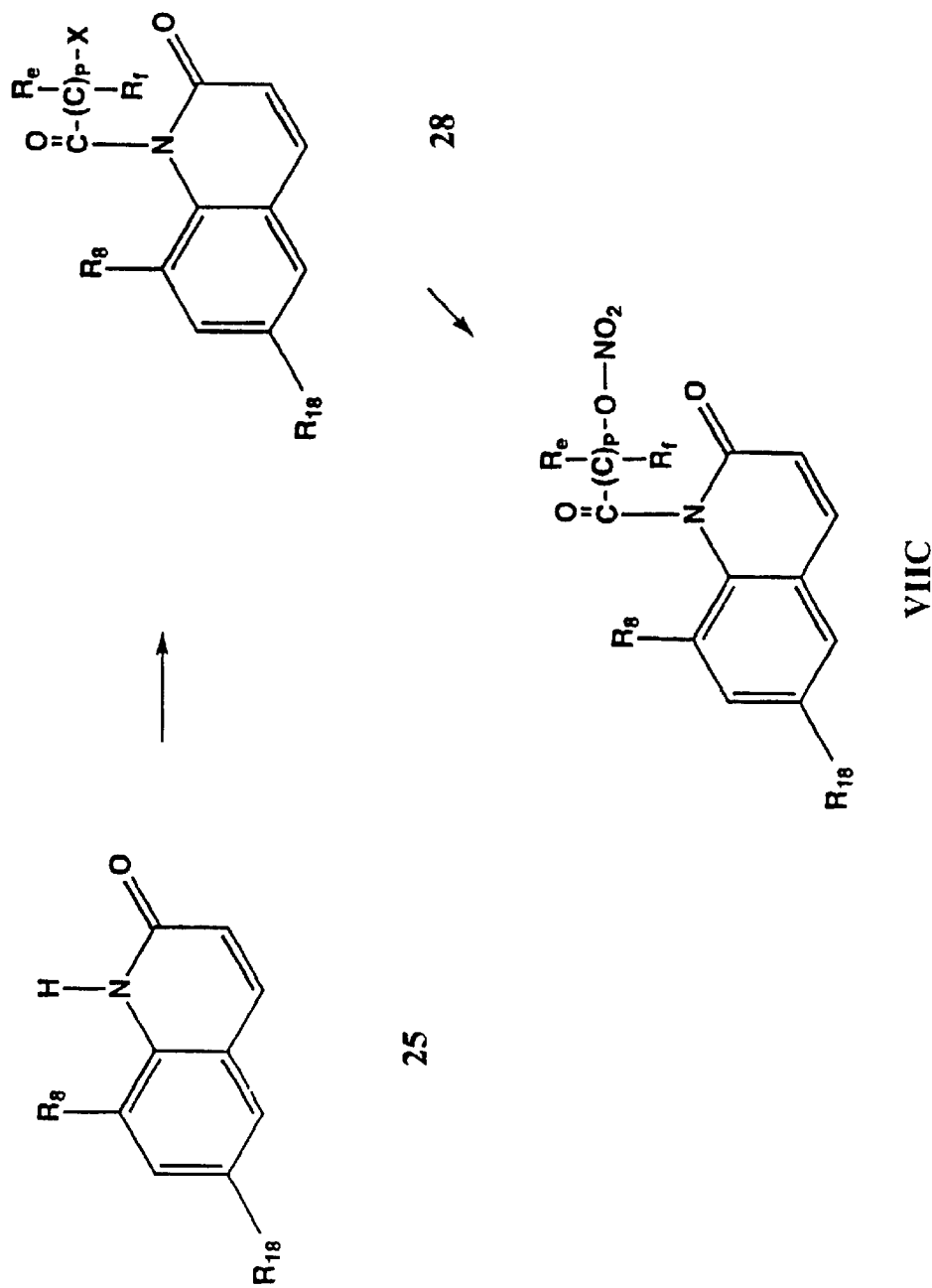
Figure 22:
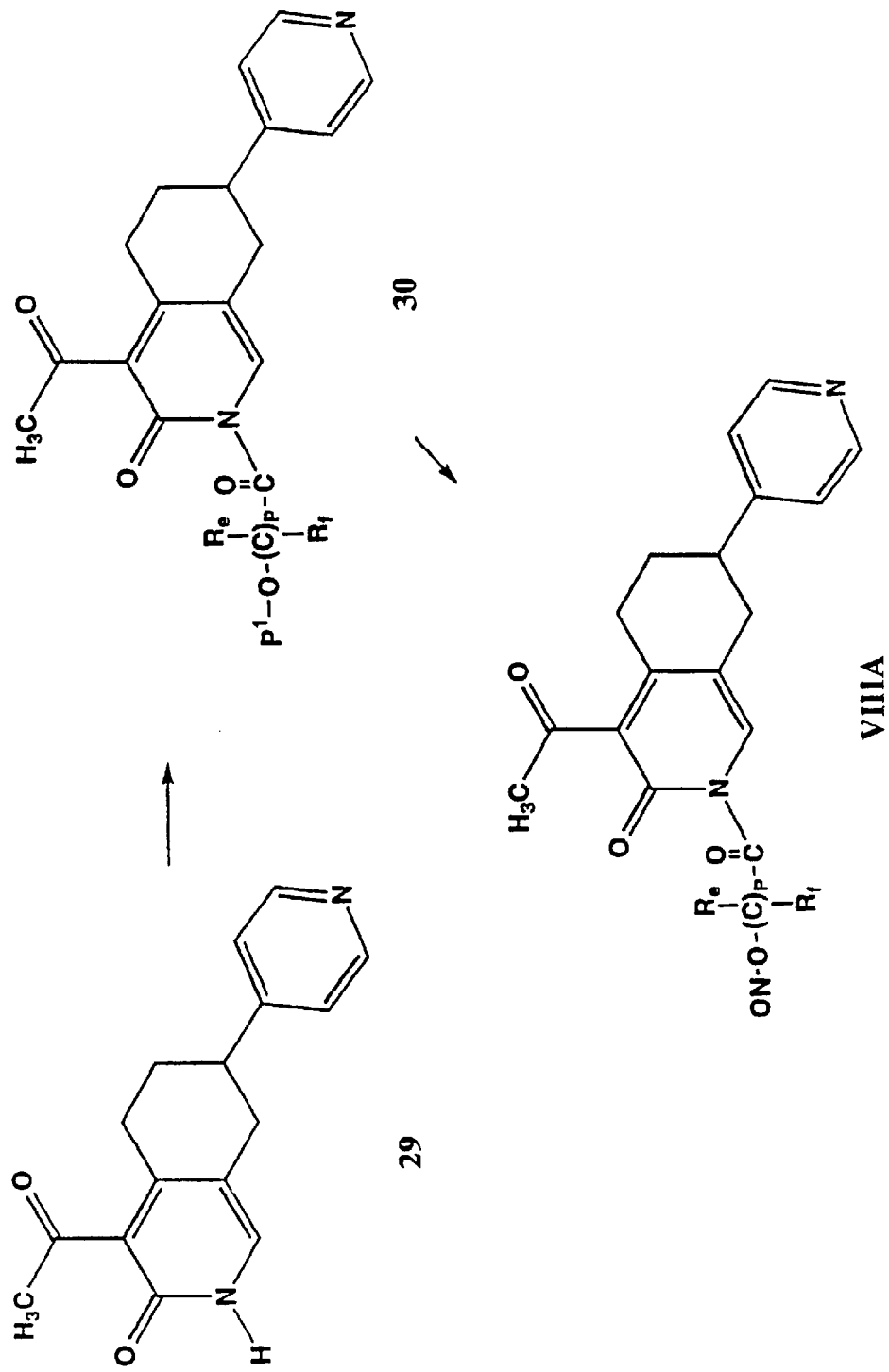
Figure 23:
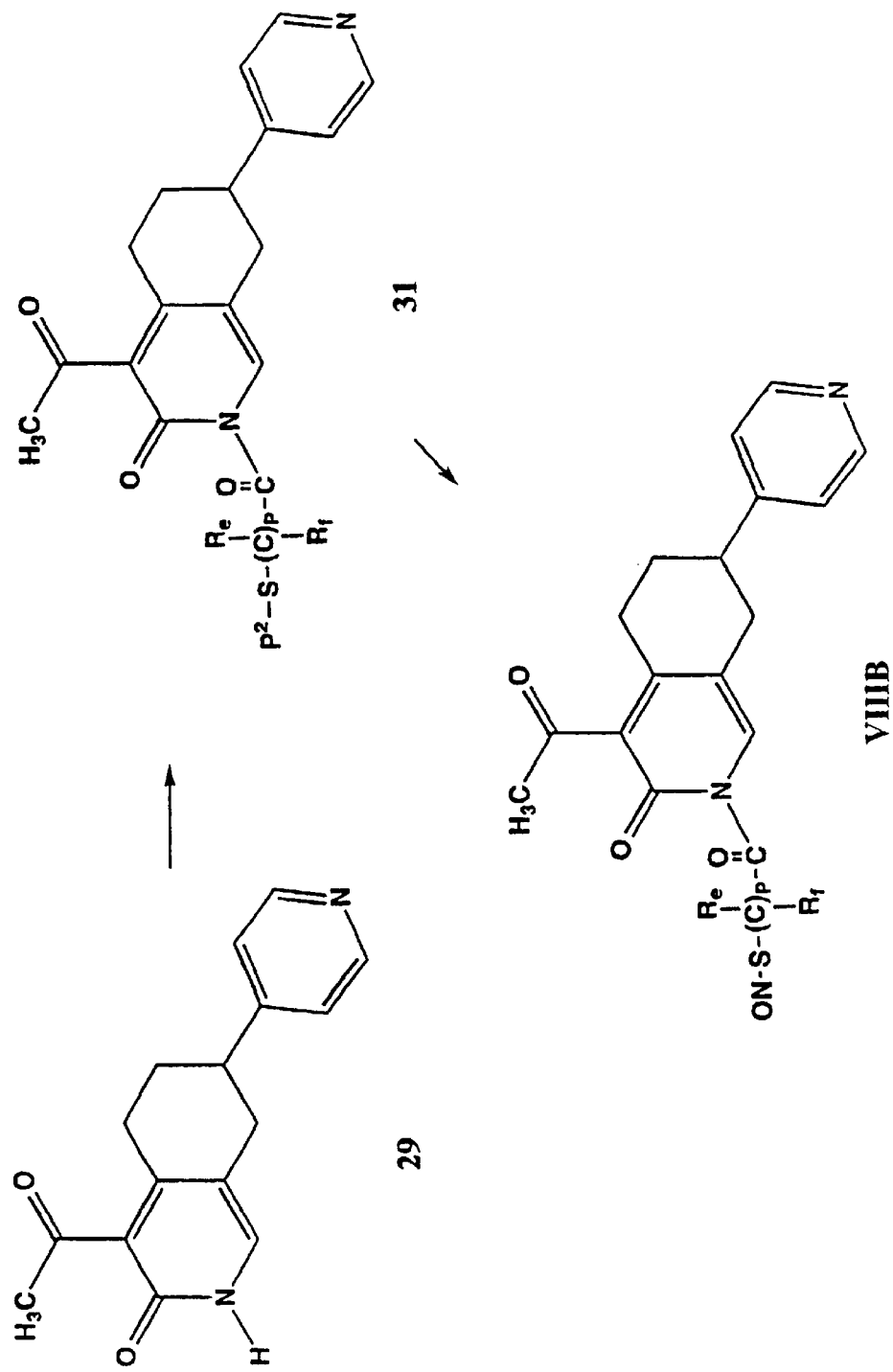
Figure 24:
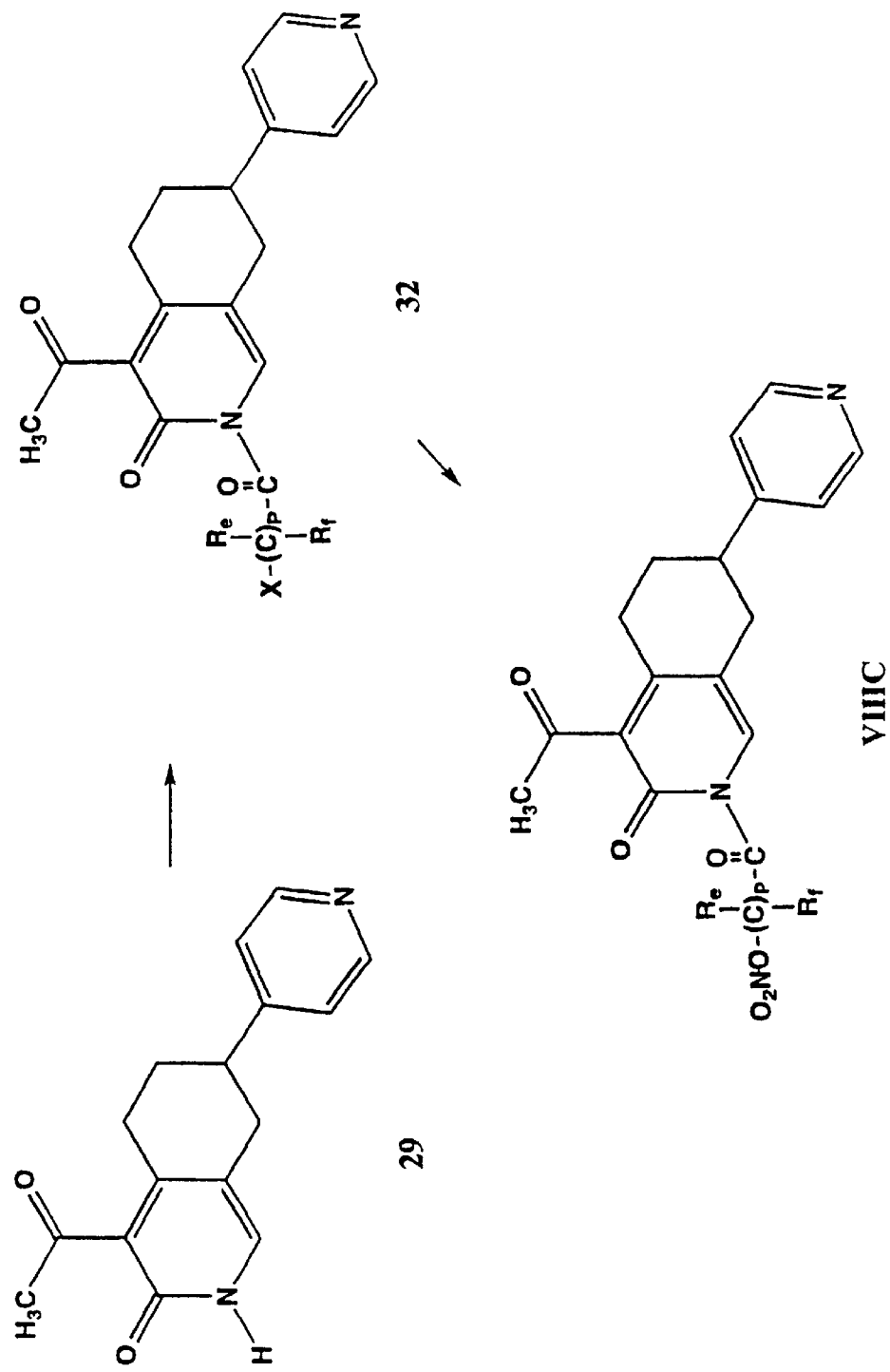
Figure 25:
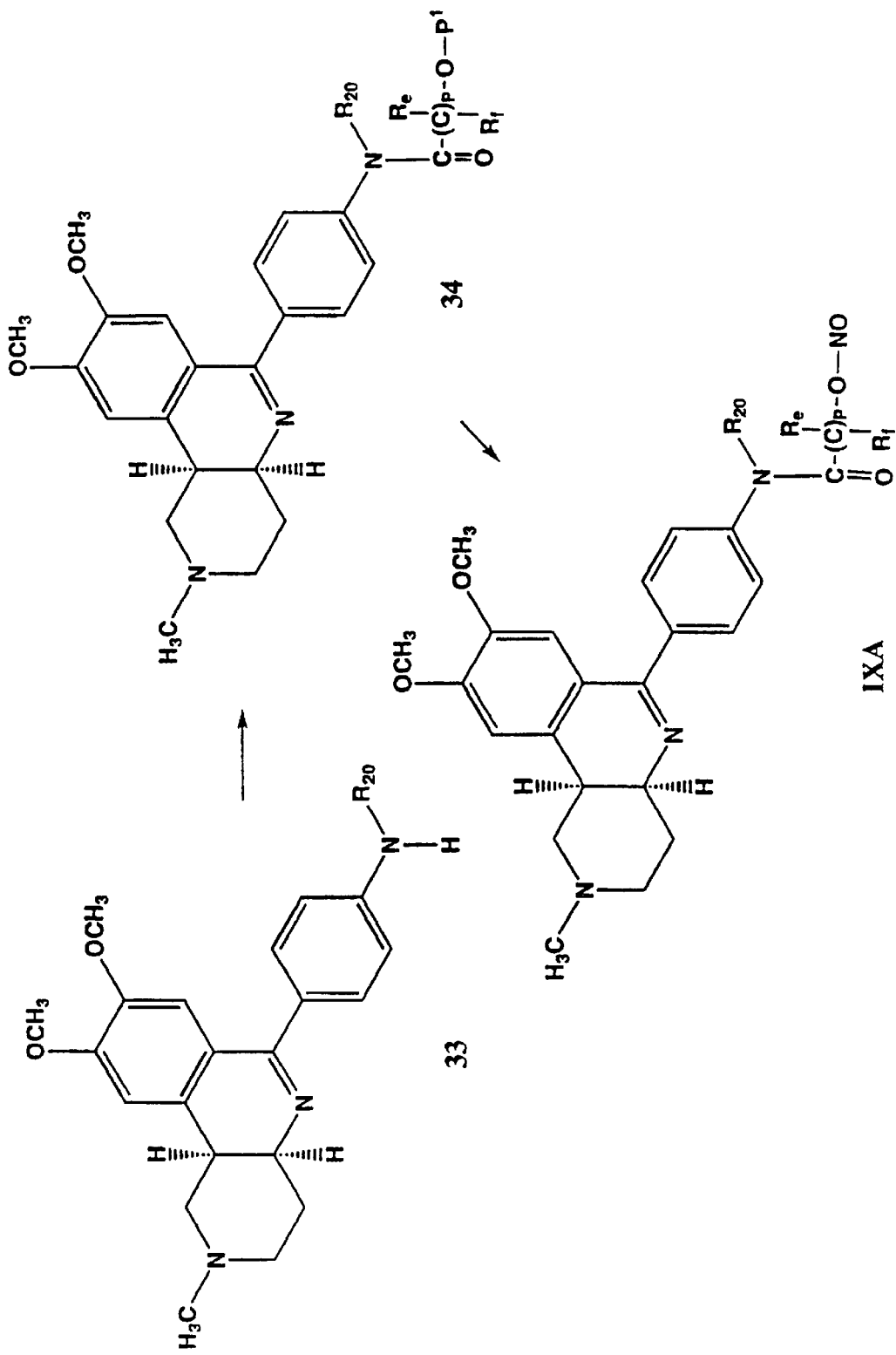
Figure 26:
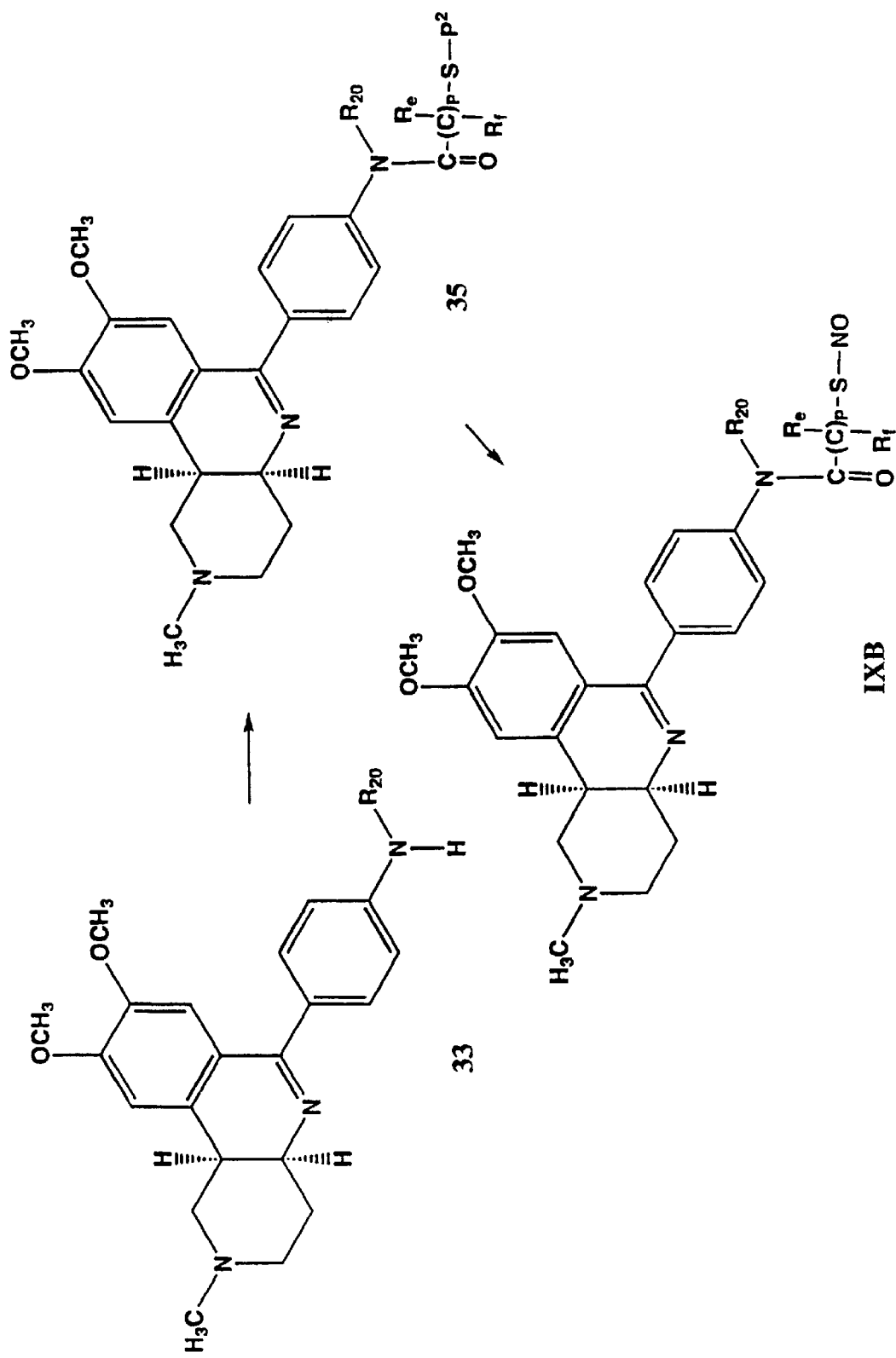
Figure 27:
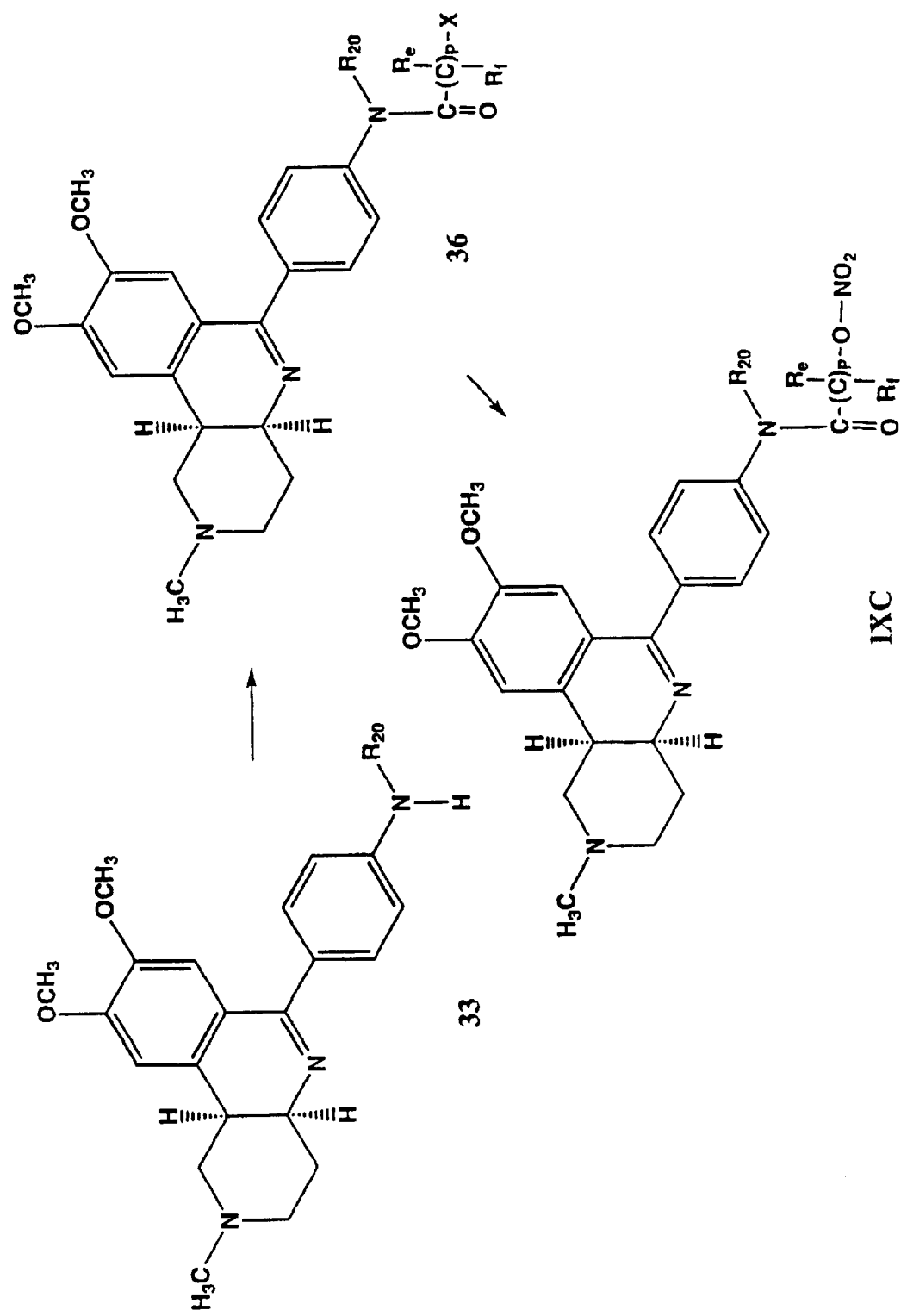
Figure 28:
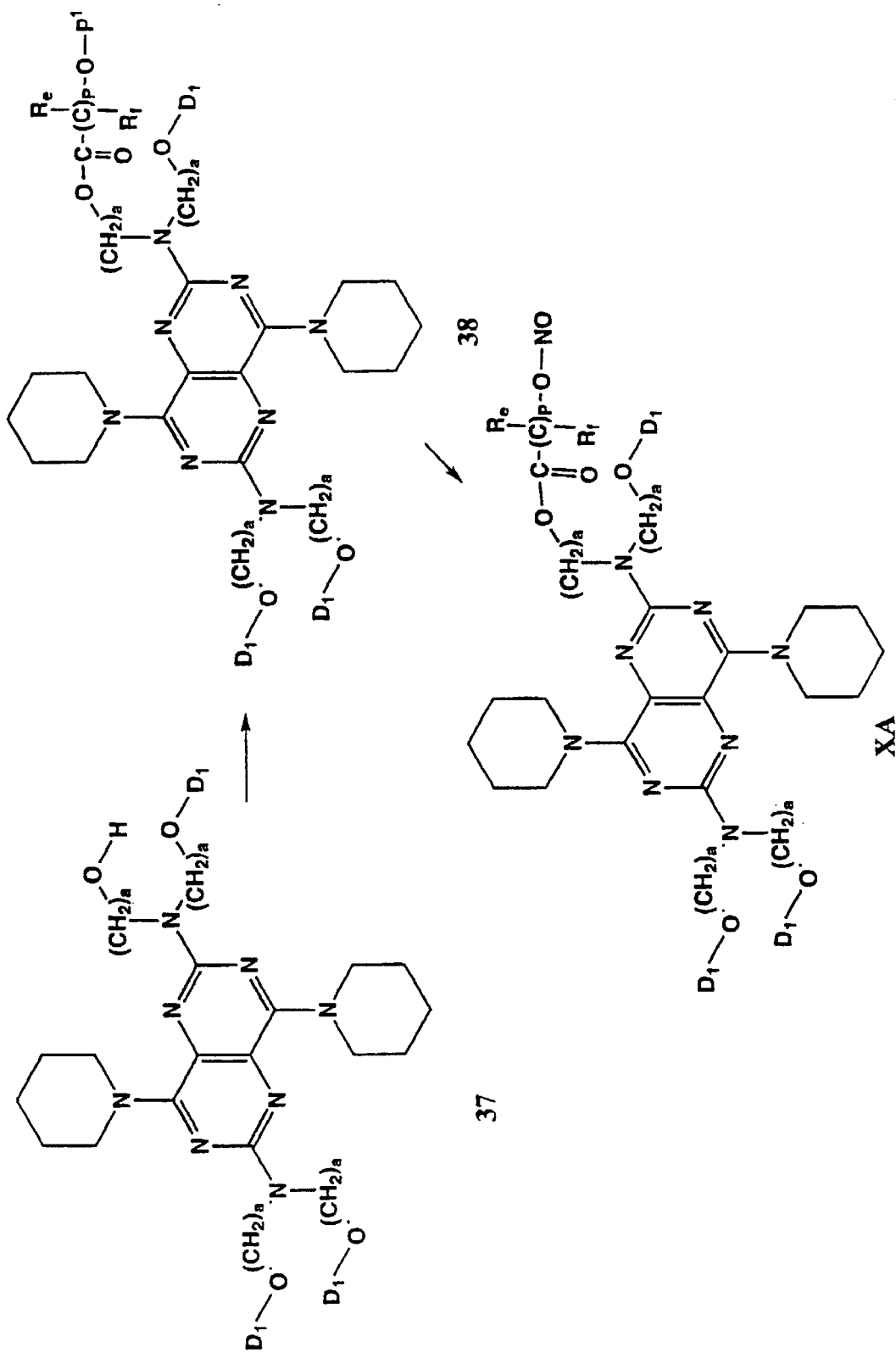
Figure 29:
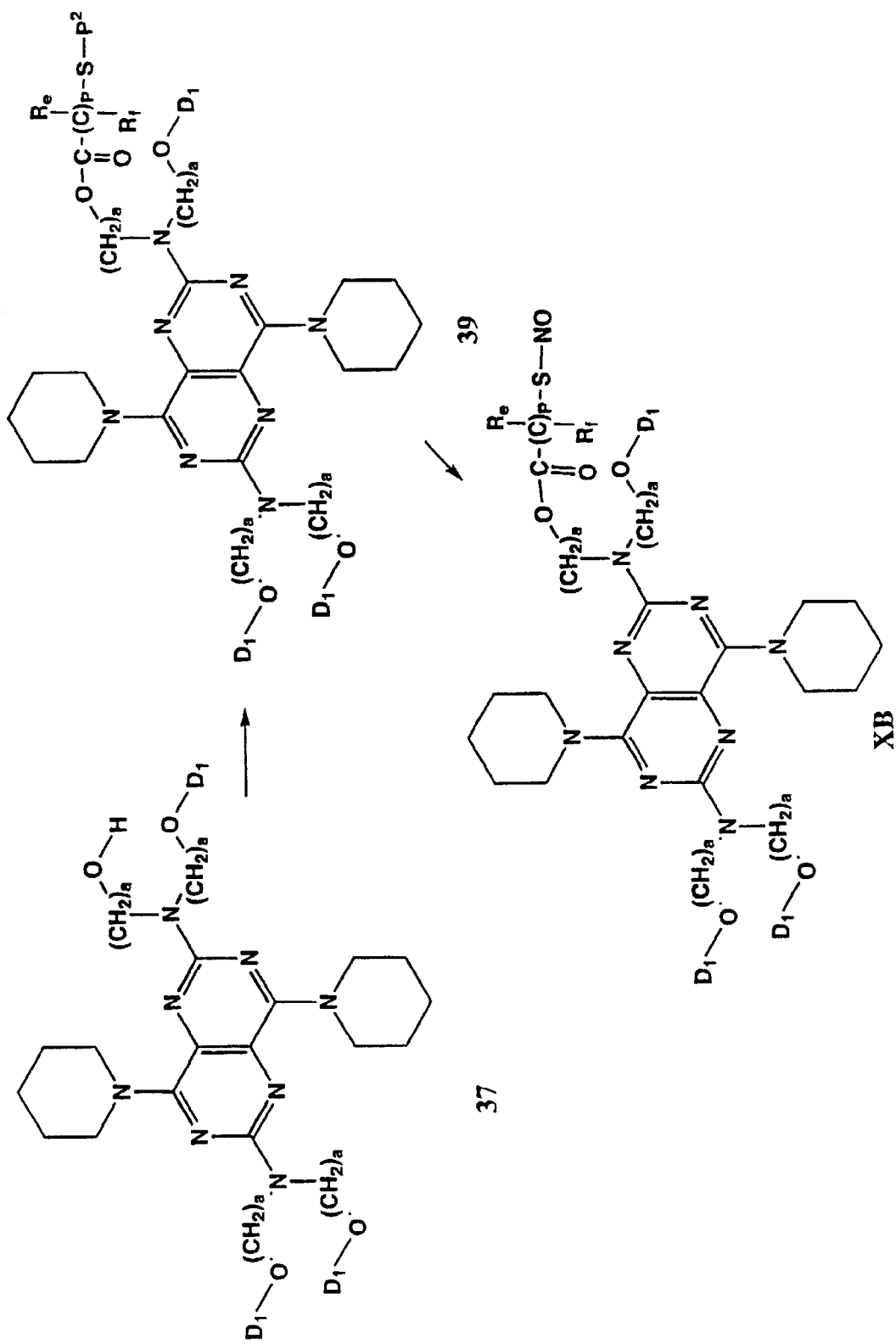
Figure 30:
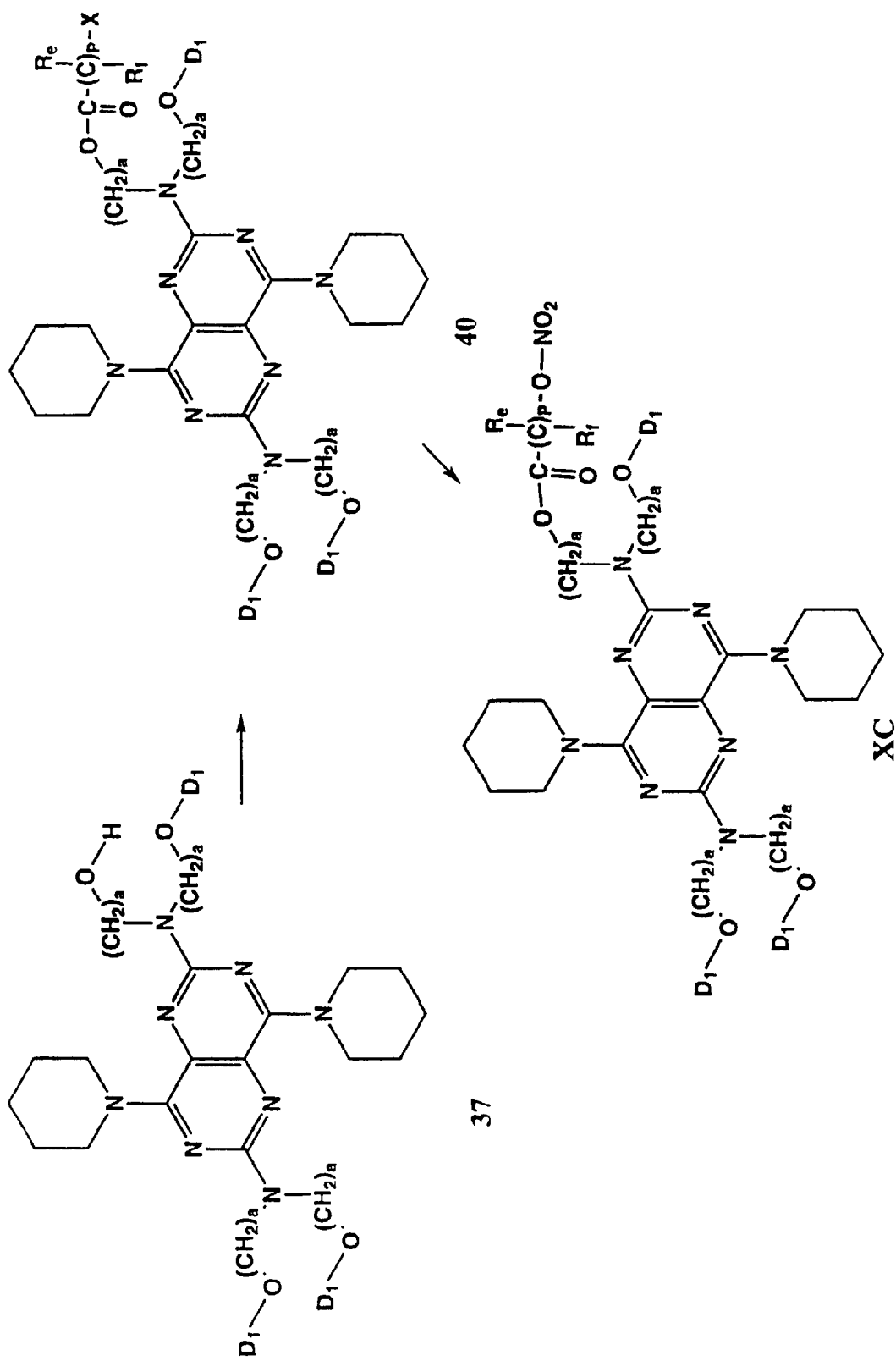
Figure 31:
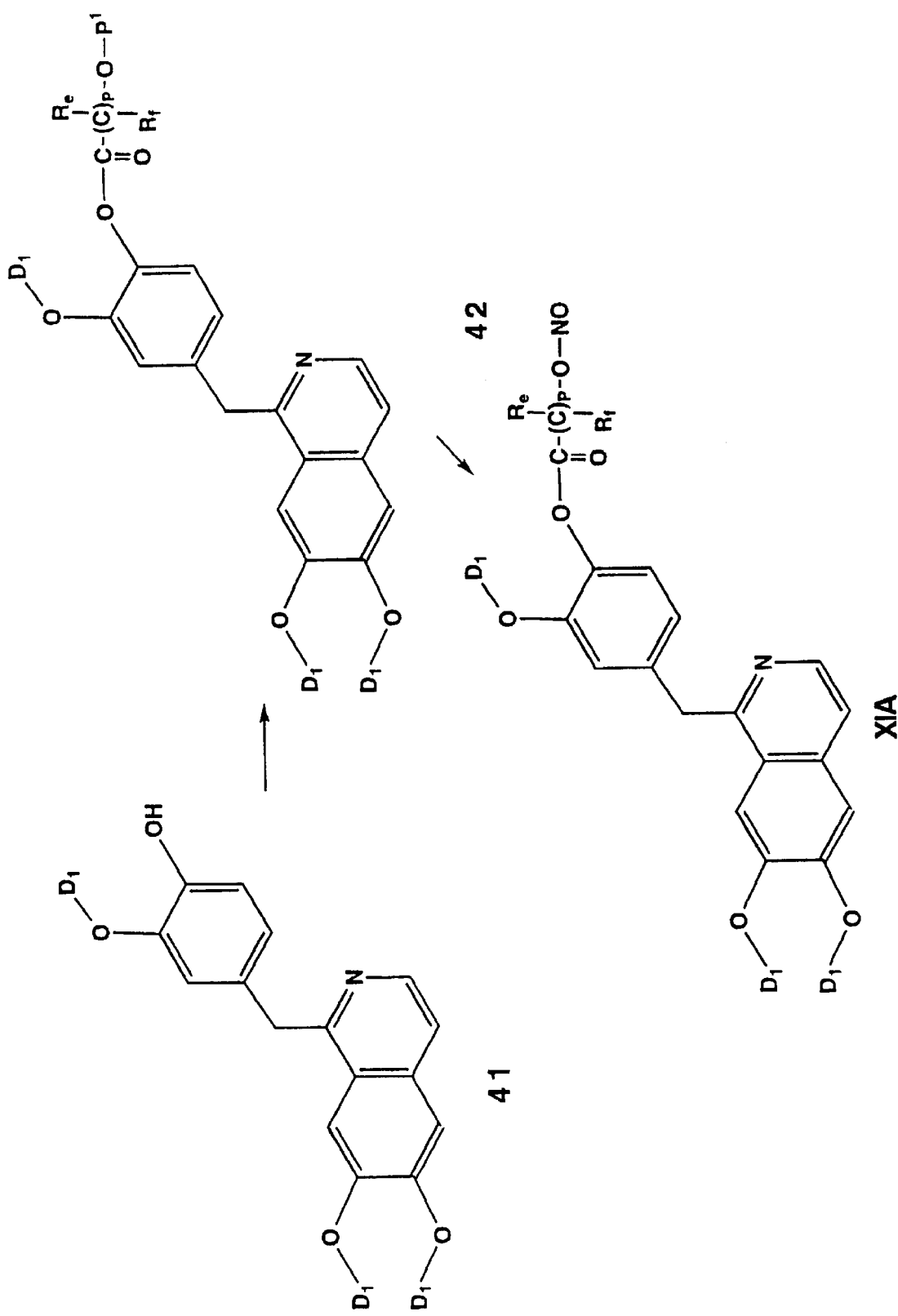
Figure 32:
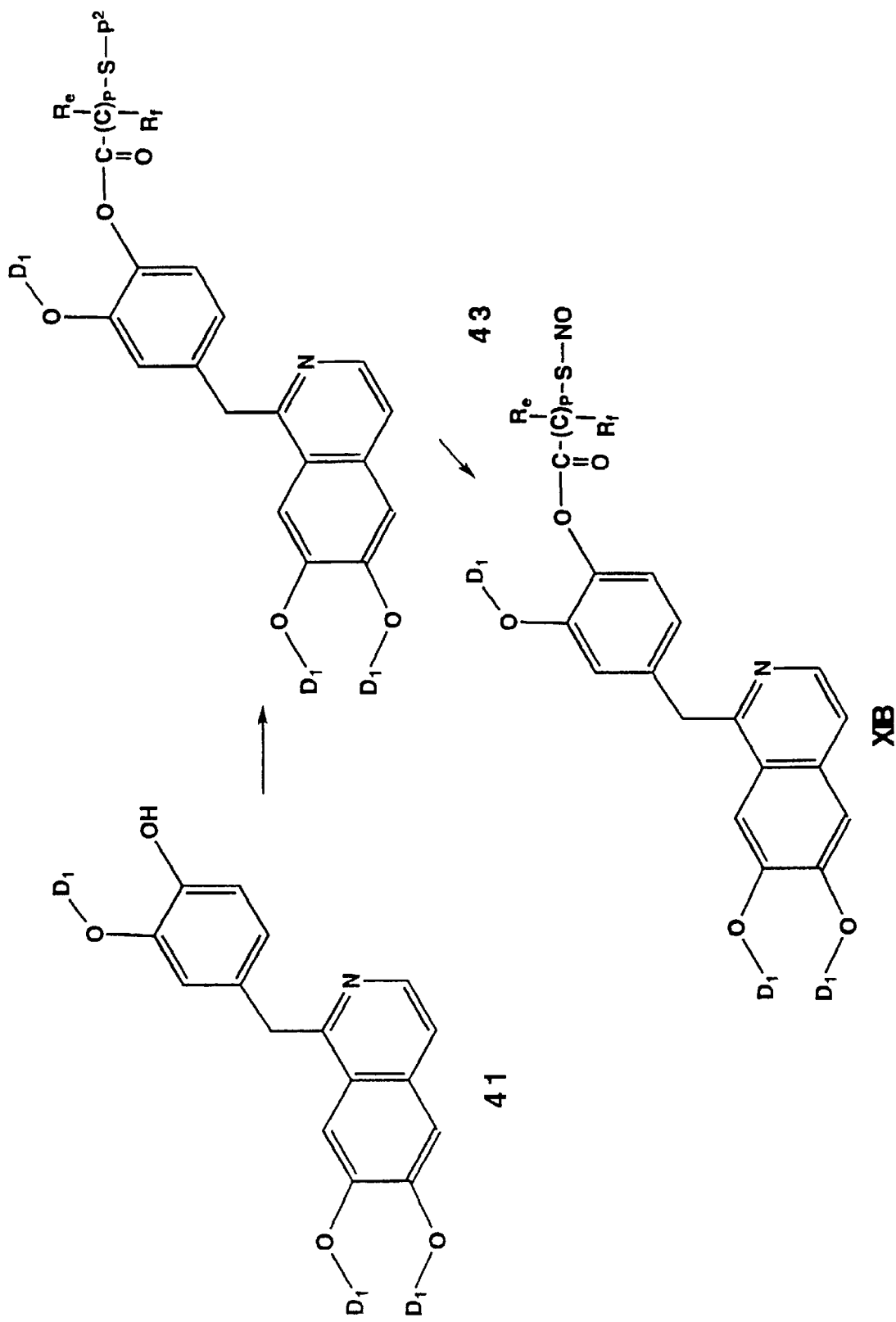
Figure 33:
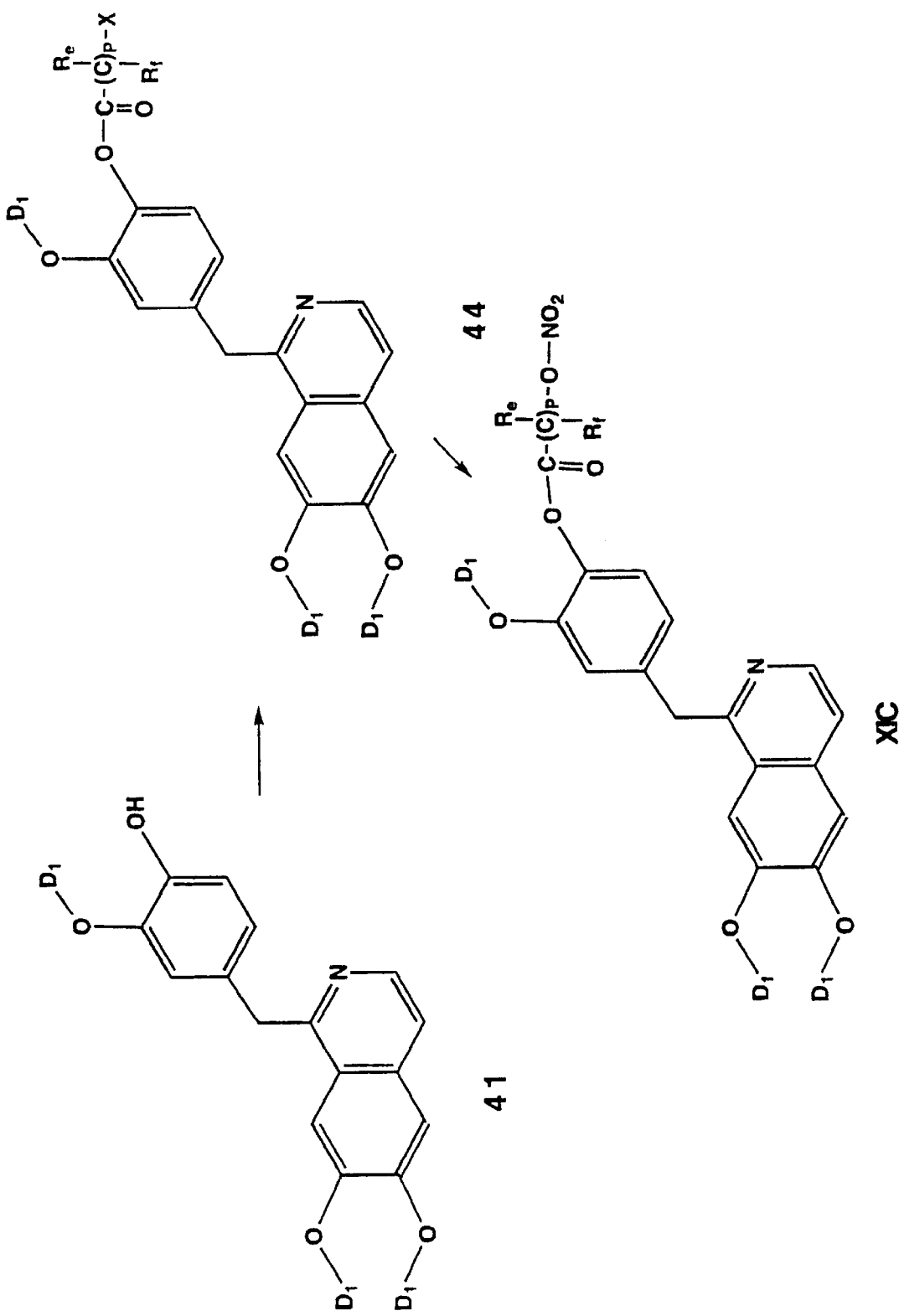
Figure 34:
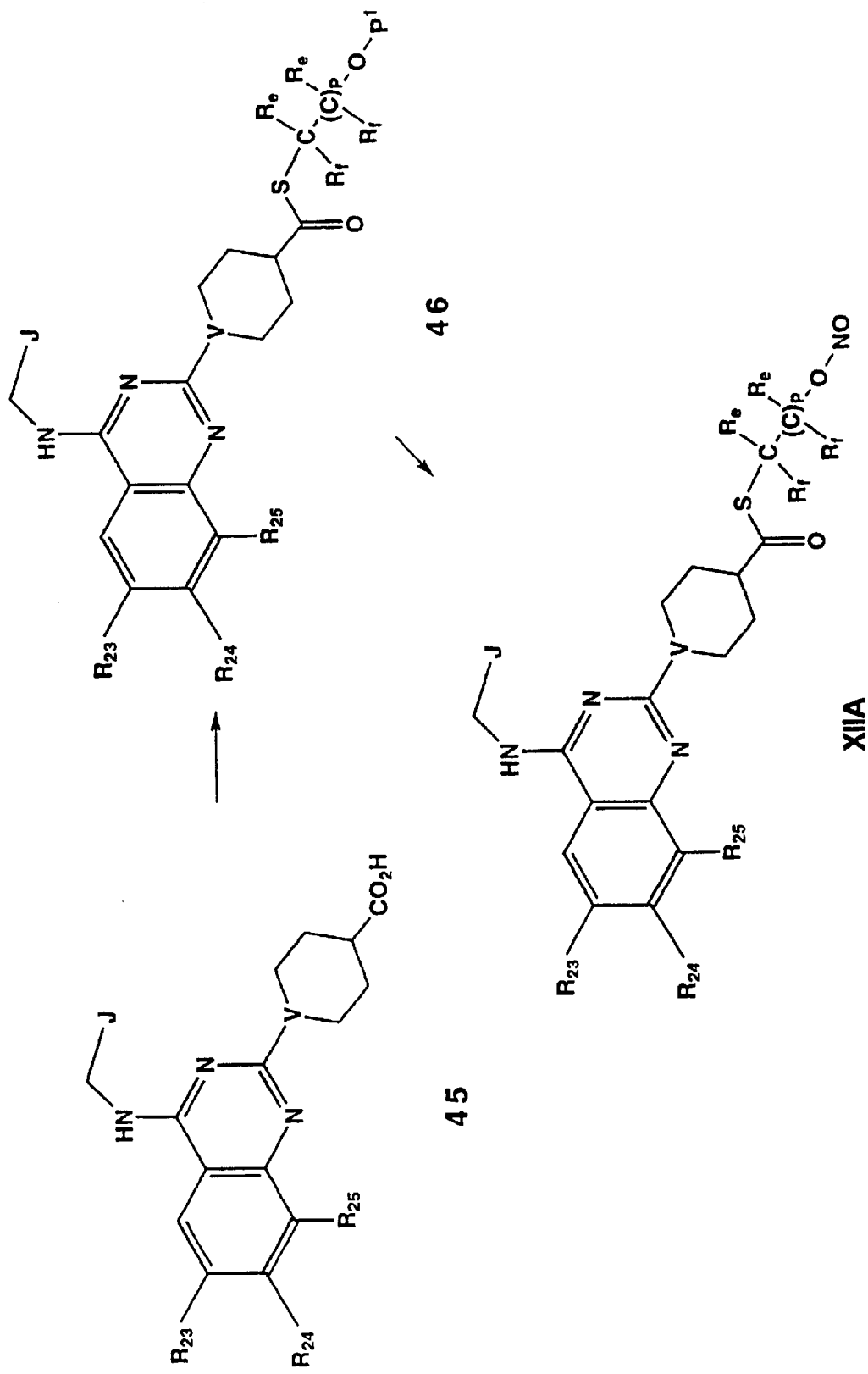
Figure 35:
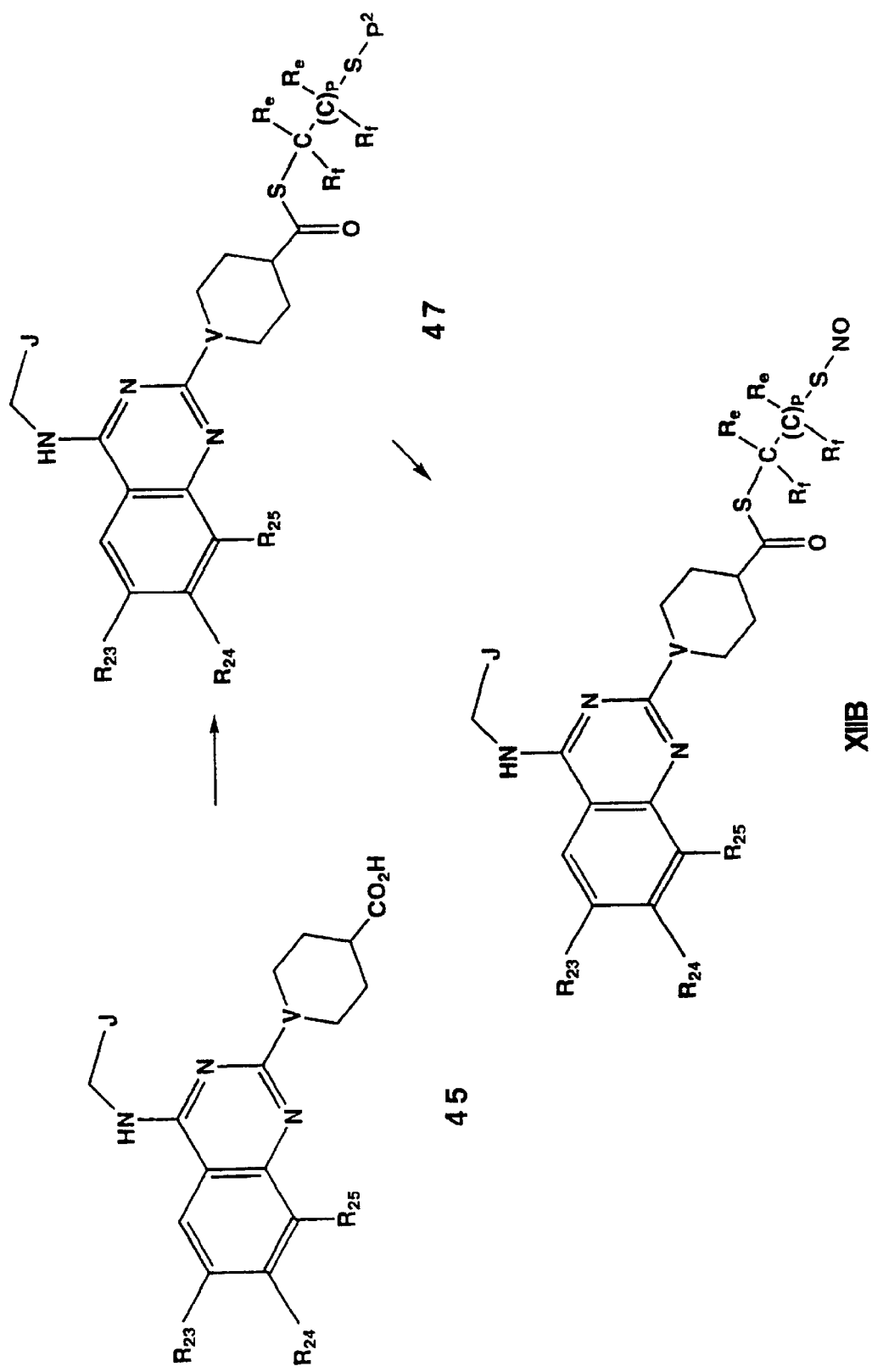
Figure 36:
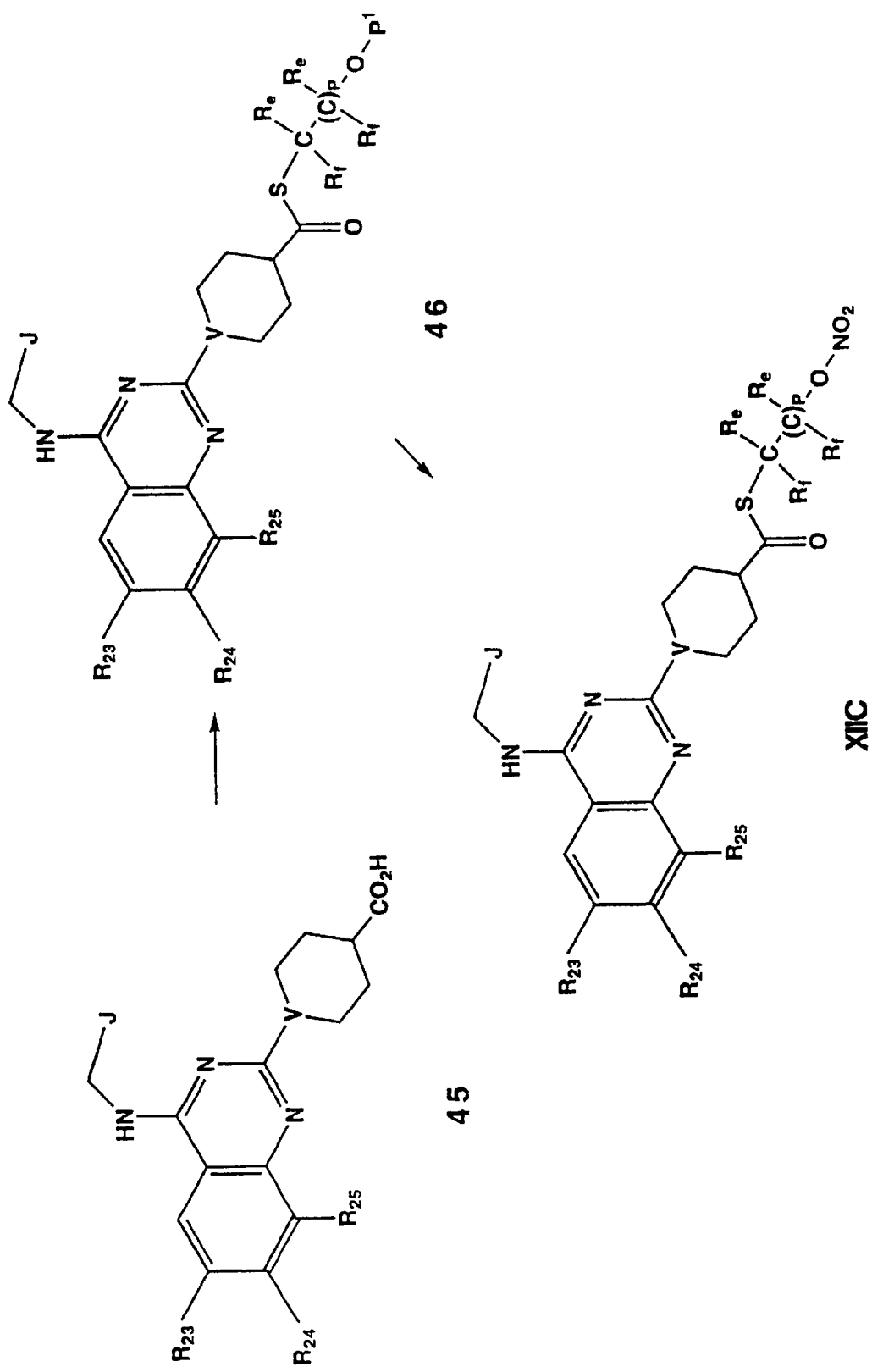
Figure 37:
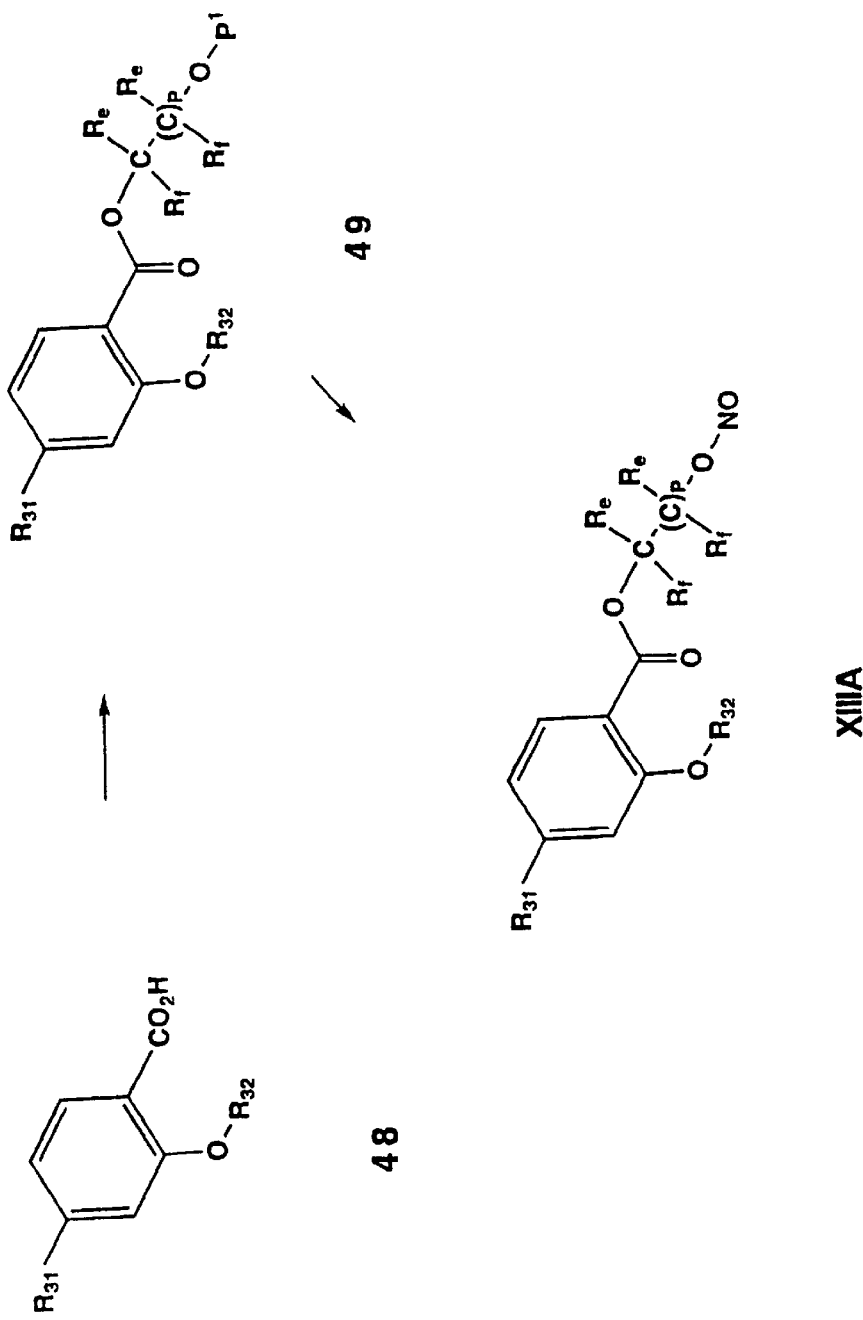
Figure 38:
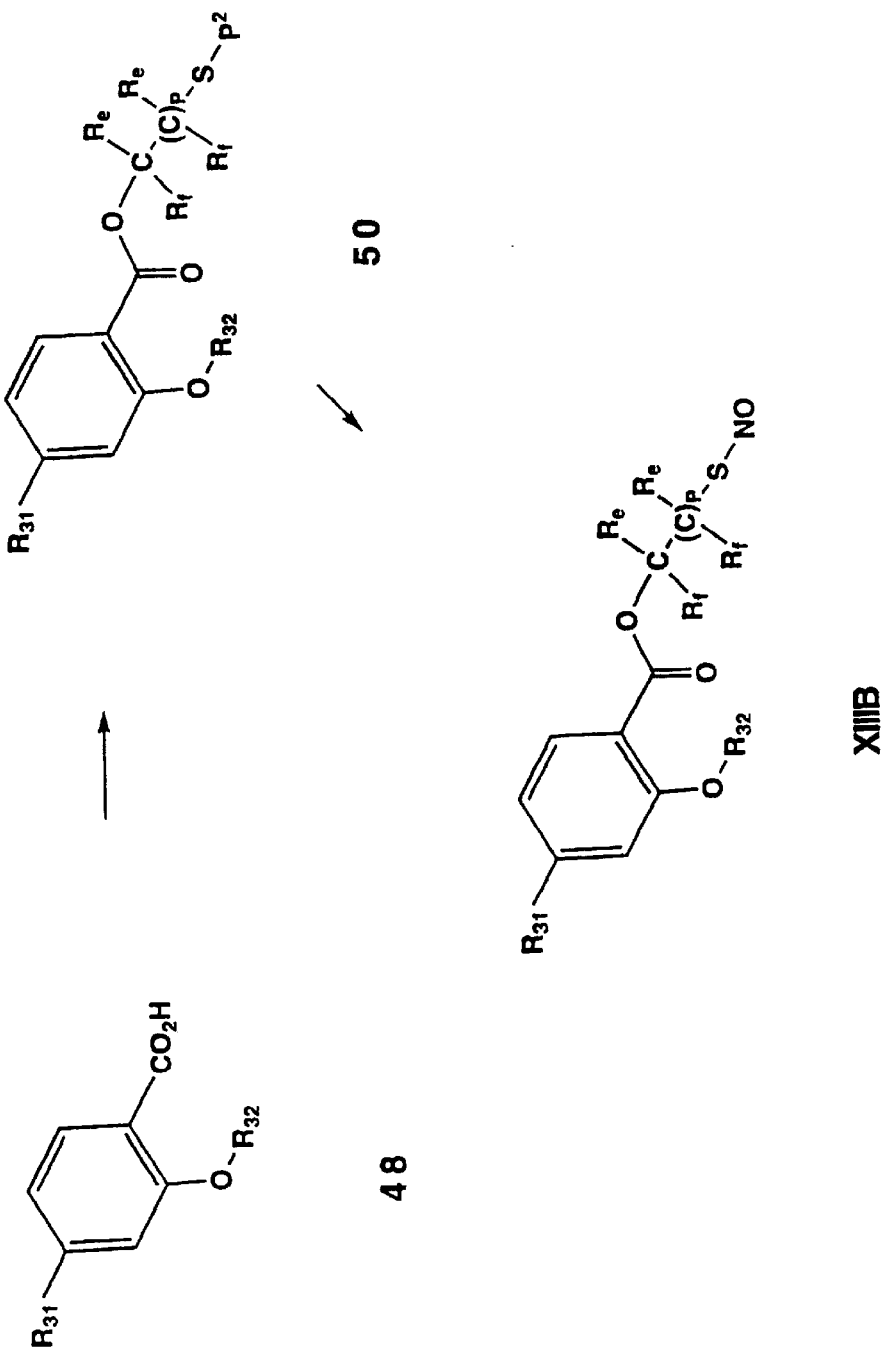
Figure 39:
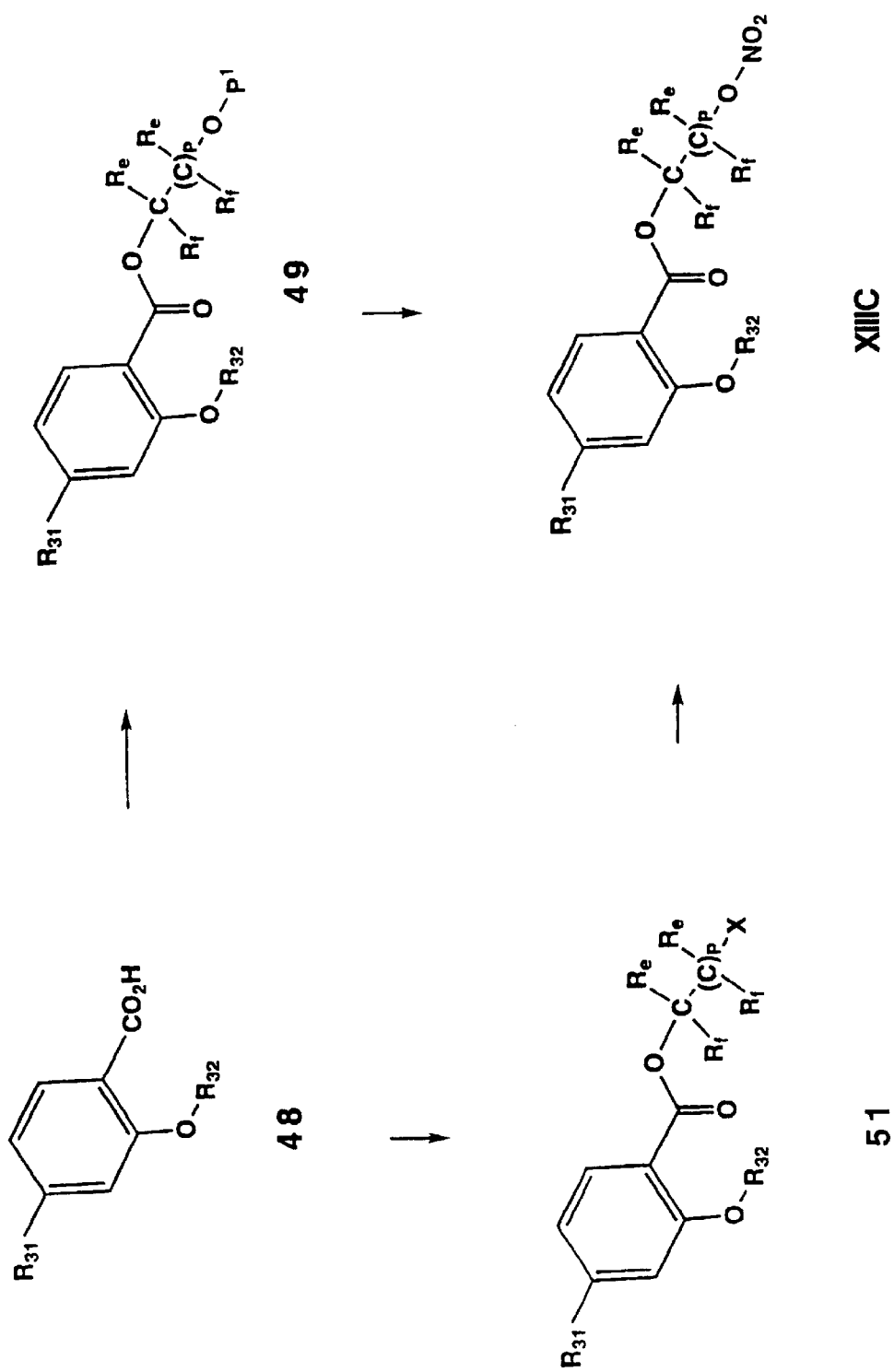
Figure 40:
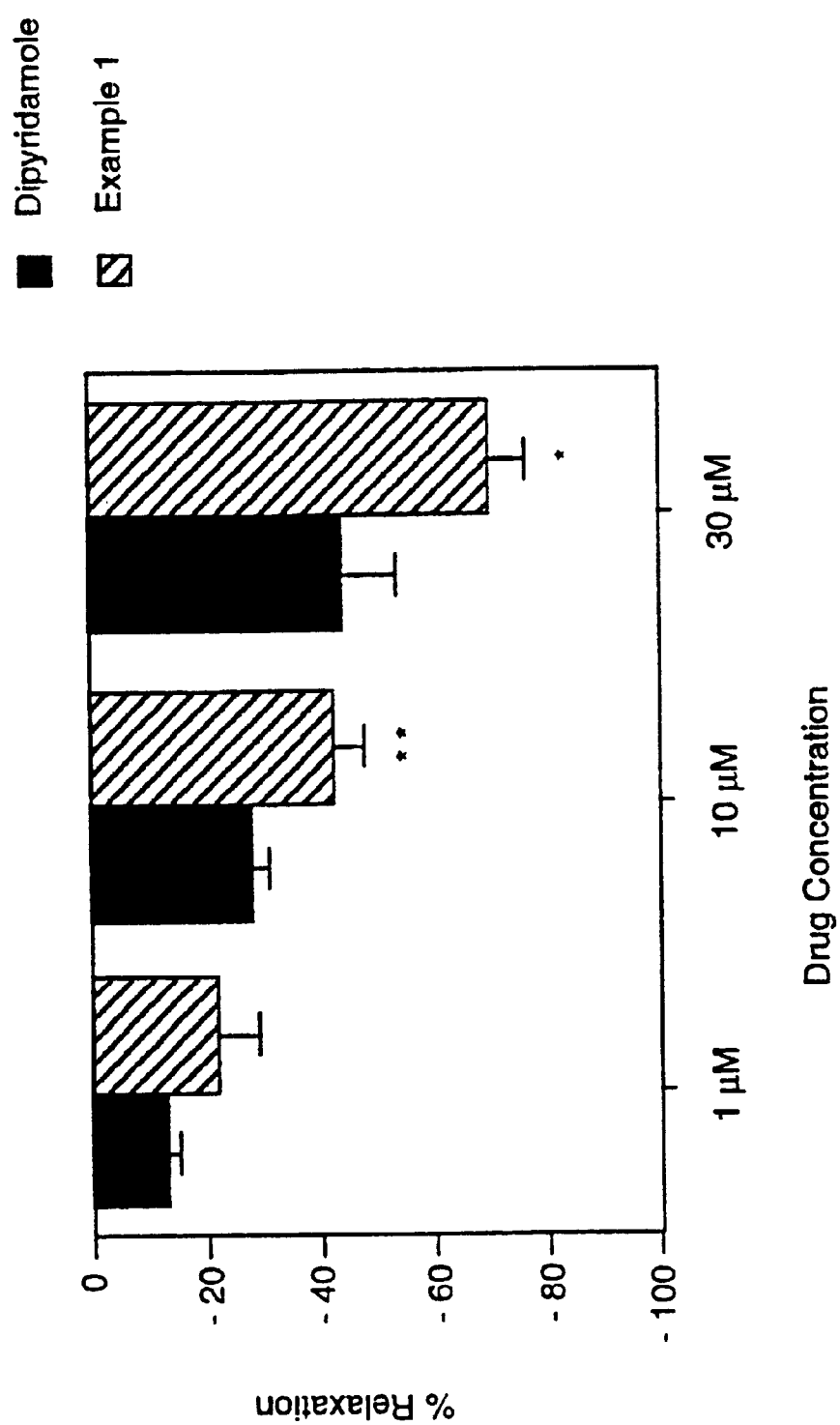

FIG. 1   Synthetic scheme for the preparation of nitrite containing substituted benzene derivatives.
FIG. 2   Synthetic scheme for the preparation of nitrosothiol containing substituted benzene derivatives.
FIG. 3   Synthetic scheme for the preparation of nitrate containing substituted benzene derivatives.
FIG. 4   Synthetic scheme for the preparation of nitrite containing imidazo[2,1-b]quinazoline derivatives.
FIG. 5   Synthetic scheme for the preparation of nitrosothiol containing imidazo[2,1-b]quinazoline derivatives.
FIG. 6   Synthetic scheme for the preparation of nitrate containing imidazo[2,1-b]quinazoline derivatives.
FIG. 7   Synthetic scheme for the preparation of nitrite containing purine-6-one derivatives.
FIG. 8   Synthetic scheme for the preparation of nitrosothiol containing purine-6-one derivatives.
FIG. 9   Synthetic scheme for the preparation of nitrate containing purine-6-one derivatives.
FIG. 10  Synthetic scheme for the preparation of nitrite containing pyrimidin-4-one derivatives.
FIG. 11  Synthetic scheme for the preparation of nitrosothiol containing pyrimidine-4-one derivatives.
FIG. 12  Synthetic scheme for the preparation of nitrate containing pyrimidin-4-one derivatives.
FIG. 13  Synthetic scheme for the preparation of nitrite containing 2-pyridone derivatives.
FIG. 14  Synthetic scheme for the preparation of nitrosothiol containing 2-pyridone derivatives.
FIG. 15  Synthetic scheme for the preparation of nitrate containing 2-pyridone derivatives.
FIG. 16  Synthetic scheme for the preparation of nitrite containing purine-2,6-dione derivatives.
FIG. 17  Synthetic scheme for the preparation of nitrosothiol containing purine-2,6-one derivatives.
FIG. 18  Synthetic scheme for the preparation of nitrate containing purine-2,6-dione derivatives.
FIG. 19  Synthetic scheme for the preparation of nitrite containing quinoline derivatives.
FIG. 20  Synthetic scheme for the preparation of nitrosothiol containing quinoline derivatives.
FIG. 21  Synthetic scheme for the preparation of nitrate containing quinoline derivatives.
FIG. 22  Synthetic scheme for the preparation of nitrite containing substituted pyridine derivatives.
FIG. 23  Synthetic scheme for the preparation of nitrosothiol containing substituted pyridine derivatives.
FIG. 24  Synthetic scheme for the preparation of nitrate containing substituted pyridine derivatives.
FIG. 25  Synthetic scheme for the preparation of nitrite containing benzo[c] [1,6]naphthyridine derivatives.
FIG. 26  Synthetic scheme for the preparation of nitrosothiol containing benzo[c] [1,6]naphthyridine derivatives.
FIG. 27  Synthetic scheme for the preparation of nitrate containing benzo[c] [1,6]naphthyridine derivatives.
FIG. 28  Synthetic scheme for the preparation of nitrite containing 2,6-dihydroxyalkylamino-4,8-dipiperidino pyrimido [5,4-d]pyrimidine derivatives.
FIG. 29  Synthetic scheme for the preparation of nitrosothiol containing 2,6-dihydroxyalkylamino-4,8-dipiperidino pyrimido [5,4-d]pyrimidine derivatives.
FIG. 30  Synthetic scheme for the preparation of nitrate containing 2,6-dihydroxyalkylamino-4,8-dipiperidino pyrimido [5,4-d]pyrimidine derivatives.
FIG. 31  Synthetic scheme for the preparation of nitrite containing 1-((3,4-dihydroxyphenyl)methyl)-6,7-isoquinoline derivatives.
FIG. 32  Synthetic scheme for the preparation of nitrosothiol containing1-((3,4-dihydroxyphenyl)methyl)-6,7-isoquinoline derivatives.
FIG. 33  Synthetic scheme for the preparation of nitrate containing1((3,4-dihydroxyphenyl)methyl)-6,7-isoquinoline derivatives.
FIG. 34  Synthetic scheme for the preparation of nitrite containing substituted quinazoline derivatives.
FIG. 35  Synthetic scheme for the preparation of nitrosothiol containing substituted quinazoline derivatives.
FIG. 36  Synthetic scheme for the preparation of nitrate containing substituted quinazoline derivatives.
FIG. 37  Synthetic scheme for the preparation of nitrite containing substituted phenol derivatives.
FIG. 38  Synthetic scheme for the preparation of nitrosothiol containing substituted phenol derivatives.
FIG. 39  Synthetic scheme for the preparation of nitrate containing substituted phenol derivatives.
FIG. 40  Graph of comparative in vitro relaxation effects of dipyridamole and Example 1 in phenylephrine The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to $R_{50}O$— wherein $R_{50}$ is lower alkyl as defined in this specification. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "hydroxy" as used herein refers to —OH.

The term "hydroxyalkyl" as used herein refers to a hydroxy group as previously defined appended to a lower alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —$NH_2$.

The term "nitrate" as used herein refers to —O—$NO_2$.

The term "alkylamino" as used herein refers to $R_{50}NH$— wherein $R_{50}$ is as defined in this specification, for example, methylamino, ethylamino, butylamino, and the like.

The term "dialkylamino" as used herein refers to $R_{52}R_{53}N$— wherein $R_{52}$ and $R_{53}$ are independently selected from lower alkyl groups as defined in this specification, for example dimethylamino, diethylamino, methyl propylamino and the like.

The term "nitro" as used herein refers to the group —$NO_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "alkylaryl" as used herein refers to a lower alkyl radical to which is appended an aryl group. Representative arylalkyl groups include benzyl, phenylethyl, hydroxybenzyl, fluorobenzyl, fluorophenylethyl and the like.

The term "arylalkoxy" as used herein refers to an alkoxy radical to which is appended an aryl group. Representative arylalkoxy groups include benzyloxy, phenylethoxy, chlorophenylethoxy and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "bridged cycloalkyl" herein refers to two or more cycloalkyl radicals fused via adjacent or non-adjacent carbon atoms, including but not limited to adamantyl and decahydronapthyl.

The term "cycloalkoxy" as used herein refers to $R_{54}O-$ wherein $R_{54}$ is cycloalkyl as defined in this specification. Representative examples of alkoxy groups include cyclopropoxy, cyclopentyloxy, and cyclohexyloxy and the like.

The term "arylthio" herein refers to $R_{55}S-$ wherein $R_{55}$ is an aryl group.

The term "alkylsulfinyl" herein refers to $R_{50}-S(O)_2-$ wherein $R_{50}$ is as defined in this specification.

The term "carboxamido" herein refers to $-C(O)NH_2$.

The term "carbamoyl" herein refers to $-O-C(O)NH_2$.

The term "carboxyl" herein refers to $-CO_2H$.

The term "carbonyl" herein refers to $-C(O)-$.

The term "halogen" or "halo" as used herein refers to I, Br, Cl, or F.

The term "haloalkyl" as used herein refers to a lower alkyl radical to which is appended one or more halogens. Representative examples of a haloalkyl group include trifluoromethyl, chloromethyl, 2-bromobutyl, 1-bromo-2 chloro-pentyl and the like.

The term "haloalkoxy" as used herein refers to a haloalkyl radical to which is appended an alkoxy group. Representative examples of haloalkoxy groups include, 1,1,1-trichloroethoxy, 2-bromobutoxy and the like.

The term "heteroaryl" as used herein refers to a mono- or bi- cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole and isoxazole.

The term "heterocyclic ring" refers to any 3-, 4-, 5-, 6-, or 7-membered nonaromatic ring containing at leas one nitrogen atom, oxygen, or sulfur atom which is bonded to an atom which is not part of the heterocyclic ring.

The term "arylheterocyclic ring" as used herein refers to a bi- or tricyclic ring comprised of an aryl ring as previously defined appended via two adjacent carbons of the aryl group to a heterocyclic ring as previously defined.

The term "heterocyclic compounds" herein refers to mono and polycyclic compounds containing at least one heteroaryl or heterocyclic ring.

The term "amido" as used herein refers to $-NH-C(O)-R_{56}$ wherein $R_{56}$ is a lower akyl, aryl, or hereroaryl group as defined in this specification The term "alkylamido" as used herein refers to $R_{50}N-C(O)-R_{56}$ wherein $R_{50}$ is as defined in this specification and $R_{56}$ is a lower akyl, aryl, or hereroaryl group as defined in this specification.

Examples of contemplated PDE inhibitors to which a nitric oxide adduct may be directly or indirectly linked include dipyridamole, zaprinast, sildenafil, filaminast, denbufyllene, piclamilast, zardaverine, rolipram, papaveroline, E4021, and triflusal.

Sources of information for the above include Goodman and Gilman, The Pharmacological Basis of Therapeutics (9th Ed.), McGraw-Hill, Inc., 1996; the Physician's Desk Reference (49th Ed.), Medical Economics (1995); Drug Facts and Comparisons (1993 Ed), Facts and Comparisons (1993); and The Merck Index (12th Ed.), Merck & Co., Inc. (1996), all of which are incorporated herein by reference in their entirety.

A principal aspect of the invention relates to novel nitrosated and/or nitrosylated phosphodiesterase inhibitors.

One embodiment of this aspect provides compounds having the structure:

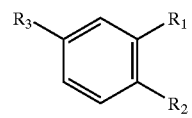

I wherein, $R_1$ is alkoxy, cycloalkoxy, halogen, or

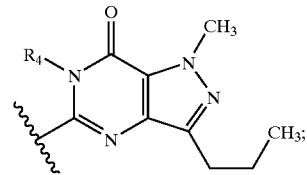

$R_2$ is hydrogen, alkoxy, or haloalkoxy; and $R_3$ is selected from:

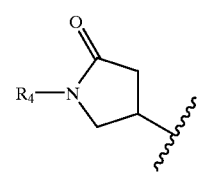

(i)

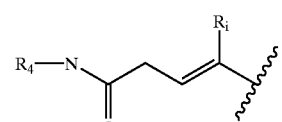

(ii)

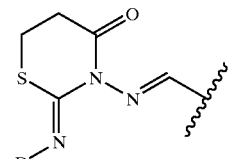

(iii)

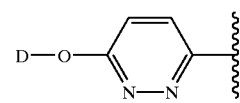

(iv)

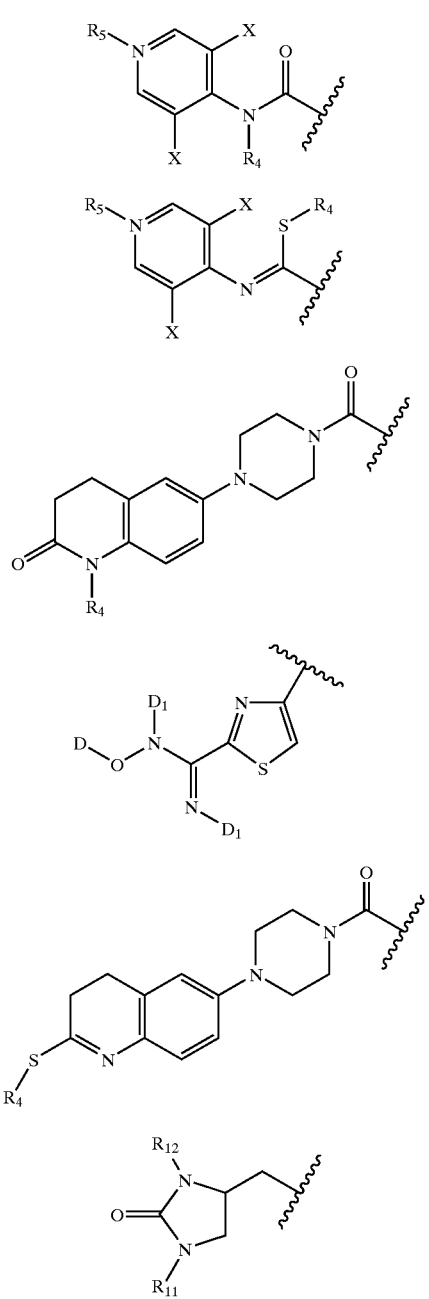

wherein
D is selected from (i) —NO; (ii) —NO$_2$; (iii) —C(R$_d$)—O—C(O)—Y—Z—[C(R$_e$)(R$_f$)]$_p$—T—Q in which R$_d$ is hydrogen, lower alkyl, cycloalkyl, aryl, alkylaryl, aryl or heteroaryl, Y is oxygen, sulfur, or N$_i$ in which R$_i$ is hydrogen, lower alkyl, R$_e$ and R$_f$ at each occurrence are independently selected from hydrogen, lower alkyl, cycloalkyl, aryl, heteroaryl, arylalkyl, amino, alkylamino, amido, alkylamido, dialkylamino, carboxy, or taken together are carbonyl, cycloalkyl or bridged cycloalkyl, p is an integer from 1 to 6, T is a covalent bond, oxygen, sulfur or nitrogen, Z is selected from a covalent bond, alkyl, cycloalkyl, aryl, heteroaryl, arylalkyl or arylheterocyclic ring, and Q is selected from —NO or —NO$_2$; (iv) —C(O)—T$^1$—Z—[C(R$_e$)R$_f$)]$_p$—T$^2$—Q wherein T$^1$ and T$^2$ are independently selected from T and R$_e$, R$_f$, p, Q, Z, and T are as defined in this specification; (v) —C(O)—Z—[G—[C(R$_e$)(R$_f$)]$_p$—T—Q]$_p$ wherein G is (i) a covalent bond; (ii)—T—C(O)—; (iii) —C(O)—T, or (iv) Y, and wherein R$_e$, R$_f$, p, Q, T, Y, and Z are as defined in this specification; (v) —C(O)—T[C(R$_y$)(R$_z$)]$_p$ wherein R$_y$ and R$_z$ are independently selected from —T$^1$—[C(R$_e$)(R$_f$)]$_p$—G—[C(R$_e$)(R$_f$)]$_p$—T$^2$— wherein G, R$_e$, R$_f$, p, Q, T, T$^1$, and T$^2$ are as defined in this specification;

R$_4$ is selected from (i) hydrogen, (ii) —C(R$_d$)—O—C(O)—Y—Z—[C(R)(R$_e$)(R$_f$)]$_p$—T—Q, (iii) —C(O)—T$^1$—[C(R$_e$)(R$_f$)]$_p$—T$^2$—Q, (iv) —C(O)—Z—[G—[C(R$_e$)(R$_f$)]$_p$—T—Q]$_p$; and wherein R$_d$, R$_e$, R$_f$, p, G, T$^1$, T$^2$, Q, Y, and Z are defined as in this specification;

R$_5$ is selected from a lone pair of electrons or —C(R$_d$)—O—C(O)—Y—Z—[C(R$_e$)(R$_f$)]$_p$—T—Q wherein R$_d$, R$_e$, R$_f$, p, T, T$^1$, T$^2$, Q, Y, and Z are defined as in this specification;

R$_{11}$ and R$_{12}$ are independently selected from hydrogen or R$_4$ wherein R$_4$ is as defined in this specification with the provision that R$_{11}$ and R$_{12}$ are not both hydrogen;

X is a halogen and;

D$_1$ is selected from D or hydrogen and wherein D is as defined in this specification.

Another embodiment of this aspect provides compounds having the structure:

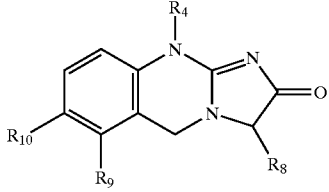

wherein,

R$_4$ is as defined in this specification;

R$_8$ is selected from hydrogen or lower alkyl;

R$_9$ is selected from hydrogen or halogen; and

R$_{10}$ is selected from:
(i) hydrogen

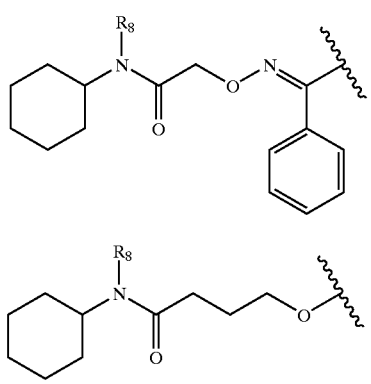

wherein R$_8$ is as defined in this specification.

Another embodiment of this aspect provides compounds having the structure:

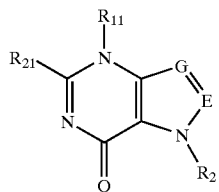

III wherein,

E is selected from nitrogen or —CH—;
G is selected from nitrogen or —C(R$_8$)—;
R$_{21}$ is selected from:

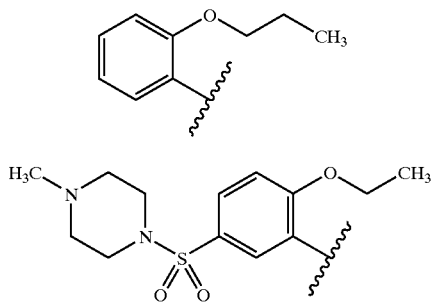

(i)

(ii)

R$_{22}$ is selected from R$_{12}$ or lower alkyl; and
R$_8$, R$_{11}$, and R$_{12}$ are as defined in this specification.

Another embodiment of this aspect provides compounds having the structure:

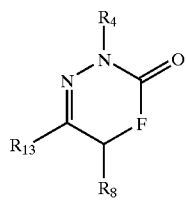

IV wherein,

F is selected from —CH$_2$— or sulfur;
R$_4$ and Ra are as defined in this specification; and
R$_{13}$ is selected from:

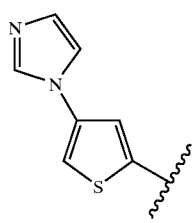

(i)

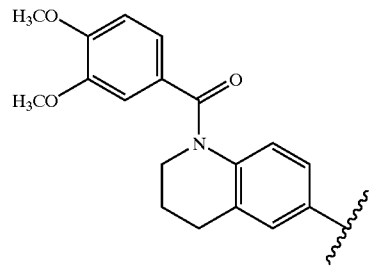

(ii)

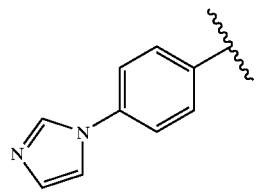

(iii)

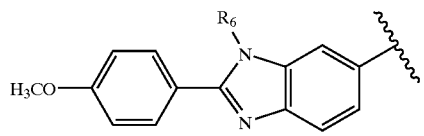

(iv)

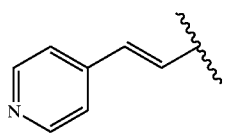

(v)

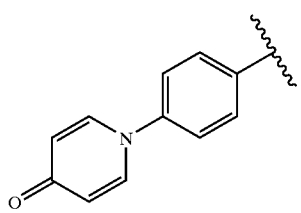

(vi)

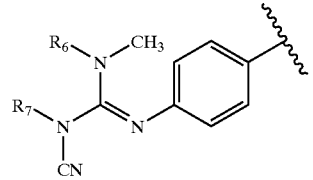

(vii)

wherein,

R$_6$ and R$_7$ are independently selected from hydrogen or R$_4$ wherein R$_4$ is as defined in this specification.

Another embodiment of this aspect provides compounds having the structure:

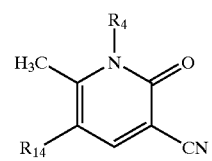

V wherein,

R$_4$ is as defined in this specification; and $R_{14}$ is selected from:

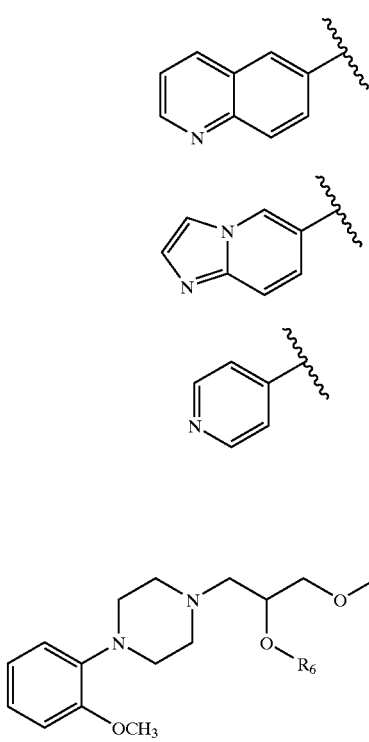

wherein $R_6$ is as defined in this specification.

Another embodiment of this aspect provides compounds having the structure:

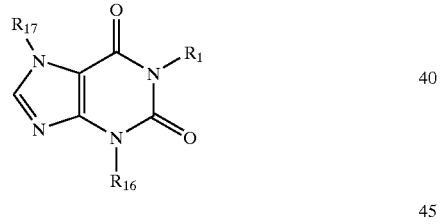

VI wherein, $R_{15}$ is hydrogen, lower alkyl, $R_4$, or —$(CH_2)_4$—C$(CH_3)_2$—O—$D_1$;

$R_{16}$ is lower alkyl; and $R_{17}$ is hydrogen, lower alkyl, $CH_3$—C(O)—$CH_2$—, $CH_3$—O—$CH_2$—, or D with the provision that either $R_{15}$ or $R_{17}$ must be selected to contain D and wherein D and $D_1$ are as defined in this specification.

Another embodiment of this aspect provides compounds having the structure:

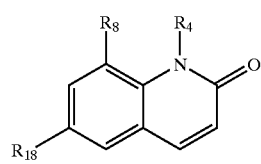

VII wherein, $R_4$ and $R_8$ are as defined in this specification and $R_{18}$ is selected from:

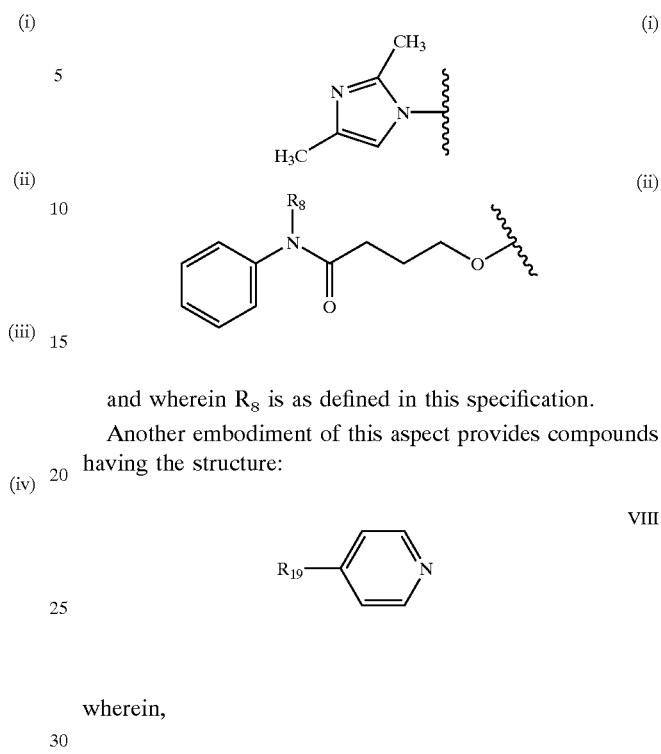

and wherein $R_8$ is as defined in this specification.

Another embodiment of this aspect provides compounds having the structure:

VIII wherein, $R_{19}$ is selected from:

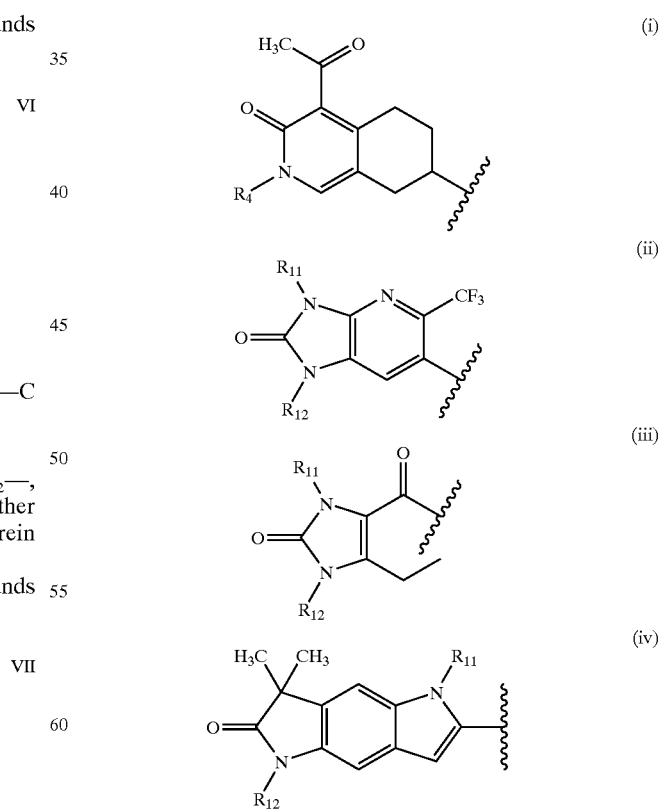

and wherein $R_4$, $R_{11}$, and $R_{12}$ are defined as in this specification.

Another embodiment of this aspect provides compounds having the structure:

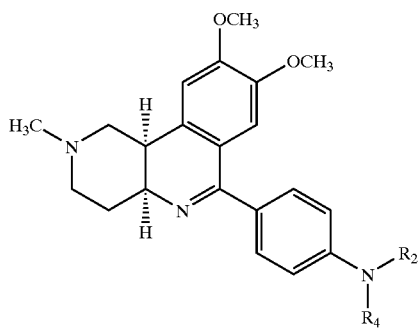

IX wherein, $R_{20}$ is selected from:

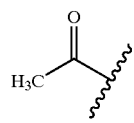

(i)

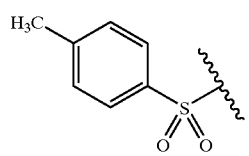

(ii)

and wherein $R_4$ is defined as in this specification.

Another embodiment of this aspect provides compounds having the structure:

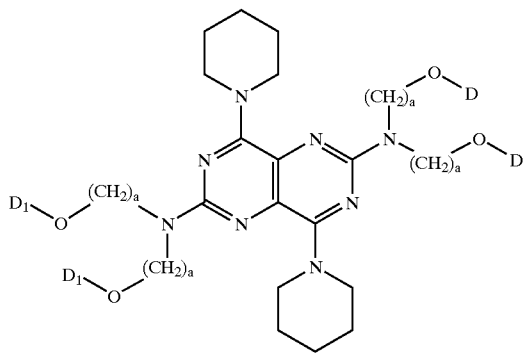

X wherein, a is an integer from 2 to 3 and D and $D_1$ are defined as in this specification.

Another embodiment of this aspect provides compounds having the structure:

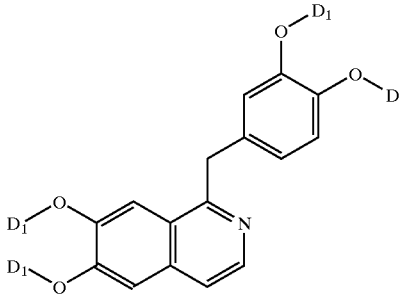

XI wherein D and $D_1$ are defined as in this specification.

Another embodiment of this aspect provides compounds having the structure:

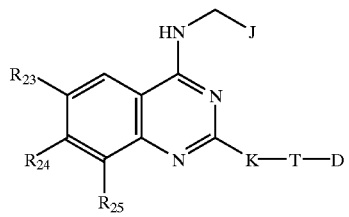

XII wherein,

J is selected from:

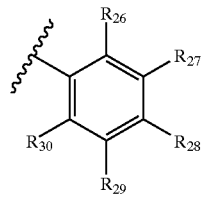

(i)

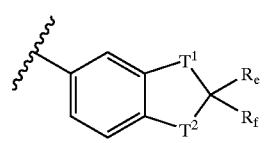

(ii)

K is selected from:

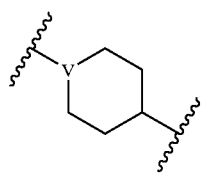

(i)

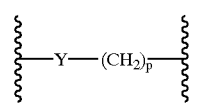

(ii)

wherein V is carbon or nitrogen;

$R_{23}$, $R_{24}$, $R_{25}$, $R_{26}$, $R_{27}$, $R_{28}$, $R_{29}$, and $R_{30}$ are independently selected from hydrogen, halogen, alkoxy, nitrile, carboxamido, or carboxyl; and wherein p, $R_e$, $R_f$, T, $T^1$, $T^2$, Y and D are defined as in this specification.

Another embodiment of this aspect provides compounds having the structure:

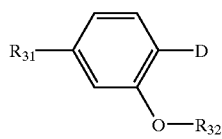

XIII wherein,

R$_{31}$ is alkyl, halogen, haloalkyl, or haloalkoxy;

R$_{32}$ is selected from D$_1$ or —C(O)R$_8$; and wherein D$_1$ and R$_8$ are defined as in this specification.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the invention provides processes for making the novel compounds of the invention and to the intermediates useful in such processes.

Some of the compounds of the invention are synthesized as shown in FIGS. 1 through 39 presented below, in which R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_e$, R$_f$, p, D, D$_1$, E, F, G, J, K, and X are as defined i n this specification or as depicted in the reaction schemes for structures I–XIII; P$^1$ is an oxygen protecting group and P$^2$ is a sulfur protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur and oxygen protecting groups is well known in the art for protecting thiol and alcohol groups against undesirable reactions during a synthetic procedure and many such protecting groups are known, c.f., T. H. Greene and P. G. M. Wuts, *Protective Groups in Organic Synthesis,* John Wiley & Sons, New York (1991).

Another embodiment of this aspect provides processes for making compounds having structures I and to the intermediates useful in such processes as follows.

Nitroso compounds of formula (I) wherein R$_1$, R$_2$, R$_e$, R$_f$, and p are defined as in this specification and a nitrite containing imide is representative of the R$_3$ group as defined in this specification may be prepared as outlined in FIG. 1. The amide group of formula 1 is converted to the imide of formula 2 wherein p, R$_e$ and R$_f$ are defined as in this specification by reaction with an appropriate protected alcohol containing activated acylating agent wherein P$^1$ is as defined in this specification Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a trimethylsilyl ether, a tert-butyldimethylsilyl ether, or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IA.

Nitroso compounds of formula (I) wherein R$_1$, R$_2$, R$_e$, R$_f$, and p are defined as in this specification and a nitrosothiol containing imide is representative of the R$_3$ group as defined in this specification may be prepared as outlined in FIG. 2. The amide group of formula 1 is converted to the imide of formula 3 wherein p, R$_e$ and R$_f$ are defined as in this specification by reaction with an appropriate protected thiol containing activated acylating agent wherein P$^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IB. Alternatively, treatment of the deprotected thiol derived from compound 3 with a stoichiometric quantity of sodium nitrite in an acidic aqueous or alcoholic solution affords the compound of the formula IB.

Nitro compounds of formula (I) wherein R$_1$, R$_2$, R$_e$, R$_f$, and p are defined as in this specification and an nitrate containing imide is representative of the R$_3$ group as defined in this specification may be prepared as outlined in FIG. 3. The amide group of the formula 1 is converted to the imide of the formula 4 wherein p, R$_e$ and R$_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 4 with a suitable nitrating agent such as silver nitrate in an inert solvent such as acetonitrile affords the compound of the formula IC.

Another embodiment of this aspect provides processes for making compounds having structures II and to the intermediates useful in such processes as follows.

Nitroso compounds of formula (II) wherein $R_8$, $R_9$, $R_{10}$, $R_e$, $R_f$, and p are defined as in this specification, and a nitrite containing amide is representative of the $R_4$ group as defined in this specification may be prepared as outlined in FIG. 4. The imidazo[2,1-b]quinazoline of formula 5 is converted to the acylimidazo[2,1-b]quinazoline of formula 6 wherein p, $R_e$ and $R_f$ are defined as in this specification by reaction with an appropriate protected alcohol containing activated acylating agent wherein $P^1$ is as defined in this specification. Preferred methods for the formation of acylimidazo[2,1-b]quinazolines are reacting the imidazo[2,1-b]quinazoline with the preformed acid chloride or symmetrical anhydride of the protected alcohol containing acid or condensing the imidazo[2,1-b]quinazoline and protected alcohol containing acid in the presence of a dehydrating agent such as dicyclohexylcarbodiimide (DCC) or 1-ethyl-3 (3dimethylaminopropyl) carbodimide hydrochloride (EDAC. HCl) with or without a catalyst such as 4-dimethylaminopyridine (DMAP) or 1-hydroxybenzotriazole (HOBt). Preferred protecting groups for the alcohol moiety are silyl ethers such as a trimethylsilyl or tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IIA.

Nitroso compounds of formula (II) wherein $R_8$, $R_9$, $R_{10}$, $R_e$, $R_f$, and p are defined as in this specification, and a nitrosothiol containing amide is representative of the $R_4$ group as defined in this specification may be prepared as outlined in FIG. 5. The imidazo[2,1-b]quinazoline of formula 5 is converted to the acylimidazo[2,1-b]quinazoline of formula 7 wherein p, $R_e$ and $R_f$ are defined as in this specification by reaction with an appropriate protected thiol containing activated acylating agent wherein $P^2$ is as defined in this specification. Preferred methods for the formation of acylated imidazo[2,1-b]quinazolines are reacting the imidazo[2,1-b]quinazoline with the preformed acid chloride or symmetrical anhydride of the protected thiol containing acid or condensing the imidazo[2,1-b]quinazoline and protected thiol containing acid in the presence of a dehydrating agent such as DCC or EDAC. HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIB. Alternatively, treatment of the deprotected thiol derived from compound 7 with a stoichiometric quantity of sodium nitrite in an acidic aqueous or alcoholic solution affords the compound of the formula IIB.

Nitro compounds of formula (II) wherein $R_8$, $R_9$, $R_{10}$, $R_e$, $R_f$, and p are defined as in this specification, and a nitrate containing amide is representative of the $R_4$ group as defined in this specification may be prepared as outlined in FIG. 6. The imidazo[2,1-b]quinazoline of formula 5 is converted to the acylimidazo[2,1-b]quinazoline of formula 8 wherein p, $R_e$ and $R_f$ are defined as in this specification and X is a halogen by reaction with an appropriate halide containing activated acylating agent. Preferred methods for the formation of the acylimidazo[2,1-b]quinazolines are reacting the imidazo[2,1-b)quinazoline with the preformed acid chloride or symmetrical anhydride of the halide containing acid or condensing the alcohol and halide containing acid in the presence of a dehydrating agent such as DCC or EDAC. HCl with or without a catalyst such as DMAP or HOBt. Preferred halides are bromide and iodide. Reaction of the acylimidazo [2,1-b]quinazoline of the formula 8 with a suitable nitrating agent such as silver nitrate in an inert solvent such as acetonitrile affords the compound of the formula IIC.

Another embodiment of this aspect provides processes for making compounds having structures III and to the intermediates useful in such processes as follows.

Nitroso compounds of formula (III) wherein E, G, $R_{21}$, $R_{22}$, $R_e$, $R_f$, and p are defined as in this specification and a nitrite containing amide is representative of the $R_{11}$ group as defined in this specification may be prepared as outlined in FIG. 7. The purine-6-one group of formula 9 is converted to the acylated purine6-one of formula 10 wherein p, $R_e$ and $R_f$ are defined as in this specification by reaction with an appropriate protected alcohol containing activated acylating agent wherein $P^1$ is as defined in this specification. Preferred methods for the formation of acylated purine-6-ones are reacting the purine-6-one with the preformed acid chloride or symmetrical anhydride of the protected alcohol containing acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IIA.

Nitroso compounds of formula (III) wherein E, G, $R_{21}$, $R_{22}$, $R_e$, $R_f$, and p are defined as in this specification and an nitrosothiol containing amide is representative of the $R_{11}$ group as defined in this specification may be prepared as outlined in FIG. 8. The purine group of formula 9 is converted to the acylated purine-6-one of formula 11 wherein p, $R_e$ and $R_f$ are defined as in this specification by reaction with an appropriate protected thiol containing activated acylating agent wherein $P^2$ is as defined in this specification. Preferred methods for the formation of acylated purine4-ones are reacting the purine-6-one with the preformed acid chloride or symmetrical anhydride of the protected alcohol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIIB. Alternatively, treatment of the deprotected thiol derived from compound 11 with a stoichiometric quantity of sodium nitrite in an acidic aqueous or alcoholic solution affords the compound of the formula IIIB.

Nitro compounds of formula (III) wherein E, G, $R_{21}$, $R_{22}$, $R_e$, $R_f$, and p are defined as in this specification and an nitrate containing amide is representative of the $R_{11}$ group as defined in this specification may be prepared as outlined in FIG. 9. The purine4-one of formula 9 is converted to the acylated purine6-one the of formula 12 wherein p, $R_e$ and $R_f$ are defined and X is halogen. Preferred methods for the formation of acylated purine6-ones are reacting the purine one with the preformed acid chloride or symmetrical anhydride of the halide containing acid. Preferred halides are bromide and iodide. Reaction of the of the acylated purine4one of the formula 12 with a suitable nitrating agent such as silver nitrate in an inert solvent such as acetonitrile affords the compound of the formula IIIC.

Another embodiment of this aspect provides processes for making compounds having structures IV and to the intermediates useful in such processes as follows.

Nitroso compounds of formula (IV) wherein F, $R_8$, $R_{13}$, $R_e$, $R_f$, and p are defined as in this specification and a nitrite containing acyl hydrazide is representative of the $R_4$ group as defined in this specification may be prepared as outlined in FIG. 10. The 3 (2-H)-pyridazinone or 2H-1, 2, 3, 4-thiadiazine of formula 13 is converted to the 3 (2-acyl)-pyridazinone or 2-acyl-1, 2, 3, 4-thiadiazine of formula 14 wherein p, $R_e$ and $R_f$ are defined as in this specification by reaction with an appropriate protected alcohol containing activated acylating agent wherein $P^1$ is as defined in this specification. Preferred methods for the formation of 3 (2-acyl)-pyridazinone or 2-acyl-1, 2, 3, 4-thiadiazine are reacting the 3 (2H)-pyridazinone or 2H-1, 2, 3, 4-thiadiazine with the preformed acid chloride or symmetrical anhydride of the protected alcohol containing acid or condensing the 3 (2-H)-pyridazinone or 2H-1, 2, 3, 4-thiadiazine and protected alcohol containing acid in the presence of a dehydrating agent such as DCC or EDAC. HCl with a catalyst such as DMAP or HOBt. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IVA.

Nitroso compounds of formula (IV) wherein F, $R_8$, $R_{13}$, $R_e$, $R_f$, and p are defined as in this specification and a nitrosothiol containing acyl hydrazide is representative of the $R_4$ group as defined in this specification may be prepared as outlined in FIG. 11. The 3 (2-H)-pyridazinone or 2H-1, 2, 3, 4-thiadiazine of formula 13 is converted to the 3 (2-acyl)-pyridazinone or 2-acyl-1, 2, 3, 4-thiadiazine of formula 15 wherein p, $R_e$ and $R_f$ are defined as in this specification by reaction with an appropriate protected thiol containing activated acylating agent wherein $P^2$ is as defined in this specification. Preferred methods for the formation of 3 (2-acyl)-pyridazinones or 2-acyl-1, 2, 3, 4-thiadiazines are reacting the 3 (2-H)-pyridazinone or 2H-1, 2, 3, 4-thiadiazine with the preformed acid chloride or symmetrical anhydride of the protected thiol containing acid or condensing the 3 (2-H)-pyridazinone or 2H-1, 2, 3, 4-thiadiazine and protected thiol containing acid in the presence of a dehydrating agent such as DCC or EDAC. HCl with a catalyst such as DMAP or HOBt. Preferred protecting groups for the thiol moiety are as a thioester such as a thioacetate or thiobenzoate, as a disulfide, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IVB. Alternatively, treatment of the deprotected thiol derived from compound 15 with a stoichiometric quantity of sodium nitrite in an acidic aqueous or alcoholic solution affords the compound of the formula IVB.

Nitro compounds of formula (IV) wherein F, $R_8$, $R_{13}$, $R_e$, $R_f$, and p are defined as in this specification and an nitrate-containing acyl hydrazide is representative of the $R_4$ group as defined in this specification may be prepared as outlined in FIG. 12. The 3 (2-H) pyridazinone or 2H-1, 2, 3, 4thiadiazine of formula 13 is converted to the 3 (2-acyl) pyridazinone or 2-acyl-1, 2, 3, 4-thiadiazine of formula 16 wherein p, $R_e$ and $R_f$ are defined and X is halogen. Preferred methods for the formation of 3 (2-acyl)-pyridazinones or 2-acyl-1, 2, 3, 4-thiadiazines are reacting the 3 (2-H)-pyridazinone or 2H-1, 2, 3, 4-thiadiazine with the preformed acid chloride or symmetrical anhydride of the halide containing acid or condensing the 3 (2-H)-pyridazinone or 2H-1, 2, 3, 4-thiadiazine and halide containing acid in the presence of a dehydrating agent such as DCC or EDAC. HCl with a catalyst such as DMAP or HOBt. Preferred halides are bromide and iodide. Reaction of the 3 (2-acyl)-pyridazinone or 2-acyl-1, 2, 3, 4-thiadiazine of formula 16 with a suitable nitrating agent such as silver nitrate in an inert solvent such as acetonitrile affords the compound of the formula IVC.

Another embodiment of this aspect provides processes for making compounds having structures V and to the intermediates useful in such processes as follows.

Nitroso compounds of formula (V) wherein $R_{14}$, $R_e$, $R_f$, and p are defined as in this specification and an nitrite containing imide is representative of the $R_4$ group as defined in this specification may be prepared as outlined in FIG. 13. The amide group of formula 17 is converted to the imide of formula 18 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VA.

Nitroso compounds of formula (V) wherein $R_{14}$, $R_e$, $R_f$, and p are defined as in this specification and a nitrosothiol containing imide is representative of the $R_4$ group as defined in this specification may be prepared as outlined in FIG. 14. The amide group of formula 17 is converted to the imide of formula 19 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, trimethoxybenzyl in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VB. Alternatively, treatment of the deprotected thiol derived from compound 19 with a stoichiometric quantity of sodium nitrite in an acidic aqueous or alcoholic solution affords the compound of the formula VB.

Nitro compounds of formula (V) wherein $R_{14}$, $R_e$, $R_f$, and p are defined as in this specification and a nitrate containing imide is representative of the $R_4$ group as defined in this specification may be prepared as outlined in FIG. 15. The amide group of the formula 17 is converted to the imide of the formula 20 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 20 with a suitable nitrating agent such as silver nitrate in an inert solvent such as acetonitrile affords the compound of the formula VC.

Another embodiment of this aspect provides processes for making compounds having structures VI and to the intermediates useful in such processes as follows.

Nitroso compounds of formula (VI) wherein $R_{15}$, $R_{16}$, $R_e$, $R_f$, and p are defined as in this specification and a nitrite containing acyl imidazolide is representative of the $R_{17}$ group as defined in this specification may be prepared as outlined in FIG. 16. The 1H-purine-2, 6dione of formula 21 is converted to the acylated derivative of the formula 22 wherein p, $R_e$ and $R_f$ are defined as in this specification by reaction with an appropriate protected alcohol containing activated acylating agent wherein $P^1$ is as defined in this specification. Preferred methods for the formation of acylated 1H-purine-2, 6-diones are reacting the 1H-purine-2, 6-dione with the preformed acid chloride or symmetrical anhydride of the protected alcohol containing acid or condensing the 1H-purine-2, 6-dione and protected alcohol containing acid in the presence of a dehydrating agent such as DCC or EDAC. HCl with a catalyst such as DMAP or HOBt. Preferred protecting groups for the alcohol moiety are silyl ethers such as a tert-butyldimethylsilyl ether or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIA.

Nitroso compounds of formula (VI) wherein $Rl_5$, $R_{16}$, $R_e$, $R_f$, and p are defined as in this specification and a nitrosothiol containing acyl imidazolide is representative of the $R_{17}$ group as defined in this specification may be prepared as outlined in FIG. 17. The 1H-purine-2, 6-dione of formula 21 is converted to the acylated derivative of the formula 23 wherein p, $R_e$ and $R_f$ are defined as in this specification by reaction with an appropriate protected thiol containing activated acylating agent wherein $P^2$ is as defined in this specification. Preferred methods for the formation of acylated 1H-purine-2, 6-diones are reacting the 1H-purine-2, 6-dione, with the preformed acid chloride or symmetrical anhydride of the protected thiol containing acid or condensing the 1H-purine-2, 6-dione and protected thiol containing acid in the presence of a dehydrating agent such as DCC or EDAC. HCl with a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, trimethoxybenzyl in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIB. Alternatively, treatment of the deprotected thiol derived from compound 23 with a stoichiometric quantity of sodium nitrite in an acidic aqueous or alcoholic solution affords the compound of the formula VIB.

Nitro compounds of formula (VI) wherein $R_{15}$, $R_{16}$, $R_e$, $R_f$, and p are defined as in this specification and an O-nitrosated acylated 1H-purine-2, 6-dione is representative of the $R_{17}$ group as defined in this specification may be prepared as outlined in FIG. 18. The 1H-purine-2, 6-dione of the formula 21 is converted to the acylated derivative of the formula 24 wherein p, $R_e$ and $R_f$ are defined as in this specification and X is a halogen by reaction with an appropriate halide containing activated acylating agent. Preferred methods for the formation of acylated 1H-purine-2, 6-diones are reacting the 1H-purine-2, 6-dione with the preformed acid chloride or symmetrical anhydride of the halide containing acid or condensing the 1H-purine-2, 6-dione and halide containing acid in the presence of a dehydrating agent such as DCC or EDAC. HCl with a catalyst such as DMAP or HOBt. Preferred halides are bromide and iodide. Reaction of the acylated 1H-purine-2, 6-dione of the formula 24 with a suitable nitrating agent such as silver nitrate in an inert solvent such as acetonitrile affords the compound of the formula VIC.

Another embodiment of this aspect provides processes for making compounds having structures VII and to the intermediates useful in such processes as follows.

Nitroso compounds of formula (VII) wherein $R_8$, $R_{18}$, $R_e$, $R_f$, and p are defined as in this specification and a nitrite containing imide is representative of the $R_4$ group as defined in this specification may be prepared as outlined in FIG. 19. The amide nitrogen of formula 25 is converted to the imide of formula 26 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIA.

Nitroso compounds of formula (VII) wherein $R_8$, $R_{18}$, $R_e$, $R_f$, and p are defined as in this specification and a nitrosothiol containing imide is representative of the $R_4$ group as defined in this specification may be prepared as outlined in FIG. 20. The amide nitrogen of formula 25 is converted to the imide of formula 27 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VUB. Alternatively, treatment of the deprotected thiol derived from compound 27 with a stoichiometric quantity of sodium nitrite in an acidic aqueous or alcoholic solution affords the compound of the formula VIIB.

Nitro compounds of formula (VII) wherein $R_8$, $R_{18}$, $R_e$, $R_f$, and p are defined as in this specification and a nitrate containing imide is representative of the $R_4$ group as defined in this specification may be prepared as outlined in FIG. 21. The amide group of the formula 25 is converted to the imide of the formula 28 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 28 with a suitable nitrating agent such as silver nitrate in an inert solvent such as acetonitrile affords the compound of the formula VIIC.

Another embodiment of this aspect provides processes for making compounds having structures VIII and to the intermediates useful in such processes as follows.

Nitroso compounds of formula (VIII) wherein $R_e$, $R_f$, and p are defined as in this specification and a nitrite containing imide is representative of the $R_{19}$ group as defined in this specification may be prepared as outlined in FIG. 22 . The amide nitrogen of formula 29 is converted to the imide of formula 30 wherein p, $R_e$ and $R_f$ are defined as in this specification by reaction with an appropriate protected alcohol containing activated acylating agent wherein $P^1$ is as defined in this specification. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIIA.

Nitroso compounds of formula (VIII) wherein $R_e$, $R_f$, and p are defined as in this specification and a nitrosothiol containing imide is representative of the $R_{19}$ group as defined in this specification may be prepared as outlined in FIG. 23. The amide nitrogen of formula 29 is converted to the imide of formula 31 wherein p, $R_e$ and $R_f$ are defined as in this specification by reaction with an appropriate protected thiol containing activated acylating agent wherein $P^2$ is as defined in this specification. Preferred methods for the formation of imides are reacting the amide with the preformed acid chloride of the protected thiol containing acid in the presence of pyridine at low temperature or condensing the amide and protected alcohol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric., acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of the deprotected thiol derived from compound 31 with a stoichiometric quantity of sodium nitrite in an acidic aqueous or alcoholic solution affords the compound of the formula VIIB.

Nitro compounds of formula (VIII) wherein $R_e$, $R_f$, and p are defined as in this specification and a nitrate containing imide is representative of the $R_{19}$ group as defined in this specification may be prepared as outlined in FIG. 24. The amide group of the formula 29 is converted to the imide of the formula 32 wherein p, $R_e$ and $R_f$ are defined as in this specification and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 32 with a suitable nitrating agent such as silver nitrate in an inert solvent such as acetonitrile affords the compound of the formula VIIIC.

Another embodiment of this aspect provides processes for making compounds having structures IX and to the intermediates useful in such processes as follows.

Nitroso compounds of formula (IX) wherein $R_{20}$, $R_e$, $R_f$, and p are defined as in this specification and an nitrate containing imide or sulfonimide is representative of the $R_4$ group as defined in this specification may be prepared as outlined in FIG. 25. The amide or sulfonamide nitrogen of formula 33 is converted to the imide or sulfonimide of formula 34 wherein p, $R_e$ and $R_f$ are defined as in this specification by reaction with an appropriate protected alcohol containing activated acylating agent wherein $P^1$ is as defined in this specification. Preferred methods for the formation of imides or sulfonimide are reacting the amide or sulfonimide with the preformed acid chloride of the protected alcohol containing acid in the presence of pyridine at low temperature or condensing the amide or sulfonimide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IXA Nitroso compounds of formula (IX) wherein $R_{20}$, $R_e$, $R_f$, and p are defined as in this specification and an nitrosothiol containing imide or sulfonimide is representative of the $R_4$ group as defined in this specification may be prepared as outlined in FIG. 26. The amide or sulfonamide nitrogen of formula 33 is converted to the imnide or sulfonimide of formula 35 wherein p, $R_e$ and $R_f$ are defined as in this specification by reaction with an appropriate protected thiol containing activated acylating agent wherein $P^2$ is as defined in this specification. Preferred methods for the formation of imides or sulfonimides are reacting the amide or sulfonimide with the preformed acid chloride of the protected thiol containing acid in the presence of pyridine at low temperature or condensing the amide or sulfonimide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IXB. Alternatively, treatment of the deprotected thiol derived from compound 35 with a stoichiometric quantity of sodium nitrite in an acidic aqueous or alcoholic solution affords the compound of the formula IXB.

Nitro compounds of formula (IX) wherein $R_{20}$, $R_e$, $R_f$, and p are defined as in this specification and a nitrate containing imide or sulfonimide is representative of the $R_4$ group as defined in this specification may be prepared as outlined in FIG. 27. The amide or sulfonamide group of the formula 33 is converted to the imide or sulfonimide of the formula 36 wherein p, $R_e$ and $R_f$ are defined as in this specification and X is a halogen by reaction with an appropriate halide containing activated acylating agent. Preferred methods for the formation of imides or sulfonimide are reacting the amide or sulfonamide with the preformed acid chloride of the halide containing acid in the presence of pyridine at low temperature or condensing the amide or sulfonamide and halide containing symmetrical anhydride in the presence of a catalyst such as sulfuric acid. Preferred halides are bromide and iodide. Reaction of the imide or sulfonimide of the formula 36 with a suitable nitrating agent such as silver nitrate in an inert solvent such as acetonitrile affords the compound of the formula IXC.

Another embodiment of this aspect provides processes for making compounds having structures X and to the intermediates useful in such processes as follows.

Nitroso compounds of formula (X) wherein $D_1$, $R_e$, $R_f$, and p are defined as in this specification and a nitrite containing ester is representative of the D group as defined in this specification may be prepared according to Scheme 28. The alcohol group of formula 37 is converted to the ester of formula 38 wherein p, $R_e$ and $R_f$ are defined as in this specification by reaction with an appropriate protected alcohol containing activated acylating agent wherein $P^1$ is as defined in this specification. Preferred methods for the formation of esters are reacting the alcohol with the preformed acid chloride or symmetrical anhydride of the protected alcohol containing acid or condensing the alcohol and protected alcohol containing acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, TIF, DMF, or acetonitrile with or without an amine base such as pyridine or triethylamine affords the compound of the formula XA.

Nitroso compounds of formula (X) wherein D1, $R_e$, $R_f$, and p are defined as in this specification and a nitrosothiol containing ester is representative of the D group as defined in this specification may be prepared according to Scheme 29. The alcohol group of the formula 37 is converted to the ester of the formula 39 wherein p, $R_e$ and $R_f$ are defined as in this specification by reaction with an appropriate protected thiol containing activated acylating agent wherein $P^2$ is as defined in this specification. Preferred methods for the formation of esters are reacting the alcohol with the preformed acid chloride or symmetrical anhydride of the protected thiol containing acid or condensing the alcohol and protected thiol containing acid with a dehydrating agent such as DCC or EDAC. HCl in the presence of a catalyst such as DMAP or HOBT. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula XB. Alternatively, treatment of the deprotected thiol derived from compound 39 with a stoichiometric quantity of sodium nitrite in aqueous or alcoholic acid affords the compound of the formula XB.

Nitro compounds of formula (X) wherein $D_1$, $R_e$, $R_f$, and p are defined as in this specification and a nitrate containing ester is representative of the D group as defined in this specification may be prepared according to Scheme 30. The alcohol group of the formula 37 is converted to the ester of the formula 40 wherein p, $R_e$ and $R_f$ are defined as in this specification and X is a halogen by reaction with an appropriate halide containing activated acylating agent Preferred methods for the formation of esters are reacting the alcohol with the preformed acid chloride or symmetrical anhydride of the halide containing acid or condensing the alcohol and halide containing acid with a dehydrating agent such as DCC or EDAC. HCl in the presence of a catalyst such as DMAP or HOBt Preferred halides are bromide and iodide. Reaction of the ester of the formula 40 with a suitable nitrating agent such as silver nitrate in an inert solvent such as acetonitrile affords the compound of the formula XC.

Nitroso compounds of formula (XI) wherein $D_1$, $R_e$, $R_f$, and p are defined as in this specification and a nitrite containing ester is representative of the D group as defined in this specification may be prepared according to Scheme 31. The alcohol group of formula 41 is converted to the ester of formula 42 wherein p, $R_e$ and $R_f$ are defined as in this specification by reaction with an appropriate protected alcohol containing activated acylating agent wherein $P^1$ is as defined in this specification. Preferred methods for the formation of esters are reacting the alcohol with the preformed acid chloride or symmetrical anhydride of the protected alcohol containing acid or condensing the alcohol and protected alcohol containing acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula XIA.

Nitroso compounds of formula (XI) wherein $D_1$, $R_e$, $R_f$, and p are defined as in this specification and a nitrosothiol containing ester is representative of the D group as defined in this specification may be prepared according to Scheme 32. The alcohol group of the formula 41 is converted to the ester of the formula 43 wherein p, $R_e$ and $R_f$ are defined as in this specification by reaction with an appropriate protected thiol containing activated acylating agent wherein $P^2$ is as defined in this specification. Preferred methods for the formation of esters are reacting the alcohol with the preformed acid chloride or symmetrical anhydride of the protected thiol containing acid or condensing the alcohol and protected thiol containing acid with a dehydrating agent such as DCC or EDAC. HCl in the presence of a catalyst such as DMAP or HOBt. Preferred protecting groups for the thiol moiety are as a disulfide, a thioester such as a thioacetate or thiobenzoate, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylmethyl in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methyene chloride, THF, DMF, or acetonitrile with or without an amine base such as pyridine or triethylamine affords the compound of the formula XIB. Alternatively, treatment of the deprotected thiol derived from compound 43 with a stoichiometric quantity of sodium nitrite in aqueous or alcoholic acid affords the compound of the formula XIB.

Nitro compounds of formula (XI) wherein $D_1$, $R_e$, $R_f$, and p are defined as in this specification and a nitrate containing ester is representative of the D group as defined in this specification may be prepared according to Scheme 33. The alcohol group of the formula 41 is converted to the ester of the formula 44 wherein p, $R_e$ and $R_f$ are defined as in this specification and X is a halogen by reaction with an appropriate halide containing activated acylating agent. Preferred methods for the formation of esters are reacting the alcohol with the preformed acid chloride or symmetrical anhydride of the halide containing acid or condensing the alcohol and halide containing acid with a dehydrating agent such as DCC or EDAC. HCl in the presence of a catalyst such as DMAP or HOBt. Preferred halides are bromide and iodide. Reaction of the ester of the formula 44 with a suitable nitrating agent such as silver nitrate in an inert solvent such as acetonitrile affords the compound of the formula XIC.

Another embodiment of this aspect provides processes for making compounds having structures XII and to the intermediates useful in such processes as follows.

Nitroso compounds of formula (XI) wherein $R_e$, $R_f$, $R_{23}$, $R_{24}$, $R_{25}$, J, V and p are defined as in this specification and a nitrite containing thioester is representative of the K-T-D group as defined in this specification may be prepared according to Scheme 34. The carboxylic acid group of formula 45 is converted to the thioester of formula 46 wherein p, $R_e$ and $R_f$ are defined as in this specification by reaction with an appropriate protected alcohol containing thiol agent wherein $P^1$ is as defined in this specification. Preferred methods for the formation of thioesters are reacting the thiol with the preformed acid chloride or symmetrical anhydride of the carboxylic acid or condensing the thiol and carboxylic acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula XIIA.

Nitroso compounds of formula (XII) wherein $R_e$, $R_f$, $R_{23}$, $R_{24}$, $R_{25}$, J, V and p are defined as in this specification and a nitrosothiol containing thioester is representative of the K-T-D group as defined in this specification may be prepared according to Scheme 35. The carboxylic acid group of formula 45 is converted to the thioester of formula 47 wherein p, $R_e$ and $R_f$ are defined as in this specification by reaction with an appropriate mono protected dithiol. Preferred methods for the formation of thioesters are reacting the free thiol with the preformed acid chloride or symmetrical anhydride of the carboxylic acid or condensing the free thiol and carboxylic acid with a dehydrating agent such as DCC or EDAC. HCl in the presence of a catalyst such as DMAP or HOBt. Preferred protecting groups for the thiol moiety are as a disulfide, a thioether such as a paramethoxybenzyl thioether, a tetrahydropyranyl thioether or a S-triphenylmethyl thioether. Deprotection of the thiol moiety (zinc in dilute aqueous acid, triphenylmethyl in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group). Reaction of the free thiol with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula XIIB. Alternatively, treatment of the thiol in compound 47 with a stoichiometric quantity of sodium nitrite in aqueous or alcoholic acid affords the compound of the formula XIIB.

Nitro compounds of formula (XII) wherein $R_e$, $R_f$, $R_{23}$, $R_{24}$, $R_{25}$, J, V and p are defined as in this specification and a nitrate containing thioester is representative of the K-T-D group as defined in this specification may be prepared according to Scheme 36. The carboxylic acid group of formula 45 is converted to the thioester of formula 46 wherein p, $R_e$ and $R_f$ are defined as in this specification by reaction with an appropriate protected alcohol containing thiol agent wherein $P^1$ is as defined in this specification. Preferred methods for the formation of thioesters are reacting the thiol with the preformed acid chloride or symmetrical anhydride of the carboxylic acid or condensing the thiol and carboxylic acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction of the alcohol with a suitable nitrating agent such as nitric acid and acetic anhydride in ethyl acetate/acetic acid affords the compound of the formula XIIC.

Nitroso compounds of formula () wherein $R_e$, $R_f$, $R_{31}$, $R_{32}$, and p are defined as in this specification and a nitrite containing ester is representative of the D group as defined in this specification may be prepared according to Scheme 37. The carboxylic acid group of formula 48 is converted to the ester of formula 49 wherein p, $R_e$ and $R_f$ are defined as in this specification by reaction with an monoprotected protected diol wherein $P^1$ is as defined in this specification. Preferred methods for the formation of esters are reacting the alcohol with the preformed acid chloride or symmetrical anhydride of the carboxylic acid or condensing the alcohol and carboxylic acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula XIIIA.

Nitroso compounds of formula (XIII) wherein $R_e$, $R_f$, $R_{31}$, $R_{32}$, and p are defined as in this specification and a nitrosothiol containing ester is representative of the D group as defined in this specification may be prepared according to Scheme 38. The carboxylic acid group of formula 48 is converted to the ester of formula 50 wherein p, $R_e$ and $R_f$ are defined as in this specification by reaction with an appropriate protected thiol containing alcohol. Preferred methods for the formation of esters are reacting the alcohol with the preformed acid chloride or symmetrical anhydride of the carboxylic acid or condensing the primary thiol and carboxylic acid with a dehydrating agent such as DCC or EDAC. HCl in the presence of a catalyst such as DMAP or HOBt. Preferred protecting groups for the thiol moiety are as a disulfide, a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group). Reaction of the free thiol with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula XIIIB. Alternatively, treatment of the thiol in compound 50 with a stoichiometric quantity of sodium nitrite in aqueous or alcoholic acid affords the compound of the formula XIIIB.

Nitro compounds of formula (XIII) wherein $R_e$, $R_f$, $R_{31}$, $R_{32}$, and p are defined as in this specification and a nitrate containing ester is representative of the D group as defined in this specification may be prepared according to Scheme 39. The carboxylic acid group of formula 48 is converted to the ester of formula 49 wherein p, $R_e$ and $R_f$ are defined as in this specification by reaction with an appropriate monoprotected protected diol wherein $p^1$ is as defined in this specification. Preferred methods for the formation of esters are reacting the alcohol with the preformed acid chloride or symmetrical anhydride of the carboxylic acid or condensing the alcohol and carboxylic acid with a dehydrating agent such as DCC or EDAC. HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction of the alcohol with a suitable nitrating agent such as nitric acid and acetic anhydride in ethyl acetate/acetic acid affords the compound of the formula XIIIC. Alternatively, carboxylic acid group of the formula 48 is converted to the ester of the formula 51 wherein p, $R_e$ and $R_f$ are defined as in this specification and X is a halogen by reaction with an appropriate halide containing alcohol. Preferred methods for the formation of esters are reacting the alcohol with the preformed acid chloride or symmetrical anhydride of the halide containing acid or condensing the alcohol and halide containing alcohol with a dehydrating agent such as DCC or EDAC. HCl in the presence of a catalyst such as DMAP or HOBt. Preferred halides are bromide and iodide. Reaction of the ester of the formula 51 with a suitable nitrating agent such as silver nitrate in an inert solvent such as acetonitrile affords the compound of the formula XIIIC.

As noted above, another aspect the invention provides a composition comprising (i) a therapeutically effective amount of a PDE inhibitor, which optionally can be substituted with at least one NO or $NO_2$ group or a group that stimulates endogenous production of NO or EDRF in vivo, and (ii) a compound that donates, transfers or releases nitrogen monoxide as a charged species, i.e., nitrosonium ($NO^+$) or nitroxyl ($NO^-$), or as the neutral species, nitric oxide (NO.) and/or a compound that stimulates endogenous production of NO or EDRF in vivo.

The compounds that donate, transfer or release nitric oxide can be any of those known to the art, including those mentioned and/or exemplified below.

Nitrogen monoxide can exist in three forms: $NO^-$ (nitroxyl), NO. (nitric oxide) and $NO^+$ (nitrosonium). NO. is a highly reactive short-lived species that is potentially toxic to cells. This is critical, because the pharmacological efficacy of NO depends upon the form in which it is delivered. In contrast to NO., nitrosonium and nitroxyl do not react with $O_2$ or $O_2^-$ species. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO.) and charged nitric oxide species, particularly including nitrosonium ion ($NO^+$) and nitroxyl ion ($NO^-$). The reaction form of nitric oxide can be provided by gaseous nitric oxide. The nitric oxide releasing, delivering or transferring compounds, having the structure F—NO wherein F is a nitric oxide releasing, delivering or transferring moiety, include any and all such compounds which provide nitric oxide to its intended site of action in a form active for their intended purpose. As used here, the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-((E))-hydroxyimino)-5-nitro-3-hexeneamines or hexeneamides, nitrosoamines, as well as substrates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated-modified and unmodified oligonucleotides (preferably of at least 5, and more particularly 5–200, nucleotides); and an S-nitrosylated hydrocarbons where the hydrocarbon can be a branched or unbranched, and saturated or unsaturated aliphatic hydrocarbon, or an aromatic hydrocarbon; S-nitrosylated hydrocarbons having one or more substituent groups in addition to the S-nitroso group; and heterocyclic compounds. S-nitrosothiols and the methods for preparing them are described in U.S. Pat. No. 5,380,758; Oae et al., *Org. Prep. Proc. Int.*, 15(3):165–198 (1983); Loscalzo et al., *J. Pharmacol. Exp. Ther.*, 249(3):726729 (1989) and Kowaluk et al., *J. Pharmacol. Exp. Ther.*, 256:1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof) from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

(i)

wherein x equals 2 to 20 and $R_e$ and $R_f$ are as defined in this specification;

(ii)

wherein x equals 2 to 20; and $R_e$ and $R_f$ are as defined in this specification;

(iii)

and

(iv)

wherein x equals 2 to 20; $R_e$ and $R_f$ are as defined in this specification; and B is selected from the group consisting of fluoro, $C_1$–$C_6$ alkoxy, cyano, carboxamido, cycloalkyl, arylalkoxy, alkylsulfinyl, arylthio, alkylamino, dialkylno, hydroxy, carbamoyl, N-alkylcarbamoyl, N,N-dialkylcarbamoyl, amino, hydroxyl, carboxyl, hydrogen, nitro and aryl.

Nitrosothiols can be prepared by various methods of synthesis. In general, the thiol precursor is prepared fist, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric, acetic and hydrochloric acids. Alternatively, the precursor thiol may be nitrosylated by treatment with an alkyl nitrite such as tert-butyl nitrite.

Another group of such NO adducts are those wherein the compounds donate, transfer or release nitric oxide and are selected from the group consisting of compounds that include at least one ON—N— or ON—C— group. The compound that includes at least one ON—N— or ON—C— group is preferably selected from the group consisting of ON—N—or ON—C-polypeptides (the term "polypeptide" includes proteins and also polyamino acids that do not possess an ascertained biological function, and derivatives thereof); ON—N— or ON—C-amino acids(including natural and synthetic amino acids and their stereoisomers and racemic mixtures); ON—N— or ON—C-sugars; ON—N— or ON—C-modified and unmodified oligonucleotides (preferably of at least 5, and more particularly 5–200, nucleotides), ON—O—, ON—N— or ON—C-hydrocarbons which can be branched or unbranched, saturated or unsaturated aliphatic hydrocarbons or aromatic hydrocarbons; ON—N— or ON—C— hydrocarbons having one or more substituent groups in addition to the ON—N— or ON—C— group; and ON—N— or ON—C-heterocyclic compounds.

Another group of such NO adducts is the nitrites which have an —O—NO group wherein the organic template to which the nitrite group is appended is a protein, polypeptide, amino acid, carbohydrate, branched or unbranched and saturated or unsaturated alkyl, aryl or a heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and are selected from the group consisting of compounds that include at least one at least one $O_2N$—O—, $O_2N$—N—, $O_2N$—S— or $O_2N$—C— group. Preferred among these are those selected from the group consisting of $O_2N$—O—, $O_2N$—N—, $O_2N$—S— or $O_2N$—C-polypeptides; $O_2N$—O—, $O_2N$—N—, $O_2N$—S— or $O_2N$—C-amino acids; $O_2N$—O—, $O_2N$—N—$O_2N$—S— or $O_2N$—C— sugars; $O_2N$—O—, $O_2N$—N—, $O_2N$—S— or $O_2N$—C-modified and unmodified oligonucleotides; $O_2N$—O—, $O_2N$—N—, $O_2N$—S— or $O_2N$—C— hydrocarbons which can be branched or unbranched, saturated or unsaturated aliphatic hydrocarbons or aromatic hydrocarbons; $O_2N$—O—, $O_2N$—N—, $O_2N$—S— or $O_2N$—C— hydrocarbons having one or more substituent groups in addition to the $O_2N$—O, $O_2N$—N—, $O_2N$—S— or $O_2N$—C— group; and $O_2N$—O—, $O_2N$—N—, $O_2N$—S— or $O_2N$—C— heterocyclic compounds. Preferred examples are isosorbide dinitrate and isosorbide mononitrate.

Another group of such NO adducts is the nitroso-metal compounds which have the structure $(R)_u$—A—$M(NO)_v$. R includes polypeptides (the termn "polypeptide" includes proteins and also polyamino acids that do not posses an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups in addition to the A-nitroso group; and heterocyclic compounds. A is S, O, or N, u and v are each integers independently selected from 1, 2 and 3, and M is a metal, preferably a transition metal. Preferred metals include iron, copper, manganese, cobalt, selenium and luthidium. Also contemplated are N-nitrosylated metal centers such as nitroprusside.

Another group of such adducts are 2-hydroxy-2-nitrosohydrazines which donate, transfer or release nitric oxide and have a $R_{61}R_{62}$—N(O—M$^+$)—NO group wherein $R_{61}$ and $R_{62}$ include polypeptides, amino acids, sugars, modified and unmodified oligonucleotides, hydrocarbons where the hydrocarbon can be a branched or unbranched, and saturated or unsaturated aliphatic hydrocarbon or an aromatic hydrocarbon, hydrocarbons having one or more substituent groups and heterocyclic compounds. M$^+$ is a metal cation, such as, for example, a Group I metal cation.

Another group of such adducts are thionitrates which donate, transfer or release nitric oxide and have the structure $R_{61}$—S—$NO_2$ wherein $R_{61}$ is as described above.

Compounds that stimulate endogenous synthesis of NO or EDRF in vivo include L-arginine, the substrate for nitric oxide synthase, cytokines, adenosine, bradykinin, calreticulin, bisacodyl, phenolphthalein, and endothelin.

When administered in vivo, the nitric oxide may be administered in combination with pharmaceutical carriers and in dosages described herein.

The nitrosated or nitrosylated compounds of the invention are used at dose ranges and over a course of dose regimen and are administered in the same or substantially equivalent vehicles/carrier by the same or substantially equivalent oral or nasal inhalant devices as their non-nitrosated or non-nitrosylated counterparts. The nitrosated or nitrosylated compounds of the invention can also be used in lower doses and in less extensive regimens of treatment. The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

While the compounds of the invention can be administered as the sole active pharmaceutical agent, they can also be used in combination with one or more compounds which are known to be effective against the specific disease state targeted for treatment. The compositions of the invention can also be administered as described above or can be made to include one or more additional active compounds which are known to be effective against the specific disease state is targeted for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

These and other aspects of the present invention will be apparent to those skilled in the art from the teachings herein.

EXAMPLE 1

2,6-bis(diethyl(3-methyl-3(nitrosothiol)butyric acid ester)amino)-4,8-dipiperidinopyrimido-[5,4d]-pyrimidine 1a. 3-Methyl-3(2,4,6-trimethoxyphenylmethylthio) butyric Acid To a solution of 3-mercapto-3-methylbutyric acid (B. J. Sweetman et al. *J. Med Chem.*, 14, 868 (1971)) (4.6 g, 34 mmol) in methylene chloride (250 mL) under nitrogen and cooled over ice/salt to 5 ûC (internal temperature) was added trifluoroacetic acid (82 g, 0.72 mol). No significant temperature rise was noted during the addition. To this was then added dropwise a solution of 2,4,6-trimethoxybenzyl alcohol (M. C. Munson et al., *J. Org. Chem.*, 57, 3013 (1992)) (6.45 g, 32 mmol) in methylene chloride (150 mL) such that the reaction temperature does not rise above 5 ûC. After the addition was complete, the mixture was stirred for an additional 5 min at 5 ûC and the volatiles were removed in vacuo (toluene or ethyl acetate can be used to assist in the removal of volatile material). The residue was partitioned between diethyl ether and water and the organic phase dried over anhydrous sodium sulfate, filtered and the volatile material removed in vacuo. The residue was treated with activated charcoal and recrystalised from diethyl ether/hexane. The product was isolated as an white solid in 70% yield (7 g) mp 103–105° C. $^1$H NMR (CDCl$_3$) δ6.12 (s, 2H), 3.80–3.85 (m, 11 H), 2.74 (s, 2H), 1.47 (s, 6H). $^{13}$C NMR (CDCl$_3$) δ173.9, 160.6, 158.6, 105.6, 90.5, 55.7, 55.3, 45.9, 43.6, 28.4, 21.0.

1b. 2,6-bis(diethyl-3-methyl-3(2,4,6-trimethoxyphenylmethylthio)butyric acid ester) amino)-4,8-dipiperidinopyrimido-[5,4-d]pyrimidine Under a nitrogen atmosphere, dipyridamole (1.50 g, 2.97 mmol) was dissolved in anhydrous dimethylformamide (30 mL) and 4-dimethylaminopyridine (1.46 g, 11.9 mmol) was added, followed by the product of Example 1a (3.64 g, 11.9 mmol) and EDAC (2.28 g, 11.9 mmol). The resulting mixture was stirred 44 hours at 50° C. The solvent was evaporated in vacuo and, residue was partitioned between methylene chloride and water, washed with brine and dried over anhydrous sodium sulfate. Volatiles were evaporated and the residue was purified by flash chromatography on silica gel, eluting with hexane/ethyl acetate (2:1) to (1:1) to give the title compound (1.02 g, 23 % yield). $^1$HÊNMR (CDCl$_3$, 300 MHz) δ1.45 (s, 24 H), 1.58–1.69 (m 12 H), 2.70 (s, 8 H), 3.64–3.88 (m, 52 H), 4.02–4.06 (m, 8 H), 4.25–4.32 (m, 8 H), 6.10 (s, 8H).

1c. 2,6-bis(diethyl-3methyl-3-mercaptobutyric acid ester)amino)4,8-dipiperidinopyrimido-[5,4-d]-pyrimidine The product of Example 1b (1.00 g, 0.63 mmol) was dissolved in methylene chloride (5.5 ÊmL) and anisole (4.0 mL, 36.9 mmol), phenol (0.400 g, 4.25 mmol), water (4.0 mL) and trifluoroacetic acid (16 mL, 208 mmol) were added. After 1 hour 30 minutes of stirring at room temperature, toluene (5 mL) was added and volatiles were evaporated. The residue was purified by flash chromatography on silica gel eluting with hexane/ ethyl acetate (5:1) to (3:1) to give the title compound (0.360 g, 59 % yield). $^1$H NMR (CDCl$_3$, 300 MHz) δ1.47 (s 24 H), 1.68–1.72 (m, 12 H), 2.29 (s, 4H), 2.63 (s, 8 H), 3.85–3.92 (m, 8 H), 3.97–4.03 (m, 8 H), 4.284.35 (m, 8H).

1d. 2,6-bis(diethyl(3-methyl-3(nitrosothiol)butyric acid ester)amino)-4,8-dipiperidinopyrimido-[5,4-d]-pyrimidine The product of Example 1c (0.353 g, 0.36 mmol) was dissolved in acetic acid (20 ÊmL) and 1N solution of hydrochloric acid (3.5 mL) was added, followed by 1 N sodium nitrite solution (2.2 mL). After 30 minutes stirring at room temperature, the reaction mixture was lyophilized, the residue was suspended in methylene chloride and washed with water, brine, and dried over anhydrous sodium sulfate. The solvent was evaporated in vacuo and the residue was purified by flash chromatography on silica gel eluting methylene chloride/methanol (12:1) to give the title compound (0.144 g, 37% yield). (CDCl$_3$, 300 MHz) δ1.52–1.73 (m, 12 H), 1.98 (s, 24 H), 3.20–3.38 (m, 8 H), 3.39–3.92 (m, 12 H), 3.94–4.35 (m, 12 H).

EXAMPLE 2

1-[-4-[(1,3-benzodioxol-5-ylmethyl)amino]-6-chloro-2-quinazolinyl]-4-piperidine-carboxylic ethyl-(3-methyl-3(nitrosothiol)butyramide) thioester hydrochloride

2a. 3-Methyl-3(thioacetyl)butyric Acid

To a solution of 3-mercapto-3-methylbutyric acid (B. J. Sweetman et al. *J. Med Chem.*, 14, 868 (1971)) (1.03 g, 7.7 mmol) in pyridine (1.6 mL) was added acetic anhydride (1.57 g, 15.4 mmol) and the reaction mixture was stirred at room temperature over night. The reaction mixture was slowly added to a 0° C. solution of 1 N HCl (20 ml) then water (10 ml) was added and the reaction mixture was stirred at room temperature for 2 hours. The solution was extracted with diethyl ether and the organic phase was washed with brine and then dried over anhydrous sodium sulfate. The solvent was evaporated in vacuo and the residue was purified by Sash chromatography on silica gel eluting with ethyl acetate/hexane (1:4) to give the title compound (0.791 g, 58 % yield). (CDCl$_3$, 300 MHz) δ: 1.55 (s, 6 H), 2.25 (s, 3H), 2.99 (s, 2H).

2b. Mercaptomethyl-3-Methyl-3(thioacetyl) butyramide

The product of Example 2a (0.556 g, 3.1 mmol) was dissolved in methylene chloride (10 ml) containing a catalytic amount of dimethylforamide (10 μl). Oxalyl chloride (0.556 g, 4.4 mmol) was added and the reaction mixture was stirred at room temperature for 1 hour. The volatile components were then evaporated in vacuo and the residue azeotroped with toluene (2×5 ml). The yellow oil remaining added to a −78° C. solution of 2-aminoethanethiol hydrochloride (0.341 g, 3.0 mmol), and triethylamine (0.303 g, 3.0 mmol) in dimethylformamide (6 ml). The reaction mixture was stirred at −78° C. for 1 hour and then at room temperature for 2 hours. The reaction was quenched with water (20 ml) and then extracted with ethyl acetate. The organic phase was dried over anhydrous sodium sulfate and then concentrated in vacuo to afford the title compound (0.349 g, 53 % yield) which was used without further purification. (CDCl$_3$, 300 MHz) δ: 1.5 (s, 6 H), 2.3 (s, 3 H), 2.6 (dd, 2 H), 2.8 (s, 2 H), 2.9 (s, 1H), (dd, 2 H), 6.0 (brs, 1H).

2c. Mecaptoethyl-3-Methyl-3(mercapto)butyramide

The product of Example 2b (0.314 g, 1.4 mmol) was dissolved in methanol (10 ml) and solid sodium hydroxide (85 mg, 2.1 mmol) was added. After stirring 5 minutes, the reaction mixture was diluted with ethyl acetate (50 ml) and washed with saturated aqueous sodium bicarbonate, followed by brine, and then dried over anhydrous sodium sulfate. The volatile components were evaporated in vacuo leaving the title compound as a colorless oil (0.1 88 g, 75 % yield) which was used without further purification. (CDCl$_3$, 300 MHz) δ: 1.42 (s, 6 H),1.55 (s, 1 H), 2.17 (s, 1 H), 2.41 (s, 2 H, 2.61 (dd, J=12.5 Hz, 6.2 Hz, 2H), 3.39 (dd, J=12.5 Hz, 6.2 Hz, 2H).

2d. 4-[(1,3-benzodioxol-5-ylmethyl)amino]-2,6-dichloro Quinazoline

A solution of 2,4,6-trichloroquinazoline (0.186 g, 0.80 mmol) in ethanol (20 mL) was heated to 55° C. and piperonylamine (0.145 g, 0.96 mmol) was added. The resulting mixture was stirred at 55° C. overnight. Volatiles were evaporated and the residue was partitioned between methylene chloride and saturated solution of ammonium hydroxide. The organic phase was dried over anhydrous sodium sulfate and concentrated in vacuo to yield 0.268 g (96 % yield) of the title compound as a white solid. $^1$H NMR (300 ÊMt, DMSO) δ4.59–4.63 (d, 2 H), 5.98 (s, 2 H), 6.86 (s, 2 H), 6.96 (s, 1 H), 7.62–7.66 (d, 1 H), 7.79–7.84 (d, 1 H), 8.46 (s, 1 H), 9.24–9.28 (t, 1 H).

2e. 1-[-4-[(1,3-benzodioxol-5-ylmethyl]amino]-6-chloro-2-quinazolinyl]-4-piperidine-carboxylic Acid Ethyl Ester The product of Example 2d (0.164 g, 0.47 mmol) and ethyl isonipecotate (0.200 ÊmL, 1.27 mmol) were combined in 5 g of phenol. The resulting mixture was heated at reflux temperature (240° C.) for 5 hours. The mixture was allowed to cool down, dissolved in 20 ml of chloroform and washed with IN solution of sodium hydroxide (2 5 40 mL). The organic fraction was dried over anhydrous sodium sulfate and concentrated in vacuo. The residue was purified by flash chromatography on silica gel, eluting with hexane/ethyl acetate (9:1) to (5:1) to give 0.164 g (53 % yield) of the title compound as a solid $^1$H NMR (300 ÊMHz, CDCl$_3$) δ1.24–1.30 (t, 3 H), 1.70–1.79 (m, 2 H), 1.96–2.0 (m, 2 H), 2.54–2.58 (m, 1 H), 3.01–3.10 (t, 2 H), 4.10–4.20 (q, 2 H), 4.66–4.70 (d, 2 H), 4.77–4.84 (d, 2 H), 5.59 (s, 1 H), 5.97 (s, 2 H), 6.77–6.89 (m, 3 H), 7.40–7.45 (m, 3 ).

2f. 1-[4-[(1,3-benzodioxol-5-ylmethyl)amino]-6-chloro-2-quinazolinyl]-4-piperidine-carboxylic Acid The product of Example 2e (0.100 g, 0.21 mmol) was dissolved in ethanol (1 mL) and water (0.5 mL) was added, followed by sodium hydroxide (0.082 g, 2.05 mmol). The resulting mixture was heated at 100° C. for 20 minutes. The volatiles were evaporated, the residue was diluted with water (2 mL) and 1n HCl was added until the pH of the reaction mixture registered pH 7. The reaction mixture was then filtered and the precipitate was washed with water (2 mL).

Ethanol was added to the precipitate and the volatiles were evaporated to give 0.080 g (86 % yield) of the title compound as a pale yellow solid. $^1$H NMR (300 ÊMHz, DMSO) δ1.36–1.45 (m, 2 H), 1.75–1.83 (m, 2 H), 2.92–3.02 (m, 3 H), 4.54–4.60 (m, 4 H), 5.94 (s, 2 H), 6.83 (s, 2 H), 6.93 (s, 1 H), 7.21–7.26 (d, 1 H), 7.44–7.49 (d, 1 H), 8.13 (s, 1 H), 8.51–8.53 (t, 1 H).

2g. 1-[4-[(1,3-benzodioxol-5-ylmethyl)amino]-6-chloro-2-quinazolinyl]-4-piperidine-carboxylic ethyl-(3-methyl-3(thioacetyl)butyramide) Thioester Under a nitrogen atmosphere, the product of Example 2f (0.147 g, 0.31 mmol) and triethylamine (0.043 mL, 0.31 mmol) were combined in 3 mL of DMF and heated to 50° C. to dissolve all solid. A solution of 2c (0.067 g, 0.38 mmol) in DMF (2 mL) was added, followed by EDAC (0.073 g, 0.38 mmol) and DMAP (0.015 g, 0.12 mmol). The resulting mixture was stirred at room temperature for 5 hours and then at 50° C. overnight. The reaction mixture was diluted with water (20 mL) and extracted with dichloromethane. The combined organic phase was washed with brine and dried over anhydrous sodium sulfate. The volatiles were evaporated and the residue was purified by flash chromatography on silica gel eluting with hexane/ ethyl acetate (1:2) to give 0.038 g (21 % yield) of the title compound. $^1$H NMR (300 ÊMH, CDCl$_3$) d: 1.48 (s, 6 H), 1.64–1.75 (m, 2 H), 1.94–2.00 (m, 2 H), 2.04 (s, 1 H), 2.45 (s, 2 H), 2.70–2.77 (m, 1 H), 2.91–2.96 (t, 2 H), 3.01–3.08 (t, 2 H), 3.42–3.48 (t, 2 H), 4.64–4.68 (d, 2 H), 4.87–4.94 (d, 2 H), 5.64–5.68 (m, 1 H), 5.96 (s, 2 H), 6.17–6.20 (m, 1 H), 6.75–6.85 (m, 3 H), 7.38–7.45 (m, 3 H).

2h. 1-[-4[(1,3-benzodioxol-5-ylmethyl)amino]-6-chloro-2-quinazolinyl]-4-piperidine-carboxylic ethyl-(3-methyl-3(nitrosothiol)butyramide) Thioester Hydrochloride The product of Example 2g (0.034 g, 0.057 mmol) was dissolved in methanol/dichloromethane (1 mL, 1:1) and 4N HCl in ether (0.100 mL) was added. Concentration in vacuo afforded a white solid. The white solid was then dissolved in a mixture of methylene chloride (3 ÊmL) and methanol (1 mL), and the resulting solution was cooled to 0° C. Tert-butyl nitrite (0.034 mL, 0.29 mmol) was added and the reaction mixture was stirred at 0° C. for 30 minutes. The volatiles were evaporated to give 0.037 g (98 % yield) of the title compound as a green solid. $^1$H NMR (300 ÊMHz, CDCl$_3$) δ1.61–1.76 (m, 4 H), 1.99 (s, 6 H), 2.66–2.85 (m, 1 H), 2.90–3.04 (m, 2 H), 3.18–3.45 (m, 4 H), 3.48 (s, 2 H), 4.59–4.86 (m, 4 H), 5.87 (s, 2 H), 6.62–6.71 (d, 1 H), 6.74 (s, 1 H), 6.80–6.88 (d, 1 H), 6.90 (s, 1 H), 7.48–7.56 (m, 1 H), 7.65–7.76 (m, 1 H), 8.14–8.19 (d, 1 H), 8.43 (s, 1 H).

EXAMPLE 3

In Vitro Comparative Relaxation Responses

Human corpus cavernosum tissue biopsies were obtained at the time of penile prosthesis implantation from impotent men. The tissue was maintained in a chilled Krebs-bicarbonate solution prior to assay. The tissue was cut into strips of 0.3×0.3×1 cm and suspended in organ chambers for isometric tension measurement. Tissues were incrementally stretched until optimal isometric tension for contraction was obtained. Once this was achieved, the tissues were contracted with phenylephine ($7\times10^{-7}$ M) and once a stable contraction was achieved, the tissues were exposed to either dipyridamole or Example 1 ($10^{-6}$ to $3\times10^{-5}$ M) by cumulative additions to the chamber. At the end of the experiment papaverine ($10^{-4}$ M) is added to obtain maximal relaxation. FIG. 40 shows that the compound of Example 1 at doses of 10 μM and 30 μM is more efficacious in relaxing the phenylephrine-induced contaction than is an equimolar dose of the phosphodiesterase inhibitor dipyridamole. Data are expressed as the percent loss in tone from the phenylephrine-induced contraction (0%=phenylephrine contraction; –100% tone after the administration of papaverine).

What is claimed is:

1. A method for treating a female sexual dysfunction in a female individual in need thereof comprising administering to the female individual a therapeutically effective amount of a compound of formula $R_{61}R_{62}$—N(O—M$^+$)—NO, wherein $R_{61}$ and $R_{62}$ are each independently a polypeptide, an amino acid, a sugar, an oligonucleotide, a hydrocarbon or a heterocyclic compound; and M is a metal cation, and at least one of a nitrosated phosphodiesterase inhibitor, a nitrosylated phosphodiesterase inhibitor, or a nitrosated and nitrosylated phosphodiesterase inhibitor.

2. The method of claim 1, wherein the nitrosated phosphodiesterase inhibitor, the nitrosylated phosphodiesterase inhibitor or the nitrosated and nitrosylated phosphodiesterase inhibitor is a nitrosated compound, a nitrosylated compound or a nitrosated and nitrosylated compound selected from piclamilast, ORG 20241, filaminast, rolipram, MCI-154, roflumilast, toborinone, vesnarinone, posicor, 6-bromo-1,5-dihydro-imidazo(2,1-b) quinazolin-2(3H)-one, R 79595, lixazinone, zaprinast, sildenafil, pimobendan, motapizone, siguazodan, 4,5-dihydro-5-methyl-6(4-(4oxo-1 (4H)-pyridinyl)phenyl)-3(2H)-pyridazinone, EMD 53998, zardaverine, CI 930, ICI 153,110, imazodan, loprinone, saterinone, albifylline, torbafylline, denbufylline, WIN 63291, doxofylline, theophylline, pentoxifylline, cilostamide, cilostazol, nanterinone, 4-((1,2-dihydro-2-oxo-6-quinolinyl)oxy)-N-ethyl-N-phenyl-butanamide, 4-((1,2-dihydro-2-oxo-6-quinolinyl)oxy)-N-methyl-N-phenyl-butanamide, N-butyl-4-((1,2-dihydro-2oxo-6-quinolinyl)oxy)N-phenyl-butanamide, MS 857, WIN 62582, amrinone, milrinone, loprinone, CDP 840, piroximone, benafentrine, tolafentrine, dipyridomole, papaverine, E 4021, a thienopyrimidine derivative, papaveroline and trifusal.

3. The method of claim 1, wherein the compound of formula $R_{61}R_{62}$—N(O—M$^+$)—NO, and the at least one of a nitrosated phosphodiesterase inhibitor, a nitrosylated phosphodiesterase inhibitor, or a nitrosated and nitrosylated phosphodiesterase inhibitor are administered separately as part of the same dosage regimen.

4. The method of claim 1, wherein the compound of formula $R_{61}R_{62}$—N(O—M$^+$)—NO, and the at least one of a nitrosated phosphodiesterase inhibitor, a nitrosylated phosphodiesterase inhibitor, or a nitrosated and nitrosylated phosphodiesterase inhibitor are administered together in the form of a composition.

5. The method of claim 1, further comprising administering a pharmaceutically acceptable carrier.

6. A method for treating a female sexual dysfunction in a female individual in need thereof comprising administering to the female individual a therapeutically effective amount of at least one of an (E)-alkyl-2-((E)-hydroxyimino)-5-nitro-3-hexenamine or an (E)-alkyl-2-((E)-hydroxyimino)-5-nitro-3-hexenamide, and at least one of a nitrosated phosphodiesterase inhibitor, a nitrosylated phosphodiesterase inhibitor or a nitrosated and nitrosylated phosphodiesterase inhibitor.

7. The method of claim 6, wherein the nitrosated phosphodiesterase inhibitor, the nitrosylated phosphodiesterase inhibitor or the nitrosated and nitrosylated phosphodiesterase inhibitor is a nitrosated compound, a nitrosylated compound or a nitrosated and nitrosylated compound selected from piclamilast, ORG 20241, filaminast, rolipram, MCI-154, roflumilast, toborinone, vesnarinone, posicor, 6-bromo-1,5-dihydroimidazo(2,1-b) quinazolin-2(3H)-one, R 79595, lixazinone, zaprinast, sildenafil, pimobendan, motapizone, siguazodan, 4,5-dihydro-5-methyl-6(4-(4-oxo-1(4H)-pyridinyl)phenyl)-3(2H)-pyridazinone, EMD 53998, zardaverine, CI 930, ICI 153,110, imazodan, loprinone, saterinone, albifylline, torbafylline, denbufylline, WIN 63291, doxofylline, theophylline, pentoxifylline, cilostamide, cilostazol, nanterinone, 4-((1,2-dihydro-2-oxo-6quinolinyl)oxy)-N-ethyl-N-phenyl-butanamide, 4-((1,2-dihydro-2-oxo-6-quinolinyl)oxy)-N-methyl-N-phenyl-butananide, N-butyl-4- ((1,2-dihydro-2-oxo-6-quinolinyl)oxy)-N-phenyl-butanamide, MS 857, WIN 62582, amrinone, milrinone, loprinone, CDP 840, piroximone, benafentrine, tolafentrine, dipyridomole, papaverine, E 4021, a thienopyrimidine derivative, papaveroline and trifusal.

8. The method of claim 6, wherein the at least one of an (E)-alkyl-2-((E)-hydroxyimino)-5-nitro-3-hexenamine or an (E)-alkyl-2-((E)-hydroxyimino)-5-nitro-3-hexenamide, and the at least one of a nitrosated phosphodiesterase inhibitor, a nitrosylated phosphodiesterase inhibitor, or a nitrosated and nitrosylated phosphodiesterase inhibitor are administered separately as part of the same dosage regimen.

9. The method of claim 6, further comprising administering a pharmaceutically acceptable carrier.

10. A method for treating a female sexual dysfunction in a female individual in need thereof comprising administering to the female individual a therapeutically effective amount of a sydnonimine compound, and at least one of a nitrosated phosphodiesterase inhibitor, a nitrosylated phosphodiesterase inhibitor or a nitrosated and nitrosylated phosphodiesterase inhibitor.

11. The method of claim 10, wherein the nitrosated phosphodiesterase inhibitor, the nitrosylated phosphodiesterase inhibitor or the nitrosated and Nitrosylated phosphodiesterase inhibitor is a nitrosated compound, a nitrosylated compound or a nitrosated and nitrosylated compound selected from piclamilast, ORG 20241, filaminast, rolipram, MCI-154, roflumilast, toborinone, vesnarinone, posicor, 6-bromo-1,5-dihydro-imidazo(2,1-b) quinazolin-2(3H)-one, R 79595, lixazinone, zaprinast, sildenafil, pimobendan, motapizone, siguazodan, 4,5-dihydro-5-methyl-6(4-(4oxo-1(4H)-pyridinyl)phenyl)-3(2H)-pyridazinone, EMD 53998, zardaverine, CI 930, ICI 153,110, imazodan, loprinone, saterinone, albifylline, torbafylline, denbufylline, WIN 63291, doxofylline, theophylline, pentoxifylline, cilostamide, cilostazol, nanterinone, 4-((1,2-dihydro2-oxo-6-quinolinyl)oxy)-N-ethyl-N-phenyl-butanamide, 4-((1,2 dihydro-2-oxo-6-quinolinyl)oxy)-N-methyl-N-phenyl-butanamide, N-butyl-4-((1,2-dihydro-2-oxo-6-quinolinyl) oxy)-N-phenyl-butanamide, MS 857, WIN 62582, amrinone, milrinone, loprinone, CDP 840, piroximone, benafentrine, tolafentrine, dipyridomole, papaverine, E 4021, a thienopyrimidine derivative, papaveroline and trifusal.

12. The method of claim 10, wherein the sydnonimine compound and the at least one of a nitrosated phosphodiesterase inhibitor, a nitrosylated phosphodiesterase inhibitor, or a nitrosated and nitrosylated phosphodiesterase inhibitor are administered separately as part of the same dosage regimen.

13. The method of claim 10, wherein the sydnonimine compound and the at least one of a nitrosated phosphodiesterase inhibitor, a nitrosylated phosphodiesterase inhibitor, or a nitrosated and nitrosylated phosphodiesterase inhibitor are administered together in the form of a composition.

14. The method of claim 10, further comprising administering a pharmaceutically acceptable carrier.

15. The method of claim 6, wherein the at least one of an (E)-alkyl-2-((E)-hydroxyimino)-5-nitro3-hexenamine or an (E)alkyl-2-((E)-hydroxyimino)-5-nitro-3-hexenamide, and the at least one of a nitrosated phosphodiesterase inhibitor, a nitrosylated phosphodiesterase inhibitor, or a nitrosated and nitrosylated phosphodiester inhibitor are administered together in the form of a composition.

* * * * *